US009868934B2

(12) United States Patent
Kato et al.

(10) Patent No.: US 9,868,934 B2
(45) Date of Patent: Jan. 16, 2018

(54) METHOD FOR PRODUCING PLURIPOTENT STEM CELLS

(71) Applicant: Saitama Medical University, Saitama (JP)

(72) Inventors: Hidemasa Kato, Saitama (JP); Yosuke Moriyama, Saitama (JP); Keiko Hiraki, Saitama (JP); Akihiko Okuda, Saitama (JP)

(73) Assignee: Saitama Medical University, Saitama (JP)

( * ) Notice: Subject to any disclaimer, the term of this patent is extended or adjusted under 35 U.S.C. 154(b) by 0 days.

(21) Appl. No.: 14/439,037

(22) PCT Filed: Oct. 29, 2013

(86) PCT No.: PCT/JP2013/079311
§ 371 (c)(1),
(2) Date: Apr. 28, 2015

(87) PCT Pub. No.: WO2014/069479
PCT Pub. Date: May 8, 2014

(65) Prior Publication Data

US 2015/0275171 A1 Oct. 1, 2015

(30) Foreign Application Priority Data

Oct. 29, 2012 (JP) ................................. 2012-237734

(51) Int. Cl.

| | |
|---|---|
| ***C12N 5/0787*** | (2010.01) |
| ***C12N 5/078*** | (2010.01) |
| ***C12N 5/0797*** | (2010.01) |
| ***C12N 5/00*** | (2006.01) |
| ***C12N 5/074*** | (2010.01) |
| ***C12N 9/02*** | (2006.01) |

(52) U.S. Cl.
CPC ......... *C12N 5/0607* (2013.01); *C12N 5/0696* (2013.01); *C12N 9/0071* (2013.01); *C12Y 114/11* (2013.01); *C12N 2501/71* (2013.01); *C12N 2510/00* (2013.01)

(58) Field of Classification Search
None
See application file for complete search history.

(56) References Cited

U.S. PATENT DOCUMENTS

2014/0249208 A1* 9/2014 Bancel ................. A61K 48/005 514/44 R
2015/0232810 A1 8/2015 Luo et al.

FOREIGN PATENT DOCUMENTS

| | | |
|---|---|---|
| JP | 2013-126412 | 6/2013 |
| WO | WO2010/037001 A2 | 4/2010 |
| WO | WO 2001/075627 A1 | 6/2011 |
| WO | WO 2011/130624 A2 | 10/2011 |

OTHER PUBLICATIONS

Lee et al Tumorigenicity as a clinical hurdle for pluripotent stemcell therapies vol. 19 | No. 8 = Aug. 2013 nature medicine pp. 998-1004.*

Ngo, in The Protein Folding Problem and Tertiary Structure Prediction, Merz et al. (eds.), Birkhauser Boston: Boston, MA, pp. 433 and 492-495, 1994.*

Yan et al Science. Oct. 20, 2000;290(5491):523-7.Two-amino acid molecular switch in an epithelial morphogen that regulates binding to two distinct receptors.*

Lecchi Blood. 2015; 125(6):1006-1013)Identification of a new dysfunctional platelet P2Y12 receptor variant associated with bleeding diathesis.*

Rudinger (in Peptide Hormones, Parsons (ed.), University Park Press: Baltimore, MD, pp. 1-7, 1976.*

Okashita et al., PRDM14 promotes active DNA demethylation through the Teneleventranslocation (TET)-mediated base excision repair pathway in embryonic stem cells Stem Cells and REGENERATIONDevelopment (2014) 141, 269-280.*

Moreadith et al., 1997, J Mol Med pp. 208-216.*

Okashita et al PRDM14 maintains pluripotency of embryonic stem cells through TET-mediated active DNA demethylation Biochemical and Biophysical Research Communications pp. 138-145.*

Fan et alEffects of TET1 knockdown on gene expression and DNA methylation in porcine induced pluripotent stem cells Reproduction Dec. 1, 2013 146 569-579.*

Osafune et al Marked differences in differentiation propensity among human embryonic stem cell lines Nat Biotechnol. Mar. 2008;26(3):313-5.*

Hwang et al.,N-Terminal Acetylation of Cellular Proteins Creates Specific Degradation Signals Science Feb. 19, 2010: vol. 327, Issue 5968, pp. 973-977.*

Arnesen et al Proteomics analyses reveal the evolutionary conservation and divergence of N-terminal acetyltransferases from yeast and humans PNAS _May 19, 2009 _vol. 106 _No. 20 _8157-8162.*

International Preliminary Report on Patentability for International App No. PCT/JP2013/079311, dated May 14, 2015 (6 pages) (English translation).

(Continued)

*Primary Examiner* — Maria Leavitt
(74) *Attorney, Agent, or Firm* — Fish & Richardson P.C.

(57) ABSTRACT

The present invention allows a TET1 protein to be more stably expressed in human pluripotent stem cells than in the past by, inter alia, substituting the second amino acid from the amino terminal of a TET1 protein with a different amino acid. Furthermore upon differentiation of said pluripotent stem cells, it is possible to quickly eliminate the expression of, inter alia, NANOG, which is an inhibitor of differentiation and promote the expression of factors related to differentiation by introducing a variant TET1 protein to a pluripotent stem cell. The present invention provides a method for manufacturing pluripotent stem cells with increased differentiation potential, and a substance that is useful to said method.

14 Claims, 53 Drawing Sheets

(56) References Cited

OTHER PUBLICATIONS

International Search Report dated Feb. 4, 2014 for PCT/JP2013/079311.

Meelad M. Dawlaty et al., Tet1 Is Dispensable for Maintaining Pluripotency and Its Loss Is Compatible with Embryonic and Postnatal Development, Cell Stem Cell, 2011, 9(2), pp. 166-175.

Yufei Xu et al., Genome-wide Regulation of 5hmC, 5mC, and Gene Expression by Tet1 Hydroxylase in Mouse Embryonic Stem Cells, Molecular Cell, 2011, 42(4), pp. 451-464.

Hidemasa kato et al., TET1 wa Genko no. Hito iPS Saibo no Kekkan o Oginatte Saibo Bunka Koritsu o Hiyakuteki ni Josho saseru, Regenerative Medicine, Mar. 6, 2013, The 12$^{th}$ Congress of the Japanese Society for Regenerative Medicine Program Shoroku, p. 232, -064-3 (With English Translation).

Hackett JA et al., Germline DNA demethylation dynamics and imprint erasure through 5-hydroxymethylcytosine., Science, Jan. 2013, 339(6118), pp. 448-452.

Yawei Gao et al., Replacement of Oct. 4 by Tet1 during iPSC Induction Reveals an Important Role of DNA Methylation and Hydroxymethylation in Reprogramming., Cell Stem Cell, Apr. 2013, 12(4), pp. 453-649.

Yael Costa et al., NANOG-dependent function of TET1 and TET2 in establishment of Pluripotency., Nature, Mar. 2013, vol. 495, pp. 370-374.

Office Action dated Feb. 9, 2016 in corresponding Japanese patent application No. 2014-544531 (with partial English translation).

Hidemasa Kato et al., TET1 wa Genko no. Hito iPS Saibo no Kekkan o Oginatte Saibo Bunka Koritsu o Hiyakuteki ni Josho saseru, Regenerative Medicine, Feb. 28, 2013, The 12$^{th}$ Congress of the Japanese Society for Regenerative Medicine Program Shoroku, p. 232, 0-64-3 (With English Translation).

Hackett JA et al., Germline DNA demethylation dynamics and imprint erasure through 5-hydroxymethylcytosine, Science, Jan. 2013, 339(6118), pp. 448-452.

Yawei Gao et al., Replacement of Oct. 4 by Tet1 during iPSC Induction Reveals an Important Role of DNA Methylation and Hydroxymethylation in Reprogramming, Cell Stem Cell, Apr. 2013, 12(4), pp. 453-469.

Yael Costa et al., NANOG-dependent function of TET1 and TET2 in establishment of Pluripotency, Nature, Mar. 2013, vol. 495, pp. 370-374.

Polevoda and Sherman, *N-terminal Acetyltransferases and Sequence Requirements for N-terminal Acetylation of Eukaryotic Proteins*, J. Mol. Biol. 325:595-622 (2003).

Branco et al., *Uncovering the role of 5-hydroxymethylcytosine in the epigenome*, Nature Reviews, Genetics, 13:7-13, (Jan. 2012).

Cimmino et al., *TET Family Proteins and Their Role in Stein Cell Differentiation and Transformation*, Cell Stem Cell, 9:193-204, (Sep. 2011).

Ito et al., *Role of Tet proteins in 5mC to 5hmC conversion, ES-cell self-renewal and inner cell mass specification*, Nature, 466:1129-1135, (Aug. 2010).

Koh et al., *Tet1 and Tet2 Regulate 5-Hydroxymethylcytosine Production and Cell Lineage Specification in Mouse Embryonic Stem Cells*, Cell Stem Cell, 8:200-213, (Feb. 2011).

Extended European Search Report for corresponding EP App. No. 13851495.5, dated Apr. 14, 2016 (10 pages).

* cited by examiner

SEQUENCE LISTING

```
<160> NUMBER OF SEQ ID NOS: 46

<210> SEQ ID NO 1
<211> LENGTH: 9601
<212> TYPE: DNA
<213> ORGANISM: Homo sapiens
<220> FEATURE:
<221> NAME/KEY: CDS
<222> LOCATION: (506)..(6916)
```

```
<400> SEQUENCE: 1

agacactgct gctccggggg gctgacctgg cggggagtgg ccgcgcagtc tgctccggcg     60

ccgctttgtg cgcgcagccg ctggcccctc tactcccggg tctgcccccc gggacacccc    120

tctgcctcgc ccaagtcatg cagccctacc tgcctctcca ctgtggacct ttgggaaccg    180

actcctcacc tcgggggctc gggccttgac tgtgctggga gccggtaggc gtcctccgcg    240

acccgcccgc gcccctcgcg cccgccgggg ccccgggctc caaagttgtg gggaccggcg    300

cgagttggaa agtttgcccg agggctggtg caggcttgga gctgggggcc gtgcgctgcc    360

ctgggaatgt gacccggcca gcgaccaaaa ccttgtgtga ctgagctgaa gagcagtgca    420

tccagattct cctcagaagt gagactttcc aaaggaccaa tgactctgtt tcctgcgccc    480

tttcattttt tcctactctg tagct atg tct cga tcc cgc cat gca agg cct      532
                            Met Ser Arg Ser Arg His Ala Arg Pro
                            1               5

tcc aga tta gtc agg aag gaa gat gta aac aaa aaa aag aaa aac agc      580
Ser Arg Leu Val Arg Lys Glu Asp Val Asn Lys Lys Lys Lys Asn Ser
10                  15                  20                  25

caa cta cga aag aca acc aag gga gcc aac aaa aat gtg gca tca gtc      628
Gln Leu Arg Lys Thr Thr Lys Gly Ala Asn Lys Asn Val Ala Ser Val
                30                  35                  40

aag act tta agc cct gga aaa tta aag caa tta att caa gaa aga gat      676
Lys Thr Leu Ser Pro Gly Lys Leu Lys Gln Leu Ile Gln Glu Arg Asp
            45                  50                  55

gtt aag aaa aaa aca gaa cct aaa cca ccc gtg cca gtc aga agc ctt      724
Val Lys Lys Lys Thr Glu Pro Lys Pro Pro Val Pro Val Arg Ser Leu
        60                  65                  70

ctg aca aga gct gga gca gca cgc atg aat ttg gat agg act gag gtt      772
Leu Thr Arg Ala Gly Ala Ala Arg Met Asn Leu Asp Arg Thr Glu Val
    75                  80                  85

ctt ttt cag aac cca gag tcc tta acc tgc aat ggg ttt aca atg gcg      820
Leu Phe Gln Asn Pro Glu Ser Leu Thr Cys Asn Gly Phe Thr Met Ala
90                  95                  100                 105

cta cga agc acc tct ctt agc agg cga ctc tcc caa ccc cca ctg gtc      868
Leu Arg Ser Thr Ser Leu Ser Arg Arg Leu Ser Gln Pro Pro Leu Val
                110                 115                 120

gta gcc aaa tcc aaa aag gtt cca ctt tct aag ggt tta gaa aag caa      916
Val Ala Lys Ser Lys Lys Val Pro Leu Ser Lys Gly Leu Glu Lys Gln
            125                 130                 135

cat gat tgt gat tat aag ata ctc cct gct ttg gga gta aag cac tca      964
His Asp Cys Asp Tyr Lys Ile Leu Pro Ala Leu Gly Val Lys His Ser
        140                 145                 150

gaa aat gat tcg gtt cca atg caa gac acc caa gtc ctt cct gat ata     1012
Glu Asn Asp Ser Val Pro Met Gln Asp Thr Gln Val Leu Pro Asp Ile
    155                 160                 165

gag act cta att ggt gta caa aat ccc tct tta ctt aaa ggt aag agc     1060
Glu Thr Leu Ile Gly Val Gln Asn Pro Ser Leu Leu Lys Gly Lys Ser
170                 175                 180                 185

caa gag aca act cag ttt tgg tcc caa aga gtt gag gat tcc aag atc     1108
Gln Glu Thr Thr Gln Phe Trp Ser Gln Arg Val Glu Asp Ser Lys Ile
                190                 195                 200

aat atc cct acc cac agt ggc cct gca gct gag atc ctt cct ggg cca     1156
Asn Ile Pro Thr His Ser Gly Pro Ala Ala Glu Ile Leu Pro Gly Pro
            205                 210                 215

ctg gaa ggg aca cgc tgt ggt gaa gga cta ttc tct gaa gag aca ttg     1204
Leu Glu Gly Thr Arg Cys Gly Glu Gly Leu Phe Ser Glu Glu Thr Leu
        220                 225                 230
```

```
aat gat acc agt ggt tcc cca aaa atg ttt gct cag gac aca gtg tgt      1252
Asn Asp Thr Ser Gly Ser Pro Lys Met Phe Ala Gln Asp Thr Val Cys
    235                 240                 245

gct cct ttt ccc caa aga gca acc ccc aaa gtt acc tct caa gga aac      1300
Ala Pro Phe Pro Gln Arg Ala Thr Pro Lys Val Thr Ser Gln Gly Asn
250                 255                 260                 265

ccc agc att cag tta gaa gag ttg ggt tca cga gta gaa tct ctt aag      1348
Pro Ser Ile Gln Leu Glu Glu Leu Gly Ser Arg Val Glu Ser Leu Lys
                270                 275                 280

tta tct gat tct tac ctg gat ccc att aaa agt gaa cat gat tgc tac      1396
Leu Ser Asp Ser Tyr Leu Asp Pro Ile Lys Ser Glu His Asp Cys Tyr
            285                 290                 295

ccc acc tcc agt ctt aat aag gtt ata cct gac ttg aac ctt aga aac      1444
Pro Thr Ser Ser Leu Asn Lys Val Ile Pro Asp Leu Asn Leu Arg Asn
        300                 305                 310

tgc ttg gct ctt ggt ggg tct acg tct cct acc tct gta ata aaa ttc      1492
Cys Leu Ala Leu Gly Gly Ser Thr Ser Pro Thr Ser Val Ile Lys Phe
    315                 320                 325

ctc ttg gca ggc tca aaa caa gcg acc ctt ggt gct aaa cca gat cat      1540
Leu Leu Ala Gly Ser Lys Gln Ala Thr Leu Gly Ala Lys Pro Asp His
330                 335                 340                 345

caa gag gcc ttc gaa gct act gca aat caa cag gaa gtt tct gat acc      1588
Gln Glu Ala Phe Glu Ala Thr Ala Asn Gln Gln Glu Val Ser Asp Thr
                350                 355                 360

acc tct ttc cta gga cag gcc ttt ggt gct atc cca cat caa tgg gaa      1636
Thr Ser Phe Leu Gly Gln Ala Phe Gly Ala Ile Pro His Gln Trp Glu
            365                 370                 375

ctt cct ggt gct gac cca gtt cat ggt gag gcc ctg ggt gag acc cca      1684
Leu Pro Gly Ala Asp Pro Val His Gly Glu Ala Leu Gly Glu Thr Pro
        380                 385                 390

gat cta cca gag att cct ggt gct att cca gtc caa gga gag gtc ttt      1732
Asp Leu Pro Glu Ile Pro Gly Ala Ile Pro Val Gln Gly Glu Val Phe
    395                 400                 405

ggt act att tta gac caa caa gaa act ctt ggt atg agt ggg agt gtt      1780
Gly Thr Ile Leu Asp Gln Gln Glu Thr Leu Gly Met Ser Gly Ser Val
410                 415                 420                 425

gtc cca gac ttg cct gtc ttc ctt cct gtt cct cca aat cca att gct      1828
Val Pro Asp Leu Pro Val Phe Leu Pro Val Pro Pro Asn Pro Ile Ala
                430                 435                 440

acc ttt aat gct cct tcc aaa tgg cct gag ccc caa agc act gtc tca      1876
Thr Phe Asn Ala Pro Ser Lys Trp Pro Glu Pro Gln Ser Thr Val Ser
            445                 450                 455

tat gga ctt gca gtc cag ggt gct ata cag att ttg cct ttg ggc tca      1924
Tyr Gly Leu Ala Val Gln Gly Ala Ile Gln Ile Leu Pro Leu Gly Ser
        460                 465                 470

gga cac act cct caa tca tca tca aac tca gag aaa aat tca tta cct      1972
Gly His Thr Pro Gln Ser Ser Ser Asn Ser Glu Lys Asn Ser Leu Pro
    475                 480                 485

cca gta atg gct ata agc aat gta gaa aat gag aag cag gtt cat ata      2020
Pro Val Met Ala Ile Ser Asn Val Glu Asn Glu Lys Gln Val His Ile
490                 495                 500                 505

agc ttc ctg cca gct aac act cag ggg ttc cca tta gcc cct gag aga      2068
Ser Phe Leu Pro Ala Asn Thr Gln Gly Phe Pro Leu Ala Pro Glu Arg
                510                 515                 520

gga ctc ttc cat gct tca ctg ggt ata gcc caa ctc tct cag gct ggt      2116
Gly Leu Phe His Ala Ser Leu Gly Ile Ala Gln Leu Ser Gln Ala Gly
            525                 530                 535

cct agc aaa tca gac aga ggg agc tcc cag gtc agt gta acc agc aca      2164
Pro Ser Lys Ser Asp Arg Gly Ser Ser Gln Val Ser Val Thr Ser Thr
        540                 545                 550
```

```
gtt cat gtt gtc aac acc aca gtg gtg act atg cca gtg cca atg gtc      2212
Val His Val Val Asn Thr Thr Val Val Thr Met Pro Val Pro Met Val
    555                 560                 565

agt acc tcc tct tct tcc tat acc act ttg cta ccg act ttg gaa aag      2260
Ser Thr Ser Ser Ser Ser Tyr Thr Thr Leu Leu Pro Thr Leu Glu Lys
570                 575                 580                 585

aag aaa aga aag cga tgt ggg gtc tgt gaa ccc tgc cag cag aag acc      2308
Lys Lys Arg Lys Arg Cys Gly Val Cys Glu Pro Cys Gln Gln Lys Thr
                590                 595                 600

aac tgt ggt gaa tgc act tac tgc aag aac aga aag aac agc cat cag      2356
Asn Cys Gly Glu Cys Thr Tyr Cys Lys Asn Arg Lys Asn Ser His Gln
            605                 610                 615

atc tgt aag aaa aga aaa tgt gag gag ctg aaa aag aaa cca tct gtt      2404
Ile Cys Lys Lys Arg Lys Cys Glu Glu Leu Lys Lys Lys Pro Ser Val
        620                 625                 630

gtt gtg cct ctg gag gtt ata aag gaa aac aag agg ccc cag agg gaa      2452
Val Val Pro Leu Glu Val Ile Lys Glu Asn Lys Arg Pro Gln Arg Glu
    635                 640                 645

aag aag ccc aaa gtt tta aag gca gat ttt gac aac aaa cca gta aat      2500
Lys Lys Pro Lys Val Leu Lys Ala Asp Phe Asp Asn Lys Pro Val Asn
650                 655                 660                 665

ggc ccc aag tca gaa tcc atg gac tac agt aga tgt ggt cat ggg gaa      2548
Gly Pro Lys Ser Glu Ser Met Asp Tyr Ser Arg Cys Gly His Gly Glu
                670                 675                 680

gaa caa aaa ttg gaa ttg aac cca cat act gtt gaa aat gta act aaa      2596
Glu Gln Lys Leu Glu Leu Asn Pro His Thr Val Glu Asn Val Thr Lys
            685                 690                 695

aat gaa gac agc atg aca ggc atc gag gtg gag aag tgg aca caa aac      2644
Asn Glu Asp Ser Met Thr Gly Ile Glu Val Glu Lys Trp Thr Gln Asn
        700                 705                 710

aag aaa tca cag tta act gat cac gtg aaa gga gat ttt agt gct aat      2692
Lys Lys Ser Gln Leu Thr Asp His Val Lys Gly Asp Phe Ser Ala Asn
    715                 720                 725

gtc cca gaa gct gaa aaa tcg aaa aac tct gaa gtt gac aag aaa cga      2740
Val Pro Glu Ala Glu Lys Ser Lys Asn Ser Glu Val Asp Lys Lys Arg
730                 735                 740                 745

acc aaa tct cca aaa ttg ttt gta caa acc gta aga aat ggc att aaa      2788
Thr Lys Ser Pro Lys Leu Phe Val Gln Thr Val Arg Asn Gly Ile Lys
                750                 755                 760

cat gta cac tgt tta cca gct gaa aca aat gtt tca ttt aaa aaa ttc      2836
His Val His Cys Leu Pro Ala Glu Thr Asn Val Ser Phe Lys Lys Phe
            765                 770                 775

aat att gaa gaa ttc ggc aag aca ttg gaa aac aat tct tat aaa ttc      2884
Asn Ile Glu Glu Phe Gly Lys Thr Leu Glu Asn Asn Ser Tyr Lys Phe
        780                 785                 790

cta aaa gac act gca aac cat aaa aac gct atg agc tct gtt gct act      2932
Leu Lys Asp Thr Ala Asn His Lys Asn Ala Met Ser Ser Val Ala Thr
    795                 800                 805

gat atg agt tgt gat cat ctc aag ggg aga agt aac gtt tta gta ttc      2980
Asp Met Ser Cys Asp His Leu Lys Gly Arg Ser Asn Val Leu Val Phe
810                 815                 820                 825

cag cag cct ggc ttt aac tgc agt tcc att cca cat tct tca cac tcc      3028
Gln Gln Pro Gly Phe Asn Cys Ser Ser Ile Pro His Ser Ser His Ser
                830                 835                 840

atc ata aat cat cat gct agt ata cac aat gaa ggt gat caa cca aaa      3076
Ile Ile Asn His His Ala Ser Ile His Asn Glu Gly Asp Gln Pro Lys
            845                 850                 855

act cct gag aat ata cca agt aaa gaa cca aaa gat gga tct ccc gtt      3124
Thr Pro Glu Asn Ile Pro Ser Lys Glu Pro Lys Asp Gly Ser Pro Val
```

```
        860                 865                 870

caa cca agt ctc tta tcg tta atg aaa gat agg aga tta aca ttg gag      3172
Gln Pro Ser Leu Leu Ser Leu Met Lys Asp Arg Arg Leu Thr Leu Glu
    875                 880                 885

caa gtg gta gcc ata gag gcc ctg act caa ctc tca gaa gcc cca tca      3220
Gln Val Val Ala Ile Glu Ala Leu Thr Gln Leu Ser Glu Ala Pro Ser
890                 895                 900                 905

gag aat tcc tcc cca tca aag tca gag aag gat gag gaa tca gag cag      3268
Glu Asn Ser Ser Pro Ser Lys Ser Glu Lys Asp Glu Glu Ser Glu Gln
                910                 915                 920

aga aca gcc agt ttg ctt aat agc tgc aaa gct atc ctc tac act gta      3316
Arg Thr Ala Ser Leu Leu Asn Ser Cys Lys Ala Ile Leu Tyr Thr Val
            925                 930                 935

aga aaa gac ctc caa gac cca aac tta cag gga gag cca cca aaa ctt      3364
Arg Lys Asp Leu Gln Asp Pro Asn Leu Gln Gly Glu Pro Pro Lys Leu
        940                 945                 950

aat cac tgt cca tct ttg gaa aaa caa agt tca tgc aac acg gtg gtt      3412
Asn His Cys Pro Ser Leu Glu Lys Gln Ser Ser Cys Asn Thr Val Val
    955                 960                 965

ttc aat ggg caa act act acc ctt tcc aac tca cat atc aac tca gct      3460
Phe Asn Gly Gln Thr Thr Thr Leu Ser Asn Ser His Ile Asn Ser Ala
970                 975                 980                 985

act aac caa gca tcc aca aag tca cat gaa tat tca aaa gtc aca  aat     3508
Thr Asn Gln Ala Ser Thr Lys Ser His Glu Tyr Ser Lys Val Thr  Asn
                990                 995                 1000

tca tta tct ctt  ttt ata cca aaa tca  aat tca tcc aag att  gac      3553
Ser Leu Ser Leu  Phe Ile Pro Lys Ser  Asn Ser Ser Lys Ile  Asp
            1005                 1010                 1015

acc aat aaa agt  att gct caa ggg ata  att act ctt gac aat  tgt      3598
Thr Asn Lys Ser  Ile Ala Gln Gly Ile  Ile Thr Leu Asp Asn  Cys
            1020                 1025                 1030

tcc aat gat ttg  cat cag ttg cca cca  aga aat aat gaa gtg  gag      3643
Ser Asn Asp Leu  His Gln Leu Pro Pro  Arg Asn Asn Glu Val  Glu
            1035                 1040                 1045

tat tgc aac cag  tta ctg gac agc agc  aaa aaa ttg gac tca  gat      3688
Tyr Cys Asn Gln  Leu Leu Asp Ser Ser  Lys Lys Leu Asp Ser  Asp
            1050                 1055                 1060

gat cta tca tgt  cag gat gca acc cat  acc caa att gag gaa  gat      3733
Asp Leu Ser Cys  Gln Asp Ala Thr His  Thr Gln Ile Glu Glu  Asp
            1065                 1070                 1075

gtt gca aca cag  ttg aca caa ctt gct  tcg ata att aag atc  aat      3778
Val Ala Thr Gln  Leu Thr Gln Leu Ala  Ser Ile Ile Lys Ile  Asn
            1080                 1085                 1090

tat ata aaa cca  gag gac aaa aaa gtt  gaa agt aca cca aca  agc      3823
Tyr Ile Lys Pro  Glu Asp Lys Lys Val  Glu Ser Thr Pro Thr  Ser
            1095                 1100                 1105

ctt gtc aca tgt  aat gta cag caa aaa  tac aat cag gag aag  ggc      3868
Leu Val Thr Cys  Asn Val Gln Gln Lys  Tyr Asn Gln Glu Lys  Gly
            1110                 1115                 1120

aca ata caa cag  aaa cca cct tca agt  gta cac aat aat cat  ggt      3913
Thr Ile Gln Gln  Lys Pro Pro Ser Ser  Val His Asn Asn His  Gly
            1125                 1130                 1135

tca tca tta aca  aaa caa aag aac cca  acc cag aaa aag aca  aaa      3958
Ser Ser Leu Thr  Lys Gln Lys Asn Pro  Thr Gln Lys Lys Thr  Lys
            1140                 1145                 1150

tcc acc cca tca  aga gat cgg cgg aaa  aag aag ccc aca gtt  gta      4003
Ser Thr Pro Ser  Arg Asp Arg Arg Lys  Lys Lys Pro Thr Val  Val
            1155                 1160                 1165

agt tat caa gaa  aat gat cgg cag aag  tgg gaa aag ttg tcc  tat      4048
```

```
Ser Tyr Gln Glu  Asn Asp Arg Gln Lys  Trp Glu Lys Leu Ser  Tyr
            1170                 1175                 1180

atg tat ggc aca  ata tgc gac att tgg  ata gca tcg aaa ttt  caa      4093
Met Tyr Gly Thr  Ile Cys Asp Ile Trp  Ile Ala Ser Lys Phe  Gln
            1185                 1190                 1195

aat ttt ggg caa  ttt tgt cca cat gat  ttt cct act gta ttt  ggg      4138
Asn Phe Gly Gln  Phe Cys Pro His Asp  Phe Pro Thr Val Phe  Gly
            1200                 1205                 1210

aaa att tct tcc  tcg acc aaa ata tgg  aaa cca ctg gct caa  acg      4183
Lys Ile Ser Ser  Ser Thr Lys Ile Trp  Lys Pro Leu Ala Gln  Thr
            1215                 1220                 1225

agg tcc att atg  caa ccc aaa aca gta  ttt cca cca ctc act  cag      4228
Arg Ser Ile Met  Gln Pro Lys Thr Val  Phe Pro Pro Leu Thr  Gln
            1230                 1235                 1240

ata aaa tta cag  aga tat cct gaa tca  gca gag gaa aag gtg  aag      4273
Ile Lys Leu Gln  Arg Tyr Pro Glu Ser  Ala Glu Glu Lys Val  Lys
            1245                 1250                 1255

gtt gaa cca ttg  gat tca ctc agc tta  ttt cat ctt aaa acg  gaa      4318
Val Glu Pro Leu  Asp Ser Leu Ser Leu  Phe His Leu Lys Thr  Glu
            1260                 1265                 1270

tcc aac ggg aag  gca ttc act gat aaa  gct tat aat tct cag  gta      4363
Ser Asn Gly Lys  Ala Phe Thr Asp Lys  Ala Tyr Asn Ser Gln  Val
            1275                 1280                 1285

cag tta acg gtg  aat gcc aat cag aaa  gcc cat cct ttg acc  cag      4408
Gln Leu Thr Val  Asn Ala Asn Gln Lys  Ala His Pro Leu Thr  Gln
            1290                 1295                 1300

ccc tcc tct cca  cct aac cag tgt gct  aac gtg atg gca ggc  gat      4453
Pro Ser Ser Pro  Pro Asn Gln Cys Ala  Asn Val Met Ala Gly  Asp
            1305                 1310                 1315

gac caa ata cgg  ttt cag cag gtt gtt  aag gag caa ctc atg  cat      4498
Asp Gln Ile Arg  Phe Gln Gln Val Val  Lys Glu Gln Leu Met  His
            1320                 1325                 1330

cag aga ctg cca  aca ttg cct ggt atc  tct cat gaa aca ccc  tta      4543
Gln Arg Leu Pro  Thr Leu Pro Gly Ile  Ser His Glu Thr Pro  Leu
            1335                 1340                 1345

ccg gag tca gca  cta act ctc agg aat  gta aat gta gtg tgt  tca      4588
Pro Glu Ser Ala  Leu Thr Leu Arg Asn  Val Asn Val Val Cys  Ser
            1350                 1355                 1360

ggt gga att aca  gtg gtt tct acc aaa  agt gaa gag gaa gtc  tgt      4633
Gly Gly Ile Thr  Val Val Ser Thr Lys  Ser Glu Glu Glu Val  Cys
            1365                 1370                 1375

tca tcc agt ttt  gga aca tca gaa ttt  tcc aca gtg gac agt  gca      4678
Ser Ser Ser Phe  Gly Thr Ser Glu Phe  Ser Thr Val Asp Ser  Ala
            1380                 1385                 1390

cag aaa aat ttt  aat gat tat gcc atg  aac ttc ttt act aac  cct      4723
Gln Lys Asn Phe  Asn Asp Tyr Ala Met  Asn Phe Phe Thr Asn  Pro
            1395                 1400                 1405

aca aaa aac cta  gtg tct ata act aaa  gat tct gaa ctg ccc  acc      4768
Thr Lys Asn Leu  Val Ser Ile Thr Lys  Asp Ser Glu Leu Pro  Thr
            1410                 1415                 1420

tgc agc tgt ctt  gat cga gtt ata caa  aaa gac aaa ggc cca  tat      4813
Cys Ser Cys Leu  Asp Arg Val Ile Gln  Lys Asp Lys Gly Pro  Tyr
            1425                 1430                 1435

tat aca cac ctt  ggg gca gga cca agt  gtt gct gct gtc agg  gaa      4858
Tyr Thr His Leu  Gly Ala Gly Pro Ser  Val Ala Ala Val Arg  Glu
            1440                 1445                 1450

atc atg gag aat  agg tat ggt caa aaa  gga aac gca ata agg  ata      4903
Ile Met Glu Asn  Arg Tyr Gly Gln Lys  Gly Asn Ala Ile Arg  Ile
            1455                 1460                 1465
```

-continued

```
gaa ata gta gtg  tac acc ggt aaa gaa  ggg aaa agc tct cat  ggg      4948
Glu Ile Val Val  Tyr Thr Gly Lys Glu  Gly Lys Ser Ser His  Gly
            1470                 1475                 1480

tgt cca att gct  aag tgg gtt tta aga  aga agc agt gat gaa  gaa      4993
Cys Pro Ile Ala  Lys Trp Val Leu Arg  Arg Ser Ser Asp Glu  Glu
            1485                 1490                 1495

aaa gtt ctt tgt  ttg gtc cgg cag cgt  aca ggc cac cac tgt  cca      5038
Lys Val Leu Cys  Leu Val Arg Gln Arg  Thr Gly His His Cys  Pro
            1500                 1505                 1510

act gct gtg atg  gtg gtg ctc atc atg  gtg tgg gat ggc atc  cct      5083
Thr Ala Val Met  Val Val Leu Ile Met  Val Trp Asp Gly Ile  Pro
            1515                 1520                 1525

ctt cca atg gcc  gac cgg cta tac aca  gag ctc aca gag aat  cta      5128
Leu Pro Met Ala  Asp Arg Leu Tyr Thr  Glu Leu Thr Glu Asn  Leu
            1530                 1535                 1540

aag tca tac aat  ggg cac cct acc gac  aga aga tgc acc ctc  aat      5173
Lys Ser Tyr Asn  Gly His Pro Thr Asp  Arg Arg Cys Thr Leu  Asn
            1545                 1550                 1555

gaa aat cgt acc  tgt aca tgt caa gga  att gat cca gag act  tgt      5218
Glu Asn Arg Thr  Cys Thr Cys Gln Gly  Ile Asp Pro Glu Thr  Cys
            1560                 1565                 1570

gga gct tca ttc  tct ttt ggc tgt tca  tgg agt atg tac ttt  aat      5263
Gly Ala Ser Phe  Ser Phe Gly Cys Ser  Trp Ser Met Tyr Phe  Asn
            1575                 1580                 1585

ggc tgt aag ttt  ggt aga agc cca agc  ccc aga aga ttt aga  att      5308
Gly Cys Lys Phe  Gly Arg Ser Pro Ser  Pro Arg Arg Phe Arg  Ile
            1590                 1595                 1600

gat cca agc tct  ccc tta cat gaa aaa  aac ctt gaa gat aac  tta      5353
Asp Pro Ser Ser  Pro Leu His Glu Lys  Asn Leu Glu Asp Asn  Leu
            1605                 1610                 1615

cag agt ttg gct  aca cga tta gct cca  att tat aag cag tat  gct      5398
Gln Ser Leu Ala  Thr Arg Leu Ala Pro  Ile Tyr Lys Gln Tyr  Ala
            1620                 1625                 1630

cca gta gct tac  caa aat cag gtg gaa  tat gaa aat gtt gcc  cga      5443
Pro Val Ala Tyr  Gln Asn Gln Val Glu  Tyr Glu Asn Val Ala  Arg
            1635                 1640                 1645

gaa tgt cgg ctt  ggc agc aag gaa ggt  cgt ccc ttc tct ggg  gtc      5488
Glu Cys Arg Leu  Gly Ser Lys Glu Gly  Arg Pro Phe Ser Gly  Val
            1650                 1655                 1660

act gct tgc ctg  gac ttc tgt gct cat  ccc cac agg gac att  cac      5533
Thr Ala Cys Leu  Asp Phe Cys Ala His  Pro His Arg Asp Ile  His
            1665                 1670                 1675

aac atg aat aat  gga agc act gtg gtt  tgt acc tta act cga  gaa      5578
Asn Met Asn Asn  Gly Ser Thr Val Val  Cys Thr Leu Thr Arg  Glu
            1680                 1685                 1690

gat aac cgc tct  ttg ggt gtt att cct  caa gat gag cag ctc  cat      5623
Asp Asn Arg Ser  Leu Gly Val Ile Pro  Gln Asp Glu Gln Leu  His
            1695                 1700                 1705

gtg cta cct ctt  tat aag ctt tca gac  aca gat gag ttt ggc  tcc      5668
Val Leu Pro Leu  Tyr Lys Leu Ser Asp  Thr Asp Glu Phe Gly  Ser
            1710                 1715                 1720

aag gaa gga atg  gaa gcc aag atc aaa  tct ggg gcc atc gag  gtc      5713
Lys Glu Gly Met  Glu Ala Lys Ile Lys  Ser Gly Ala Ile Glu  Val
            1725                 1730                 1735

ctg gca ccc cgc  cgc aaa aaa aga acg  tgt ttc act cag cct  gtt      5758
Leu Ala Pro Arg  Arg Lys Lys Arg Thr  Cys Phe Thr Gln Pro  Val
            1740                 1745                 1750

ccc cgt tct gga  aag aag agg gct gcg  atg atg aca gag gtt  ctt      5803
Pro Arg Ser Gly  Lys Lys Arg Ala Ala  Met Met Thr Glu Val  Leu
            1755                 1760                 1765
```

```
gca cat aag ata  agg gca gtg gaa aag  aaa cct att ccc cga  atc      5848
Ala His Lys Ile  Arg Ala Val Glu Lys  Lys Pro Ile Pro Arg  Ile
            1770                 1775                 1780

aag cgg aag aat  aac tca aca aca aca  aac aac agt aag cct  tcg      5893
Lys Arg Lys Asn  Asn Ser Thr Thr Thr  Asn Asn Ser Lys Pro  Ser
            1785                 1790                 1795

tca ctg cca acc  tta ggg agt aac act  gag acc gtg caa cct  gaa      5938
Ser Leu Pro Thr  Leu Gly Ser Asn Thr  Glu Thr Val Gln Pro  Glu
            1800                 1805                 1810

gta aaa agt gaa  acc gaa ccc cat ttt  atc tta aaa agt tca  gac      5983
Val Lys Ser Glu  Thr Glu Pro His Phe  Ile Leu Lys Ser Ser  Asp
            1815                 1820                 1825

aac act aaa act  tat tcg ctg atg cca  tcc gct cct cac cca  gtg      6028
Asn Thr Lys Thr  Tyr Ser Leu Met Pro  Ser Ala Pro His Pro  Val
            1830                 1835                 1840

aaa gag gca tct  cca ggc ttc tcc tgg  tcc ccg aag act gct  tca      6073
Lys Glu Ala Ser  Pro Gly Phe Ser Trp  Ser Pro Lys Thr Ala  Ser
            1845                 1850                 1855

gcc aca cca gct  cca ctg aag aat gac  gca aca gcc tca tgc  ggg      6118
Ala Thr Pro Ala  Pro Leu Lys Asn Asp  Ala Thr Ala Ser Cys  Gly
            1860                 1865                 1870

ttt tca gaa aga  agc agc act ccc cac  tgt acg atg cct tcg  gga      6163
Phe Ser Glu Arg  Ser Ser Thr Pro His  Cys Thr Met Pro Ser  Gly
            1875                 1880                 1885

aga ctc agt ggt  gcc aat gca gct gct  gct gat ggc cct ggc  att      6208
Arg Leu Ser Gly  Ala Asn Ala Ala Ala  Ala Asp Gly Pro Gly  Ile
            1890                 1895                 1900

tca cag ctt ggc  gaa gtg gct cct ctc  ccc acc ctg tct gct  cct      6253
Ser Gln Leu Gly  Glu Val Ala Pro Leu  Pro Thr Leu Ser Ala  Pro
            1905                 1910                 1915

gtg atg gag ccc  ctc att aat tct gag  cct tcc act ggt gtg  act      6298
Val Met Glu Pro  Leu Ile Asn Ser Glu  Pro Ser Thr Gly Val  Thr
            1920                 1925                 1930

gag ccg cta acg  cct cat cag cca aac  cac cag ccc tcc ttc  ctc      6343
Glu Pro Leu Thr  Pro His Gln Pro Asn  His Gln Pro Ser Phe  Leu
            1935                 1940                 1945

acc tct cct caa  gac ctt gcc tct tct  cca atg gaa gaa gat  gag      6388
Thr Ser Pro Gln  Asp Leu Ala Ser Ser  Pro Met Glu Glu Asp  Glu
            1950                 1955                 1960

cag cat tct gaa  gca gat gag cct cca  tca gac gaa ccc cta  tct      6433
Gln His Ser Glu  Ala Asp Glu Pro Pro  Ser Asp Glu Pro Leu  Ser
            1965                 1970                 1975

gat gac ccc ctg  tca cct gct gag gag  aaa ttg ccc cac att  gat      6478
Asp Asp Pro Leu  Ser Pro Ala Glu Glu  Lys Leu Pro His Ile  Asp
            1980                 1985                 1990

gag tat tgg tca  gac agt gag cac atc  ttt ttg gat gca aat  att      6523
Glu Tyr Trp Ser  Asp Ser Glu His Ile  Phe Leu Asp Ala Asn  Ile
            1995                 2000                 2005

ggt ggg gtg gcc  atc gca cct gct cac  ggc tcg gtt ttg att  gag      6568
Gly Gly Val Ala  Ile Ala Pro Ala His  Gly Ser Val Leu Ile  Glu
            2010                 2015                 2020

tgt gcc cgg cga  gag ctg cac gct acc  act cct gtt gag cac  ccc      6613
Cys Ala Arg Arg  Glu Leu His Ala Thr  Thr Pro Val Glu His  Pro
            2025                 2030                 2035

aac cgt aat cat  cca acc cgc ctc tcc  ctt gtc ttt tac cag  cac      6658
Asn Arg Asn His  Pro Thr Arg Leu Ser  Leu Val Phe Tyr Gln  His
            2040                 2045                 2050

aaa aac cta aat  aag ccc caa cat ggt  ttt gaa cta aac aag  att      6703
Lys Asn Leu Asn  Lys Pro Gln His Gly  Phe Glu Leu Asn Lys  Ile
```

```
            2055                2060                2065

aag ttt gag gct  aaa gaa gct aag aat  aag aaa atg aag gcc  tca      6748
Lys Phe Glu Ala  Lys Glu Ala Lys Asn  Lys Lys Met Lys Ala  Ser
            2070                2075                2080

gag caa aaa gac  cag gca gct aat gaa  ggt cca gaa cag tcc  tct      6793
Glu Gln Lys Asp  Gln Ala Ala Asn Glu  Gly Pro Glu Gln Ser  Ser
            2085                2090                2095

gaa gta aat gaa  ttg aac caa att cct  tct cat aaa gca tta  aca      6838
Glu Val Asn Glu  Leu Asn Gln Ile Pro  Ser His Lys Ala Leu  Thr
            2100                2105                2110

tta acc cat gac  aat gtt gtc acc gtg  tcc cct tat gct ctc  aca      6883
Leu Thr His Asp  Asn Val Val Thr Val  Ser Pro Tyr Ala Leu  Thr
            2115                2120                2125

cac gtt gcg ggg  ccc tat aac cat tgg  gtc tga aggcttttct            6926
His Val Ala Gly  Pro Tyr Asn His Trp  Val
            2130                2135

cccctctta atgcctttgc tagtgcagtg tattttttca aggtgctgtt aaaagaaagt   6986

catgttgtcg tttactatct tcatctcacc catttcaagt ctgaggtaaa aaaataataa   7046

tgataacaaa acggggtggg tattcttaac tgtgactata ttttgacaat tggtagaagg   7106

tgcacatttt aagcaaaaat aaaagtttta tagttttaaa tacataaaga aatgtttcag   7166

ttaggcatta accttgatag aatcactcag tttggtgctt taaattaagt ctgtttacta   7226

tgaaacaaga gtcattttta gaggatttta acaggttcat gttctatgat gtaaaatcaa   7286

gacacacagt gttaactcta cacagcttct ggtgcttaac cacatccaca cagttaaaaa   7346

taagctgaat tattatttca tggtgccatt gttccaacat cttccaatca ttgctagaaa   7406

attggcatat tcctttgaaa taaacttatg aaatgttttc tctcttaaaa tatttctcct   7466

gtgtaaaata aatcattgtt gttagtaatg gttggaggct gttcataaat tgtaaatata   7526

tattttaaaa gcactttcta tttttaaaag taacttgaaa taatatagta taagaatcct   7586

attgtctatt gtttgtgcat atttgcatac aagagaaatc atttatcctt gctgtgtaga   7646

gttccatctt gttaactgca gtatgtattc taatcatgta tatggtttgt gttcttttac   7706

tgtgtcctct cacattcaag tattagcaac ttgcagtata taaaatagtt agataatgag   7766

aagttgttaa ttatctctaa aattggaatt aggaagcata tcaccaatac tgattaacat   7826

tctctttgga actaggtaag agtggtctct tcttattgaa caacctcaat ttagtttcat   7886

cccacctttc tcagtataat ccatgagagg tgtttccaaa aggagatgag ggaacaggat   7946

aggtttcaga agagtcaaat gcttctaatg tctcaaggtg ataaaaataca aaaactaagt  8006

agacagatat ttgtactgaa gtctgataca gaattagaaa aaaaaaattc ttgttgaaat   8066

attttgaaaa caaattccct actatcatca catgcctccc caaccccaag tcaaaaacaa   8126

gaggaatggt actacaaaca tggctttgtc cattaagagc taattcattt gtttatctta   8186

gcatactaga tttgggaaaa tgataactca tcttttctga taattgccta tgttctaggt   8246

aacaggaaaa caggcattaa gtttatttta gtcttcccat tttcttccta ttactttatt   8306

gactcatttt attgcaaaac aaaaaggatt acccaaacaa catgtttcga acaaggagaa   8366

ttttcaatga aatacttgat tctgttaaaa tgcagaggtg ctataacatt caaagtgtca   8426

gattccttgg gagtatggaa aacctaatgg tgcttctccc ttggaaatgc cataggaagc   8486

ccacaaccgc taacacttac aattttggtg caaaagcaaa cagttccagc aggctctcta   8546

aagaaaaact cattgtaact tattaaaata atatctggtg caaagtatct gttttgagct   8606

tttgactaat ccaagtaaag gaatatgaag ggattgtaaa aacaaaatg tccattgata    8666
```

```
gaccatcgtg tacaagtaga tttctgcttg ttgaatatgt aaaatagggt aattcattga   8726

cttgttttag tattttgtgt gccttagatt tccgttttaa gacatgtata tttttgtgag   8786

cctaaggttt cttatataca tataagtata taaataagtg attgtttatt gcttcagctg   8846

cttcaacaag atatttacta gtattagact atcaggaata cacccttgcg agattatgtt   8906

ttagatttta ggccttagct cccactagaa attatttctt caccagattt aatggataaa   8966

gttttatggc tctttatgca tccactcatc tactcattct tcgagtctac acttattgaa   9026

tgcctgcaaa atctaagtat cacttttatt tttctttgga tcaccaccta tgacatagta   9086

aacttgaaga ataaaaacta ccctcagaaa tatttttaaa agaagtagca aattatcttc   9146

agtataatcc atggtaatgt atgcagtaat tcaaattgat ctctctctca ataggtttct   9206

taacaatcta aacttgaaac atcaatgtta atttttggaa ctattgggat ttgtgacgct   9266

tgttgcagtt taccaaaaca agtatttgaa aatatatagt atcaactgaa atgtttccat   9326

tccgttgttg tagttaacat catgaatgga cttcttaagc tgattacccc actgtgggaa   9386

ccaaattgga ttcctacttt gttggactct ctttcctgat tttaacaatt taccatccca   9446

ttctctgccc tgtgattttt tttaaaagct tattcaatgt tctgcagcat tgtgattgta   9506

tgctggctac actgctttta gaatgctctt tctcatgaag caaggaaata aatttgtttg   9566

aaatgacatt ttctctcaaa aaaaaaaaaa aaaaa                              9601
```

<210> SEQ ID NO 2
<211> LENGTH: 2136
<212> TYPE: PRT
<213> ORGANISM: Homo sapiens

<400> SEQUENCE: 2

```
Met Ser Arg Ser Arg His Ala Arg Pro Ser Arg Leu Val Arg Lys Glu
1               5                   10                  15

Asp Val Asn Lys Lys Lys Lys Asn Ser Gln Leu Arg Lys Thr Thr Lys
            20                  25                  30

Gly Ala Asn Lys Asn Val Ala Ser Val Lys Thr Leu Ser Pro Gly Lys
        35                  40                  45

Leu Lys Gln Leu Ile Gln Glu Arg Asp Val Lys Lys Lys Thr Glu Pro
    50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95

Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
        115                 120                 125

Pro Leu Ser Lys Gly Leu Glu Lys Gln His Asp Cys Asp Tyr Lys Ile
    130                 135                 140

Leu Pro Ala Leu Gly Val Lys His Ser Glu Asn Asp Ser Val Pro Met
145                 150                 155                 160

Gln Asp Thr Gln Val Leu Pro Asp Ile Glu Thr Leu Ile Gly Val Gln
                165                 170                 175

Asn Pro Ser Leu Leu Lys Gly Lys Ser Gln Glu Thr Thr Gln Phe Trp
            180                 185                 190

Ser Gln Arg Val Glu Asp Ser Lys Ile Asn Ile Pro Thr His Ser Gly
        195                 200                 205
```

```
Pro Ala Ala Glu Ile Leu Pro Gly Pro Leu Glu Gly Thr Arg Cys Gly
    210                 215                 220

Glu Gly Leu Phe Ser Glu Glu Thr Leu Asn Asp Thr Ser Gly Ser Pro
225                 230                 235                 240

Lys Met Phe Ala Gln Asp Thr Val Cys Ala Pro Phe Pro Gln Arg Ala
                245                 250                 255

Thr Pro Lys Val Thr Ser Gln Gly Asn Pro Ser Ile Gln Leu Glu Glu
            260                 265                 270

Leu Gly Ser Arg Val Glu Ser Leu Lys Leu Ser Asp Ser Tyr Leu Asp
        275                 280                 285

Pro Ile Lys Ser Glu His Asp Cys Tyr Pro Thr Ser Ser Leu Asn Lys
    290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
                325                 330                 335

Ala Thr Leu Gly Ala Lys Pro Asp His Gln Glu Ala Phe Glu Ala Thr
            340                 345                 350

Ala Asn Gln Gln Glu Val Ser Asp Thr Thr Ser Phe Leu Gly Gln Ala
        355                 360                 365

Phe Gly Ala Ile Pro His Gln Trp Glu Leu Pro Gly Ala Asp Pro Val
    370                 375                 380

His Gly Glu Ala Leu Gly Glu Thr Pro Asp Leu Pro Glu Ile Pro Gly
385                 390                 395                 400

Ala Ile Pro Val Gln Gly Glu Val Phe Gly Thr Ile Leu Asp Gln Gln
                405                 410                 415

Glu Thr Leu Gly Met Ser Gly Ser Val Val Pro Asp Leu Pro Val Phe
            420                 425                 430

Leu Pro Val Pro Pro Asn Pro Ile Ala Thr Phe Asn Ala Pro Ser Lys
        435                 440                 445

Trp Pro Glu Pro Gln Ser Thr Val Ser Tyr Gly Leu Ala Val Gln Gly
    450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
                485                 490                 495

Val Glu Asn Glu Lys Gln Val His Ile Ser Phe Leu Pro Ala Asn Thr
            500                 505                 510

Gln Gly Phe Pro Leu Ala Pro Glu Arg Gly Leu Phe His Ala Ser Leu
        515                 520                 525

Gly Ile Ala Gln Leu Ser Gln Ala Gly Pro Ser Lys Ser Asp Arg Gly
    530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                565                 570                 575

Thr Thr Leu Leu Pro Thr Leu Glu Lys Lys Lys Arg Lys Arg Cys Gly
            580                 585                 590

Val Cys Glu Pro Cys Gln Gln Lys Thr Asn Cys Gly Glu Cys Thr Tyr
        595                 600                 605

Cys Lys Asn Arg Lys Asn Ser His Gln Ile Cys Lys Lys Arg Lys Cys
    610                 615                 620
```

```
Glu Glu Leu Lys Lys Lys Pro Ser Val Val Val Pro Leu Glu Val Ile
625                 630                 635                 640

Lys Glu Asn Lys Arg Pro Gln Arg Glu Lys Lys Pro Lys Val Leu Lys
                645                 650                 655

Ala Asp Phe Asp Asn Lys Pro Val Asn Gly Pro Lys Ser Glu Ser Met
            660                 665                 670

Asp Tyr Ser Arg Cys Gly His Gly Glu Glu Gln Lys Leu Glu Leu Asn
        675                 680                 685

Pro His Thr Val Glu Asn Val Thr Lys Asn Glu Asp Ser Met Thr Gly
    690                 695                 700

Ile Glu Val Glu Lys Trp Thr Gln Asn Lys Lys Ser Gln Leu Thr Asp
705                 710                 715                 720

His Val Lys Gly Asp Phe Ser Ala Asn Val Pro Glu Ala Glu Lys Ser
                725                 730                 735

Lys Asn Ser Glu Val Asp Lys Lys Arg Thr Lys Ser Pro Lys Leu Phe
            740                 745                 750

Val Gln Thr Val Arg Asn Gly Ile Lys His Val His Cys Leu Pro Ala
        755                 760                 765

Glu Thr Asn Val Ser Phe Lys Lys Phe Asn Ile Glu Glu Phe Gly Lys
    770                 775                 780

Thr Leu Glu Asn Asn Ser Tyr Lys Phe Leu Lys Asp Thr Ala Asn His
785                 790                 795                 800

Lys Asn Ala Met Ser Ser Val Ala Thr Asp Met Ser Cys Asp His Leu
                805                 810                 815

Lys Gly Arg Ser Asn Val Leu Val Phe Gln Gln Pro Gly Phe Asn Cys
            820                 825                 830

Ser Ser Ile Pro His Ser Ser His Ser Ile Ile Asn His His Ala Ser
        835                 840                 845

Ile His Asn Glu Gly Asp Gln Pro Lys Thr Pro Glu Asn Ile Pro Ser
    850                 855                 860

Lys Glu Pro Lys Asp Gly Ser Pro Val Gln Pro Ser Leu Leu Ser Leu
865                 870                 875                 880

Met Lys Asp Arg Arg Leu Thr Leu Glu Gln Val Val Ala Ile Glu Ala
                885                 890                 895

Leu Thr Gln Leu Ser Glu Ala Pro Ser Glu Asn Ser Ser Pro Ser Lys
            900                 905                 910

Ser Glu Lys Asp Glu Glu Ser Glu Gln Arg Thr Ala Ser Leu Leu Asn
        915                 920                 925

Ser Cys Lys Ala Ile Leu Tyr Thr Val Arg Lys Asp Leu Gln Asp Pro
    930                 935                 940

Asn Leu Gln Gly Glu Pro Pro Lys Leu Asn His Cys Pro Ser Leu Glu
945                 950                 955                 960

Lys Gln Ser Ser Cys Asn Thr Val Val Phe Asn Gly Gln Thr Thr Thr
                965                 970                 975

Leu Ser Asn Ser His Ile Asn Ser Ala Thr Asn Gln Ala Ser Thr Lys
            980                 985                 990

Ser His Glu Tyr Ser Lys Val Thr  Asn Ser Leu Ser Leu  Phe Ile Pro
        995                 1000                 1005

Lys Ser  Asn Ser Ser Lys Ile  Asp Thr Asn Lys Ser  Ile Ala Gln
    1010                 1015                 1020

Gly Ile  Ile Thr Leu Asp Asn  Cys Ser Asn Asp Leu  His Gln Leu
    1025                 1030                 1035

Pro Pro  Arg Asn Asn Glu Val  Glu Tyr Cys Asn Gln  Leu Leu Asp
```

```
    1040                1045                1050

Ser Ser  Lys Lys Leu Asp Ser  Asp Asp Leu Ser Cys  Gln Asp Ala
    1055                1060                1065

Thr His  Thr Gln Ile Glu Glu  Asp Val Ala Thr Gln  Leu Thr Gln
    1070                1075                1080

Leu Ala  Ser Ile Ile Lys Ile  Asn Tyr Ile Lys Pro  Glu Asp Lys
    1085                1090                1095

Lys Val  Glu Ser Thr Pro Thr  Ser Leu Val Thr Cys  Asn Val Gln
    1100                1105                1110

Gln Lys  Tyr Asn Gln Glu Lys  Gly Thr Ile Gln Gln  Lys Pro Pro
    1115                1120                1125

Ser Ser  Val His Asn Asn His  Gly Ser Ser Leu Thr  Lys Gln Lys
    1130                1135                1140

Asn Pro  Thr Gln Lys Lys Thr  Lys Ser Thr Pro Ser  Arg Asp Arg
    1145                1150                1155

Arg Lys  Lys Lys Pro Thr Val  Val Ser Tyr Gln Glu  Asn Asp Arg
    1160                1165                1170

Gln Lys  Trp Glu Lys Leu Ser  Tyr Met Tyr Gly Thr  Ile Cys Asp
    1175                1180                1185

Ile Trp  Ile Ala Ser Lys Phe  Gln Asn Phe Gly Gln  Phe Cys Pro
    1190                1195                1200

His Asp  Phe Pro Thr Val Phe  Gly Lys Ile Ser Ser  Ser Thr Lys
    1205                1210                1215

Ile Trp  Lys Pro Leu Ala Gln  Thr Arg Ser Ile Met  Gln Pro Lys
    1220                1225                1230

Thr Val  Phe Pro Pro Leu Thr  Gln Ile Lys Leu Gln  Arg Tyr Pro
    1235                1240                1245

Glu Ser  Ala Glu Glu Lys Val  Lys Val Glu Pro Leu  Asp Ser Leu
    1250                1255                1260

Ser Leu  Phe His Leu Lys Thr  Glu Ser Asn Gly Lys  Ala Phe Thr
    1265                1270                1275

Asp Lys  Ala Tyr Asn Ser Gln  Val Gln Leu Thr Val  Asn Ala Asn
    1280                1285                1290

Gln Lys  Ala His Pro Leu Thr  Gln Pro Ser Ser Pro  Pro Asn Gln
    1295                1300                1305

Cys Ala  Asn Val Met Ala Gly  Asp Asp Gln Ile Arg  Phe Gln Gln
    1310                1315                1320

Val Val  Lys Glu Gln Leu Met  His Gln Arg Leu Pro  Thr Leu Pro
    1325                1330                1335

Gly Ile  Ser His Glu Thr Pro  Leu Pro Glu Ser Ala  Leu Thr Leu
    1340                1345                1350

Arg Asn  Val Asn Val Val Cys  Ser Gly Gly Ile Thr  Val Val Ser
    1355                1360                1365

Thr Lys  Ser Glu Glu Glu Val  Cys Ser Ser Ser Phe  Gly Thr Ser
    1370                1375                1380

Glu Phe  Ser Thr Val Asp Ser  Ala Gln Lys Asn Phe  Asn Asp Tyr
    1385                1390                1395

Ala Met  Asn Phe Phe Thr Asn  Pro Thr Lys Asn Leu  Val Ser Ile
    1400                1405                1410

Thr Lys  Asp Ser Glu Leu Pro  Thr Cys Ser Cys Leu  Asp Arg Val
    1415                1420                1425

Ile Gln  Lys Asp Lys Gly Pro  Tyr Tyr Thr His Leu  Gly Ala Gly
    1430                1435                1440
```

```
Pro Ser  Val Ala Ala Val Arg  Glu Ile Met Glu Asn  Arg Tyr Gly
    1445                 1450                 1455

Gln Lys  Gly Asn Ala Ile Arg  Ile Glu Ile Val Val  Tyr Thr Gly
    1460                 1465                 1470

Lys Glu  Gly Lys Ser Ser His  Gly Cys Pro Ile Ala  Lys Trp Val
    1475                 1480                 1485

Leu Arg  Arg Ser Ser Asp Glu  Glu Lys Val Leu Cys  Leu Val Arg
    1490                 1495                 1500

Gln Arg  Thr Gly His His Cys  Pro Thr Ala Val Met  Val Val Leu
    1505                 1510                 1515

Ile Met  Val Trp Asp Gly Ile  Pro Leu Pro Met Ala  Asp Arg Leu
    1520                 1525                 1530

Tyr Thr  Glu Leu Thr Glu Asn  Leu Lys Ser Tyr Asn  Gly His Pro
    1535                 1540                 1545

Thr Asp  Arg Arg Cys Thr Leu  Asn Glu Asn Arg Thr  Cys Thr Cys
    1550                 1555                 1560

Gln Gly  Ile Asp Pro Glu Thr  Cys Gly Ala Ser Phe  Ser Phe Gly
    1565                 1570                 1575

Cys Ser  Trp Ser Met Tyr Phe  Asn Gly Cys Lys Phe  Gly Arg Ser
    1580                 1585                 1590

Pro Ser  Pro Arg Arg Phe Arg  Ile Asp Pro Ser Ser  Pro Leu His
    1595                 1600                 1605

Glu Lys  Asn Leu Glu Asp Asn  Leu Gln Ser Leu Ala  Thr Arg Leu
    1610                 1615                 1620

Ala Pro  Ile Tyr Lys Gln Tyr  Ala Pro Val Ala Tyr  Gln Asn Gln
    1625                 1630                 1635

Val Glu  Tyr Glu Asn Val Ala  Arg Glu Cys Arg Leu  Gly Ser Lys
    1640                 1645                 1650

Glu Gly  Arg Pro Phe Ser Gly  Val Thr Ala Cys Leu  Asp Phe Cys
    1655                 1660                 1665

Ala His  Pro His Arg Asp Ile  His Asn Met Asn Asn  Gly Ser Thr
    1670                 1675                 1680

Val Val  Cys Thr Leu Thr Arg  Glu Asp Asn Arg Ser  Leu Gly Val
    1685                 1690                 1695

Ile Pro  Gln Asp Glu Gln Leu  His Val Leu Pro Leu  Tyr Lys Leu
    1700                 1705                 1710

Ser Asp  Thr Asp Glu Phe Gly  Ser Lys Glu Gly Met  Glu Ala Lys
    1715                 1720                 1725

Ile Lys  Ser Gly Ala Ile Glu  Val Leu Ala Pro Arg  Arg Lys Lys
    1730                 1735                 1740

Arg Thr  Cys Phe Thr Gln Pro  Val Pro Arg Ser Gly  Lys Lys Arg
    1745                 1750                 1755

Ala Ala  Met Met Thr Glu Val  Leu Ala His Lys Ile  Arg Ala Val
    1760                 1765                 1770

Glu Lys  Lys Pro Ile Pro Arg  Ile Lys Arg Lys Asn  Asn Ser Thr
    1775                 1780                 1785

Thr Thr  Asn Asn Ser Lys Pro  Ser Ser Leu Pro Thr  Leu Gly Ser
    1790                 1795                 1800

Asn Thr  Glu Thr Val Gln Pro  Glu Val Lys Ser Glu  Thr Glu Pro
    1805                 1810                 1815

His Phe  Ile Leu Lys Ser Ser  Asp Asn Thr Lys Thr  Tyr Ser Leu
    1820                 1825                 1830
```

```
Met Pro  Ser Ala Pro His Pro  Val Lys Glu Ala Ser  Pro Gly Phe
    1835                 1840                 1845

Ser Trp  Ser Pro Lys Thr Ala  Ser Ala Thr Pro Ala  Pro Leu Lys
    1850                 1855                 1860

Asn Asp  Ala Thr Ala Ser Cys  Gly Phe Ser Glu Arg  Ser Ser Thr
    1865                 1870                 1875

Pro His  Cys Thr Met Pro Ser  Gly Arg Leu Ser Gly  Ala Asn Ala
    1880                 1885                 1890

Ala Ala  Ala Asp Gly Pro Gly  Ile Ser Gln Leu Gly  Glu Val Ala
    1895                 1900                 1905

Pro Leu  Pro Thr Leu Ser Ala  Pro Val Met Glu Pro  Leu Ile Asn
    1910                 1915                 1920

Ser Glu  Pro Ser Thr Gly Val  Thr Glu Pro Leu Thr  Pro His Gln
    1925                 1930                 1935

Pro Asn  His Gln Pro Ser Phe  Leu Thr Ser Pro Gln  Asp Leu Ala
    1940                 1945                 1950

Ser Ser  Pro Met Glu Glu Asp  Glu Gln His Ser Glu  Ala Asp Glu
    1955                 1960                 1965

Pro Pro  Ser Asp Glu Pro Leu  Ser Asp Asp Pro Leu  Ser Pro Ala
    1970                 1975                 1980

Glu Glu  Lys Leu Pro His Ile  Asp Glu Tyr Trp Ser  Asp Ser Glu
    1985                 1990                 1995

His Ile  Phe Leu Asp Ala Asn  Ile Gly Gly Val Ala  Ile Ala Pro
    2000                 2005                 2010

Ala His  Gly Ser Val Leu Ile  Glu Cys Ala Arg Arg  Glu Leu His
    2015                 2020                 2025

Ala Thr  Thr Pro Val Glu His  Pro Asn Arg Asn His  Pro Thr Arg
    2030                 2035                 2040

Leu Ser  Leu Val Phe Tyr Gln  His Lys Asn Leu Asn  Lys Pro Gln
    2045                 2050                 2055

His Gly  Phe Glu Leu Asn Lys  Ile Lys Phe Glu Ala  Lys Glu Ala
    2060                 2065                 2070

Lys Asn  Lys Lys Met Lys Ala  Ser Glu Gln Lys Asp  Gln Ala Ala
    2075                 2080                 2085

Asn Glu  Gly Pro Glu Gln Ser  Ser Glu Val Asn Glu  Leu Asn Gln
    2090                 2095                 2100

Ile Pro  Ser His Lys Ala Leu  Thr Leu Thr His Asp  Asn Val Val
    2105                 2110                 2115

Thr Val  Ser Pro Tyr Ala Leu  Thr His Val Ala Gly  Pro Tyr Asn
    2120                 2125                 2130

His Trp  Val
    2135

<210> SEQ ID NO 3
<211> LENGTH: 6498
<212> TYPE: DNA
<213> ORGANISM: Homo sapiens
<220> FEATURE:
<221> NAME/KEY: CDS
<222> LOCATION: (1)..(6498)

<400> SEQUENCE: 3

atg tct cga tcc cgc cat gca agg cct tcc aga tta gtc agg aag gaa       48
Met Ser Arg Ser Arg His Ala Arg Pro Ser Arg Leu Val Arg Lys Glu
1               5                   10                  15

gat gta aac aaa aaa aag aaa aac agc caa cta cga aag aca acc aag       96
```

```
Asp Val Asn Lys Lys Lys Lys Asn Ser Gln Leu Arg Lys Thr Thr Lys
            20                  25                  30

gga gcc aac aaa aat gtg gca tca gtc aag act tta agc cct gga aaa      144
Gly Ala Asn Lys Asn Val Ala Ser Val Lys Thr Leu Ser Pro Gly Lys
        35                  40                  45

tta aag caa tta att caa gaa aga gat gtt aag aaa aaa aca gaa cct      192
Leu Lys Gln Leu Ile Gln Glu Arg Asp Val Lys Lys Lys Thr Glu Pro
    50                  55                  60

aaa cca ccc gtg cca gtc aga agc ctt ctg aca aga gct gga gca gca      240
Lys Pro Pro Val Pro Val Arg Ser Leu Leu Thr Arg Ala Gly Ala Ala
65                  70                  75                  80

cgc atg aat ttg gat agg act gag gtt ctt ttt cag aac cca gag tcc      288
Arg Met Asn Leu Asp Arg Thr Glu Val Leu Phe Gln Asn Pro Glu Ser
                85                  90                  95

tta acc tgc aat ggg ttt aca atg gcg cta cga agc acc tct ctt agc      336
Leu Thr Cys Asn Gly Phe Thr Met Ala Leu Arg Ser Thr Ser Leu Ser
            100                 105                 110

agg cga ctc tcc caa ccc cca ctg gtc gta gcc aaa tcc aaa aag gtt      384
Arg Arg Leu Ser Gln Pro Pro Leu Val Val Ala Lys Ser Lys Lys Val
        115                 120                 125

cca ctt tct aag ggt tta gaa aag caa cat gat tgt gat tat aag ata      432
Pro Leu Ser Lys Gly Leu Glu Lys Gln His Asp Cys Asp Tyr Lys Ile
    130                 135                 140

ctc cct gct ttg gga gta aag cac tca gaa aat gat tcg gtt cca atg      480
Leu Pro Ala Leu Gly Val Lys His Ser Glu Asn Asp Ser Val Pro Met
145                 150                 155                 160

caa ggc acc caa gtc ctt cct gat ata gag act cta att ggt gta caa      528
Gln Gly Thr Gln Val Leu Pro Asp Ile Glu Thr Leu Ile Gly Val Gln
                165                 170                 175

aat ccc tct tta ctt aaa ggt aag agc caa gag aca act cag ttt tgg      576
Asn Pro Ser Leu Leu Lys Gly Lys Ser Gln Glu Thr Thr Gln Phe Trp
            180                 185                 190

tcc caa aga gtt gag gat tcc aag atc aat atc cct acc cac agt ggc      624
Ser Gln Arg Val Glu Asp Ser Lys Ile Asn Ile Pro Thr His Ser Gly
        195                 200                 205

cct gca gct gag atc ctt cct ggg cca ctg gaa ggg aca cgc tgt ggt      672
Pro Ala Ala Glu Ile Leu Pro Gly Pro Leu Glu Gly Thr Arg Cys Gly
    210                 215                 220

gaa gga cta ttc tct gaa gag aca ttg aat gat acc agt ggt tcc cca      720
Glu Gly Leu Phe Ser Glu Glu Thr Leu Asn Asp Thr Ser Gly Ser Pro
225                 230                 235                 240

aaa atg ttt gct cag gac aca gtg tgt gct cct ttt ccc caa aga gca      768
Lys Met Phe Ala Gln Asp Thr Val Cys Ala Pro Phe Pro Gln Arg Ala
                245                 250                 255

acc ccc aaa gtt acc tct caa gga aac ccc agc att cag tta gaa gag      816
Thr Pro Lys Val Thr Ser Gln Gly Asn Pro Ser Ile Gln Leu Glu Glu
            260                 265                 270

ttg ggt tca cga gta gaa tct ctt aag tta tct gat tct tac ctg gat      864
Leu Gly Ser Arg Val Glu Ser Leu Lys Leu Ser Asp Ser Tyr Leu Asp
        275                 280                 285

ccc att aaa agt gaa cat gat tgc tac ccc acc tcc agt ctt aat aag      912
Pro Ile Lys Ser Glu His Asp Cys Tyr Pro Thr Ser Ser Leu Asn Lys
    290                 295                 300

gtt ata cct gac ttg aac ctt aga aac tgc ttg gct ctt ggt ggg tct      960
Val Ile Pro Asp Leu Asn Leu Arg Asn Cys Leu Ala Leu Gly Gly Ser
305                 310                 315                 320

acg tct cct acc tct gta ata aaa ttc ctc ttg gca ggc tca aaa caa     1008
Thr Ser Pro Thr Ser Val Ile Lys Phe Leu Leu Ala Gly Ser Lys Gln
                325                 330                 335
```

```
gcg acc ctt ggt gct aaa cca gat cat caa gag gcc ttc gaa gct act      1056
Ala Thr Leu Gly Ala Lys Pro Asp His Gln Glu Ala Phe Glu Ala Thr
            340                 345                 350

gca aat caa cag gaa gtt tct gat acc acc tct ttc cta gga cag gcc      1104
Ala Asn Gln Gln Glu Val Ser Asp Thr Thr Ser Phe Leu Gly Gln Ala
        355                 360                 365

ttt ggt gct atc cca cat caa tgg gaa ctt cct ggt gct gac cca gtt      1152
Phe Gly Ala Ile Pro His Gln Trp Glu Leu Pro Gly Ala Asp Pro Val
    370                 375                 380

cat ggt gag gcc ctg ggt gag acc cca gat cta cca gag att cct ggt      1200
His Gly Glu Ala Leu Gly Glu Thr Pro Asp Leu Pro Glu Ile Pro Gly
385                 390                 395                 400

gct att cca gtc caa gga gag gtc ttt ggt act att tta gac caa caa      1248
Ala Ile Pro Val Gln Gly Glu Val Phe Gly Thr Ile Leu Asp Gln Gln
                405                 410                 415

gaa act ctt ggt atg agt ggg agt gtt gtc cca gac ttg cct gtc ttc      1296
Glu Thr Leu Gly Met Ser Gly Ser Val Val Pro Asp Leu Pro Val Phe
            420                 425                 430

ctt cct gtt cct cca aat cca att gct acc ttt aat gct cct tcc aaa      1344
Leu Pro Val Pro Pro Asn Pro Ile Ala Thr Phe Asn Ala Pro Ser Lys
        435                 440                 445

tgg cct gag ccc caa agc act gtc tca tat gga ctt gca gtc cag ggt      1392
Trp Pro Glu Pro Gln Ser Thr Val Ser Tyr Gly Leu Ala Val Gln Gly
    450                 455                 460

gct ata cag att ttg cct ttg ggc tca gga cac act cct caa tca tca      1440
Ala Ile Gln Ile Leu Pro Leu Gly Ser Gly His Thr Pro Gln Ser Ser
465                 470                 475                 480

tca aac tca gag aaa aat tca tta cct cca gta atg gct ata agc aat      1488
Ser Asn Ser Glu Lys Asn Ser Leu Pro Pro Val Met Ala Ile Ser Asn
                485                 490                 495

gta gaa aat gag aag cag gtt cat ata agc ttc ctg cca gct aac act      1536
Val Glu Asn Glu Lys Gln Val His Ile Ser Phe Leu Pro Ala Asn Thr
            500                 505                 510

cag ggg ttc cca tta gcc cct gag aga gga ctc ttc cat gct tca ctg      1584
Gln Gly Phe Pro Leu Ala Pro Glu Arg Gly Leu Phe His Ala Ser Leu
        515                 520                 525

ggt ata gcc caa ctc tct cag gct ggt cct agc aaa tca gac aga ggg      1632
Gly Ile Ala Gln Leu Ser Gln Ala Gly Pro Ser Lys Ser Asp Arg Gly
    530                 535                 540

agc tcc cag gtc agt gta acc agc aca gtt cat gtt gtc aac acc aca      1680
Ser Ser Gln Val Ser Val Thr Ser Thr Val His Val Val Asn Thr Thr
545                 550                 555                 560

gtg gtg act atg cca gtg cca atg gtc agt acc tcc tct tct tcc tat      1728
Val Val Thr Met Pro Val Pro Met Val Ser Thr Ser Ser Ser Ser Tyr
                565                 570                 575

acc act ttg cta ccg act ttg gaa aag aag aaa aga aag cga tgt ggg      1776
Thr Thr Leu Leu Pro Thr Leu Glu Lys Lys Lys Arg Lys Arg Cys Gly
            580                 585                 590

gtc tgt gaa ccc tgc cag cag aag acc aac tgt ggt gaa tgc act tac      1824
Val Cys Glu Pro Cys Gln Gln Lys Thr Asn Cys Gly Glu Cys Thr Tyr
        595                 600                 605

tgc aag aac aga aag aac agc cat cag atc tgt aag aaa aga aaa tgt      1872
Cys Lys Asn Arg Lys Asn Ser His Gln Ile Cys Lys Lys Arg Lys Cys
    610                 615                 620

gag gag ctg aaa aag aaa cca tct gtt gtt gtg cct ctg gag gtt ata      1920
Glu Glu Leu Lys Lys Lys Pro Ser Val Val Val Pro Leu Glu Val Ile
625                 630                 635                 640

aag gaa aac aag agg ccc cag agg gaa aag aag ccc aaa gtt tta aag      1968
Lys Glu Asn Lys Arg Pro Gln Arg Glu Lys Lys Pro Lys Val Leu Lys
                645                 650                 655
```

```
gca gat ttt gac aac aaa cca gta aat ggc ccc aag tca gaa tcc atg     2016
Ala Asp Phe Asp Asn Lys Pro Val Asn Gly Pro Lys Ser Glu Ser Met
            660                 665                 670

gac tac agt aga tgt ggt cat ggg gaa gaa caa aaa ttg gaa ttg aac     2064
Asp Tyr Ser Arg Cys Gly His Gly Glu Glu Gln Lys Leu Glu Leu Asn
        675                 680                 685

cca cat act gtt gaa aat gta act aaa aat gaa gac agc atg aca ggc     2112
Pro His Thr Val Glu Asn Val Thr Lys Asn Glu Asp Ser Met Thr Gly
    690                 695                 700

atc gag gtg gag aag tgg aca caa aac aag aaa tca cag tta act gat     2160
Ile Glu Val Glu Lys Trp Thr Gln Asn Lys Lys Ser Gln Leu Thr Asp
705                 710                 715                 720

cac gtg aaa gga gat ttt agt gct aat gtc cca gaa gct gaa aaa tcg     2208
His Val Lys Gly Asp Phe Ser Ala Asn Val Pro Glu Ala Glu Lys Ser
                725                 730                 735

aaa aac tct gaa gtt gac aag aaa cga acc aaa tct cca aaa ttg ttt     2256
Lys Asn Ser Glu Val Asp Lys Lys Arg Thr Lys Ser Pro Lys Leu Phe
            740                 745                 750

gta caa acc gta aga aat ggc att aaa cat gta cac tgt tta cca gct     2304
Val Gln Thr Val Arg Asn Gly Ile Lys His Val His Cys Leu Pro Ala
        755                 760                 765

gaa aca aat gtt tca ttt aaa aaa ttc aat att gaa gaa ttc ggc aag     2352
Glu Thr Asn Val Ser Phe Lys Lys Phe Asn Ile Glu Glu Phe Gly Lys
    770                 775                 780

aca ttg gaa aac aat tct tat aaa ttc cta aaa gac act gca aac cat     2400
Thr Leu Glu Asn Asn Ser Tyr Lys Phe Leu Lys Asp Thr Ala Asn His
785                 790                 795                 800

aaa aac gct atg agc tct gtt gct act gat atg agt tgt gat cat ctc     2448
Lys Asn Ala Met Ser Ser Val Ala Thr Asp Met Ser Cys Asp His Leu
                805                 810                 815

aag ggg aga agt aac gtt tta gta ttc cag cag cct ggc ttt aac tgc     2496
Lys Gly Arg Ser Asn Val Leu Val Phe Gln Gln Pro Gly Phe Asn Cys
            820                 825                 830

agt tcc att cca cat tct tca cac tcc atc ata aat cat cat gct agt     2544
Ser Ser Ile Pro His Ser Ser His Ser Ile Ile Asn His His Ala Ser
        835                 840                 845

ata cac aat gaa ggt gat caa cca aaa act cct gag aat ata cca agt     2592
Ile His Asn Glu Gly Asp Gln Pro Lys Thr Pro Glu Asn Ile Pro Ser
    850                 855                 860

aaa gaa cca aaa gat gga tct ccc gtt caa cca agt ctc tta tcg tta     2640
Lys Glu Pro Lys Asp Gly Ser Pro Val Gln Pro Ser Leu Leu Ser Leu
865                 870                 875                 880

atg aaa gat agg aga tta aca ttg gag caa gtg gta gcc ata gag gcc     2688
Met Lys Asp Arg Arg Leu Thr Leu Glu Gln Val Val Ala Ile Glu Ala
                885                 890                 895

ctg act caa ctc tca gaa gcc cca tca gag aat tcc tcc cca tca aag     2736
Leu Thr Gln Leu Ser Glu Ala Pro Ser Glu Asn Ser Ser Pro Ser Lys
            900                 905                 910

tca gag aag gat gag gaa tca gag cag aga aca gcc agt ttg ctt aat     2784
Ser Glu Lys Asp Glu Glu Ser Glu Gln Arg Thr Ala Ser Leu Leu Asn
        915                 920                 925

agc tgc aaa gct atc ctc tac act gta aga aaa gac ctc caa gac cca     2832
Ser Cys Lys Ala Ile Leu Tyr Thr Val Arg Lys Asp Leu Gln Asp Pro
    930                 935                 940

aac tta cag gga gag cca cca aaa ctt aat cac tgt cca tct ttg gaa     2880
Asn Leu Gln Gly Glu Pro Pro Lys Leu Asn His Cys Pro Ser Leu Glu
945                 950                 955                 960

aaa caa agt tca tgc aac acg gtg gtt ttc aat ggg caa act act acc     2928
Lys Gln Ser Ser Cys Asn Thr Val Val Phe Asn Gly Gln Thr Thr Thr
```

```
            965                 970                 975

ctt tcc aac tca cat atc aac tca gct act aac caa gca tcc aca aag      2976
Leu Ser Asn Ser His Ile Asn Ser Ala Thr Asn Gln Ala Ser Thr Lys
        980                 985                 990

tca cat gaa tat tca aaa gtc aca  aat tca tta tct ctt  ttt ata cca    3024
Ser His Glu Tyr Ser Lys Val Thr  Asn Ser Leu Ser Leu  Phe Ile Pro
    995                 1000                1005

aaa tca  aat tca tcc aag att  gac acc aat aaa agt  att gct caa      3069
Lys Ser  Asn Ser Ser Lys Ile  Asp Thr Asn Lys Ser  Ile Ala Gln
    1010                1015                1020

ggg ata  att act ctt gac aat  tgt tcc aat gat ttg  cat cag ttg      3114
Gly Ile  Ile Thr Leu Asp Asn  Cys Ser Asn Asp Leu  His Gln Leu
    1025                1030                1035

cca cca  aga aat aat gaa gtg  gag tat tgc aac cag  tta ctg gac      3159
Pro Pro  Arg Asn Asn Glu Val  Glu Tyr Cys Asn Gln  Leu Leu Asp
    1040                1045                1050

agc agc  aaa aaa ttg gac tca  gat gat cta tca tgt  cag gat gca      3204
Ser Ser  Lys Lys Leu Asp Ser  Asp Asp Leu Ser Cys  Gln Asp Ala
    1055                1060                1065

acc cat  acc caa att gag gaa  gat gtt gca aca cag  ttg aca caa      3249
Thr His  Thr Gln Ile Glu Glu  Asp Val Ala Thr Gln  Leu Thr Gln
    1070                1075                1080

ctt gct  tcg ata att aag atc  aat tat ata aaa cca  gag gac aaa      3294
Leu Ala  Ser Ile Ile Lys Ile  Asn Tyr Ile Lys Pro  Glu Asp Lys
    1085                1090                1095

aaa gtt  gaa agt aca cca aca  agc ctt gtc aca tgt  aat gta cag      3339
Lys Val  Glu Ser Thr Pro Thr  Ser Leu Val Thr Cys  Asn Val Gln
    1100                1105                1110

caa aaa  tac aat cag gag aag  ggc aca atg caa cag  aaa cca cct      3384
Gln Lys  Tyr Asn Gln Glu Lys  Gly Thr Met Gln Gln  Lys Pro Pro
    1115                1120                1125

tca agt  gta cac aat aat cat  ggt tca tca tta aca  aaa caa aag      3429
Ser Ser  Val His Asn Asn His  Gly Ser Ser Leu Thr  Lys Gln Lys
    1130                1135                1140

aac cca  acc cag aaa aag aca  aaa tcc acc cca tca  aga gat cgg      3474
Asn Pro  Thr Gln Lys Lys Thr  Lys Ser Thr Pro Ser  Arg Asp Arg
    1145                1150                1155

cgg aaa  aag aag ccc aca gtt  gta agt tat caa gaa  aat gat cgg      3519
Arg Lys  Lys Lys Pro Thr Val  Val Ser Tyr Gln Glu  Asn Asp Arg
    1160                1165                1170

cag aag  tgg gaa aag ttg tcc  tat atg tat ggc aca  ata tgc gac      3564
Gln Lys  Trp Glu Lys Leu Ser  Tyr Met Tyr Gly Thr  Ile Cys Asp
    1175                1180                1185

att tgg  ata gca tcg aaa ttt  caa aat ttt ggg caa  ttt tgt cca      3609
Ile Trp  Ile Ala Ser Lys Phe  Gln Asn Phe Gly Gln  Phe Cys Pro
    1190                1195                1200

cat gat  ttt cct act gta ttt  ggg aaa att tct tcc  tcg acc aaa      3654
His Asp  Phe Pro Thr Val Phe  Gly Lys Ile Ser Ser  Ser Thr Lys
    1205                1210                1215

ata tgg  aaa cca ctg gct caa  acg agg tcc att atg  caa ccc aaa      3699
Ile Trp  Lys Pro Leu Ala Gln  Thr Arg Ser Ile Met  Gln Pro Lys
    1220                1225                1230

aca gta  ttt cca cca ctc act  cag ata aaa tta cag  aga tat cct      3744
Thr Val  Phe Pro Pro Leu Thr  Gln Ile Lys Leu Gln  Arg Tyr Pro
    1235                1240                1245

gaa tca  gca gag gaa aag gtg  aag gtt gaa cca ttg  gat tca ctc      3789
Glu Ser  Ala Glu Glu Lys Val  Lys Val Glu Pro Leu  Asp Ser Leu
    1250                1255                1260

agc tta  ttt cat ctt aaa acg  gaa tcc aac ggg aag  gca ttc act      3834
```

```
Ser Leu  Phe His Leu Lys Thr  Glu Ser Asn Gly Lys  Ala Phe Thr
    1265                 1270                 1275

gat aaa  gct tat aat tct cag  gta cag tta acg gtg  aat gcc aat      3879
Asp Lys  Ala Tyr Asn Ser Gln  Val Gln Leu Thr Val  Asn Ala Asn
    1280                 1285                 1290

cag aaa  gcc cat cct ttg acc  cag ccc tcc tct cca  cct aac cag      3924
Gln Lys  Ala His Pro Leu Thr  Gln Pro Ser Ser Pro  Pro Asn Gln
    1295                 1300                 1305

tgt gct  aac gtg atg gca ggc  gat gac caa ata cgg  ttt cag cag      3969
Cys Ala  Asn Val Met Ala Gly  Asp Asp Gln Ile Arg  Phe Gln Gln
    1310                 1315                 1320

gtt gtt  aag gag caa ctc atg  cat cag aga ctg cca  aca ttg cct      4014
Val Val  Lys Glu Gln Leu Met  His Gln Arg Leu Pro  Thr Leu Pro
    1325                 1330                 1335

ggt atc  tct cat gaa aca ccc  tta ccg gag tca gca  cta act ctc      4059
Gly Ile  Ser His Glu Thr Pro  Leu Pro Glu Ser Ala  Leu Thr Leu
    1340                 1345                 1350

agg aat  gta aat gta gtg tgt  tca ggt gga att aca  gtg gtt tct      4104
Arg Asn  Val Asn Val Val Cys  Ser Gly Gly Ile Thr  Val Val Ser
    1355                 1360                 1365

acc aaa  agt gaa gag gaa gtc  tgt tca tcc agt ttt  gga aca tca      4149
Thr Lys  Ser Glu Glu Glu Val  Cys Ser Ser Ser Phe  Gly Thr Ser
    1370                 1375                 1380

gaa ttt  tcc aca gtg gac agt  gca cag aaa aat ttt  aat gat tat      4194
Glu Phe  Ser Thr Val Asp Ser  Ala Gln Lys Asn Phe  Asn Asp Tyr
    1385                 1390                 1395

gcc atg  aac ttc ttt act aac  cct aca aaa aac cta  gtg tct ata      4239
Ala Met  Asn Phe Phe Thr Asn  Pro Thr Lys Asn Leu  Val Ser Ile
    1400                 1405                 1410

act aaa  gat tct gaa ctg ccc  acc tgc agc tgt ctt  gat cga gtt      4284
Thr Lys  Asp Ser Glu Leu Pro  Thr Cys Ser Cys Leu  Asp Arg Val
    1415                 1420                 1425

ata caa  aaa gac aaa ggc cca  tat tat aca cac ctt  ggg gca gga      4329
Ile Gln  Lys Asp Lys Gly Pro  Tyr Tyr Thr His Leu  Gly Ala Gly
    1430                 1435                 1440

cca agt  gtt gct gct gtc agg  gaa atc atg gag aat  agg tat ggt      4374
Pro Ser  Val Ala Ala Val Arg  Glu Ile Met Glu Asn  Arg Tyr Gly
    1445                 1450                 1455

caa aaa  gga aac gca ata agg  ata gaa ata gta gtg  tac acc ggt      4419
Gln Lys  Gly Asn Ala Ile Arg  Ile Glu Ile Val Val  Tyr Thr Gly
    1460                 1465                 1470

aaa gaa  ggg aaa agc tct cat  ggg tgt cca att gct  aag tgg gtt      4464
Lys Glu  Gly Lys Ser Ser His  Gly Cys Pro Ile Ala  Lys Trp Val
    1475                 1480                 1485

tta aga  aga agc agt gat gaa  gaa aaa gtt ctt tgt  ttg gtc cgg      4509
Leu Arg  Arg Ser Ser Asp Glu  Glu Lys Val Leu Cys  Leu Val Arg
    1490                 1495                 1500

cag cgt  aca ggc cac cac tgt  cca act gct gtg atg  gtg gtg ctc      4554
Gln Arg  Thr Gly His His Cys  Pro Thr Ala Val Met  Val Val Leu
    1505                 1510                 1515

atc atg  gtg tgg gat ggc atc  cct ctt cca atg gcc  gac cgg cta      4599
Ile Met  Val Trp Asp Gly Ile  Pro Leu Pro Met Ala  Asp Arg Leu
    1520                 1525                 1530

tac aca  gag ctc aca gag aat  cta aag tca tac aat  ggg cac cct      4644
Tyr Thr  Glu Leu Thr Glu Asn  Leu Lys Ser Tyr Asn  Gly His Pro
    1535                 1540                 1545

acc gac  aga aga tgc acc ctc  aat gaa aat cgt acc  tgt aca tgt      4689
Thr Asp  Arg Arg Cys Thr Leu  Asn Glu Asn Arg Thr  Cys Thr Cys
    1550                 1555                 1560
```

```
caa gga  att gat cca gag act  tgt gga gct tca ttc  tct ttt ggc      4734
Gln Gly  Ile Asp Pro Glu Thr  Cys Gly Ala Ser Phe  Ser Phe Gly
    1565                 1570                 1575

tgt tca  tgg agt atg tac ttt  aat ggc tgt aag ttt  ggt aga agc      4779
Cys Ser  Trp Ser Met Tyr Phe  Asn Gly Cys Lys Phe  Gly Arg Ser
    1580                 1585                 1590

cca agc  ccc aga aga ttt aga  att gat cca agc tct  ccc tta cat      4824
Pro Ser  Pro Arg Arg Phe Arg  Ile Asp Pro Ser Ser  Pro Leu His
    1595                 1600                 1605

acc tac  tat gaa aga att act  aaa gga cgt aat cca  gaa aga aga      4869
Thr Tyr  Tyr Glu Arg Ile Thr  Lys Gly Arg Asn Pro  Glu Arg Arg
    1610                 1615                 1620

tat atg  aaa ccg gaa cga atc  agt ccg gga cac gag  gcc atg gaa      4914
Tyr Met  Lys Pro Glu Arg Ile  Ser Pro Gly His Glu  Ala Met Glu
    1625                 1630                 1635

aaa aac  ctt gaa gat aac tta  cag agt ttg gct aca  cga tta gct      4959
Lys Asn  Leu Glu Asp Asn Leu  Gln Ser Leu Ala Thr  Arg Leu Ala
    1640                 1645                 1650

cca att  tat aag cag tat gct  cca gta gct tac caa  aat cag gtg      5004
Pro Ile  Tyr Lys Gln Tyr Ala  Pro Val Ala Tyr Gln  Asn Gln Val
    1655                 1660                 1665

gaa tat  gaa aat gtt gcc cga  gaa tgt cgg ctt ggc  agc aag gaa      5049
Glu Tyr  Glu Asn Val Ala Arg  Glu Cys Arg Leu Gly  Ser Lys Glu
    1670                 1675                 1680

ggt cgt  ccc ttc tct ggg gtc  act gct tgc ctg gac  ttc tgt gct      5094
Gly Arg  Pro Phe Ser Gly Val  Thr Ala Cys Leu Asp  Phe Cys Ala
    1685                 1690                 1695

cat ccc  cac agg gac att cac  aac atg aat aat gga  agc act gtg      5139
His Pro  His Arg Asp Ile His  Asn Met Asn Asn Gly  Ser Thr Val
    1700                 1705                 1710

gtt tgt  acc tta act cga gaa  gat aac cgc tct ttg  ggt gtt att      5184
Val Cys  Thr Leu Thr Arg Glu  Asp Asn Arg Ser Leu  Gly Val Ile
    1715                 1720                 1725

cct caa  gat gag cag ctc cat  gtg cta cct ctt tat  aag ctt tca      5229
Pro Gln  Asp Glu Gln Leu His  Val Leu Pro Leu Tyr  Lys Leu Ser
    1730                 1735                 1740

gac aca  gat gag ttt ggc tcc  aag gaa gga atg gaa  gcc aag atc      5274
Asp Thr  Asp Glu Phe Gly Ser  Lys Glu Gly Met Glu  Ala Lys Ile
    1745                 1750                 1755

aaa tct  ggg gcc atc gag gtc  ctg gca ccc cgc cgc  aaa aaa aga      5319
Lys Ser  Gly Ala Ile Glu Val  Leu Ala Pro Arg Arg  Lys Lys Arg
    1760                 1765                 1770

acg tgt  ttc act cag cct gtt  ccc cgt tct gga aag  aag agg gct      5364
Thr Cys  Phe Thr Gln Pro Val  Pro Arg Ser Gly Lys  Lys Arg Ala
    1775                 1780                 1785

gcg atg  atg aca gag gtt ctt  gca cat aag ata agg  gca gtg gaa      5409
Ala Met  Met Thr Glu Val Leu  Ala His Lys Ile Arg  Ala Val Glu
    1790                 1795                 1800

aag aaa  cct att ccc cga atc  aag cgg aag aat aac  tca aca aca      5454
Lys Lys  Pro Ile Pro Arg Ile  Lys Arg Lys Asn Asn  Ser Thr Thr
    1805                 1810                 1815

aca aac  aac agt aag cct tcg  tca ctg cca acc tta  ggg agt aac      5499
Thr Asn  Asn Ser Lys Pro Ser  Ser Leu Pro Thr Leu  Gly Ser Asn
    1820                 1825                 1830

act gag  acc gtg caa cct gaa  gta aaa agt gaa acc  gaa ccc cat      5544
Thr Glu  Thr Val Gln Pro Glu  Val Lys Ser Glu Thr  Glu Pro His
    1835                 1840                 1845

ttt atc  tta aaa agt tca gac  aac act aaa act tat  tcg ctg atg      5589
Phe Ile  Leu Lys Ser Ser Asp  Asn Thr Lys Thr Tyr  Ser Leu Met
    1850                 1855                 1860
```

```
cca tcc  gct cct cac cca gtg  aaa gag gca tct cca  ggc ttc tcc      5634
Pro Ser  Ala Pro His Pro Val  Lys Glu Ala Ser Pro  Gly Phe Ser
    1865                 1870                 1875

tgg tcc  ccg aag act gct tca  gcc aca cca gct cca  ctg aag aat      5679
Trp Ser  Pro Lys Thr Ala Ser  Ala Thr Pro Ala Pro  Leu Lys Asn
    1880                 1885                 1890

gac gca  aca gcc tca tgc ggg  ttt tca gaa aga agc  agc act ccc      5724
Asp Ala  Thr Ala Ser Cys Gly  Phe Ser Glu Arg Ser  Ser Thr Pro
    1895                 1900                 1905

cac tgt  acg atg cct tcg gga  aga ctc agt ggt gcc  aat gca gct      5769
His Cys  Thr Met Pro Ser Gly  Arg Leu Ser Gly Ala  Asn Ala Ala
    1910                 1915                 1920

gct gct  gat ggc cct ggc att  tca cag ctt ggc gaa  gtg gct cct      5814
Ala Ala  Asp Gly Pro Gly Ile  Ser Gln Leu Gly Glu  Val Ala Pro
    1925                 1930                 1935

ctc ccc  acc ctg tct gct cct  gtg atg gag ccc ctc  att aat tct      5859
Leu Pro  Thr Leu Ser Ala Pro  Val Met Glu Pro Leu  Ile Asn Ser
    1940                 1945                 1950

gag cct  tcc act ggt gtg act  gag ccg cta acg cct  cat cag cca      5904
Glu Pro  Ser Thr Gly Val Thr  Glu Pro Leu Thr Pro  His Gln Pro
    1955                 1960                 1965

aac cac  cag ccc tcc ttc ctc  acc tct cct caa gac  ctt gcc tct      5949
Asn His  Gln Pro Ser Phe Leu  Thr Ser Pro Gln Asp  Leu Ala Ser
    1970                 1975                 1980

tct cca  atg gaa gaa gat gag  cag cat tct gaa gca  gat gag cct      5994
Ser Pro  Met Glu Glu Asp Glu  Gln His Ser Glu Ala  Asp Glu Pro
    1985                 1990                 1995

cca tca  gac gaa ccc cta tct  gat gac ccc ctg tca  cct gct gag      6039
Pro Ser  Asp Glu Pro Leu Ser  Asp Asp Pro Leu Ser  Pro Ala Glu
    2000                 2005                 2010

gag aaa  ttg ccc cac att gat  gag tat tgg tca gac  agt gag cac      6084
Glu Lys  Leu Pro His Ile Asp  Glu Tyr Trp Ser Asp  Ser Glu His
    2015                 2020                 2025

atc ttt  ttg gat gca aat att  ggt ggg gtg gcc atc  gca cct gct      6129
Ile Phe  Leu Asp Ala Asn Ile  Gly Gly Val Ala Ile  Ala Pro Ala
    2030                 2035                 2040

cac ggc  tcg gtt ttg att gag  tgt gcc cgg cga gag  ctg cac gct      6174
His Gly  Ser Val Leu Ile Glu  Cys Ala Arg Arg Glu  Leu His Ala
    2045                 2050                 2055

acc act  cct gtt gag cac ccc  aac cgt aat cat cca  acc cgc ctc      6219
Thr Thr  Pro Val Glu His Pro  Asn Arg Asn His Pro  Thr Arg Leu
    2060                 2065                 2070

tcc ctt  gtc ttt tac cag cac  aaa aac cta aat aag  ccc caa cat      6264
Ser Leu  Val Phe Tyr Gln His  Lys Asn Leu Asn Lys  Pro Gln His
    2075                 2080                 2085

ggt ttt  gaa cta aac aag att  aag ttt gag gct aaa  gaa gct aag      6309
Gly Phe  Glu Leu Asn Lys Ile  Lys Phe Glu Ala Lys  Glu Ala Lys
    2090                 2095                 2100

aat aag  aaa atg aag gcc tca  gag caa aaa gac cag  gca gct aat      6354
Asn Lys  Lys Met Lys Ala Ser  Glu Gln Lys Asp Gln  Ala Ala Asn
    2105                 2110                 2115

gaa ggt  cca gaa cag tcc tct  gaa gta aat gaa ttg  aac caa att      6399
Glu Gly  Pro Glu Gln Ser Ser  Glu Val Asn Glu Leu  Asn Gln Ile
    2120                 2125                 2130

cct tct  cat aaa gca tta aca  tta acc cat gac aat  gtt gtc acc      6444
Pro Ser  His Lys Ala Leu Thr  Leu Thr His Asp Asn  Val Val Thr
    2135                 2140                 2145

gtg tcc  cct tat gct ctc aca  cac gtt gcg ggg ccc  tat aac cat      6489
Val Ser  Pro Tyr Ala Leu Thr  His Val Ala Gly Pro  Tyr Asn His
```

```
    2150                2155                2160

tgg gtc  tga                                                     6498
Trp Val
    2165


<210> SEQ ID NO 4
<211> LENGTH: 2165
<212> TYPE: PRT
<213> ORGANISM: Homo sapiens

<400> SEQUENCE: 4

Met Ser Arg Ser Arg His Ala Arg Pro Ser Arg Leu Val Arg Lys Glu
1               5                   10                  15

Asp Val Asn Lys Lys Lys Lys Asn Ser Gln Leu Arg Lys Thr Thr Lys
            20                  25                  30

Gly Ala Asn Lys Asn Val Ala Ser Val Lys Thr Leu Ser Pro Gly Lys
        35                  40                  45

Leu Lys Gln Leu Ile Gln Glu Arg Asp Val Lys Lys Lys Thr Glu Pro
    50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95

Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
        115                 120                 125

Pro Leu Ser Lys Gly Leu Glu Lys Gln His Asp Cys Asp Tyr Lys Ile
    130                 135                 140

Leu Pro Ala Leu Gly Val Lys His Ser Glu Asn Asp Ser Val Pro Met
145                 150                 155                 160

Gln Gly Thr Gln Val Leu Pro Asp Ile Glu Thr Leu Ile Gly Val Gln
                165                 170                 175

Asn Pro Ser Leu Leu Lys Gly Lys Ser Gln Glu Thr Thr Gln Phe Trp
            180                 185                 190

Ser Gln Arg Val Glu Asp Ser Lys Ile Asn Ile Pro Thr His Ser Gly
        195                 200                 205

Pro Ala Ala Glu Ile Leu Pro Gly Pro Leu Glu Gly Thr Arg Cys Gly
    210                 215                 220

Glu Gly Leu Phe Ser Glu Glu Thr Leu Asn Asp Thr Ser Gly Ser Pro
225                 230                 235                 240

Lys Met Phe Ala Gln Asp Thr Val Cys Ala Pro Phe Pro Gln Arg Ala
                245                 250                 255

Thr Pro Lys Val Thr Ser Gln Gly Asn Pro Ser Ile Gln Leu Glu Glu
            260                 265                 270

Leu Gly Ser Arg Val Glu Ser Leu Lys Leu Ser Asp Ser Tyr Leu Asp
        275                 280                 285

Pro Ile Lys Ser Glu His Asp Cys Tyr Pro Thr Ser Ser Leu Asn Lys
    290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
                325                 330                 335

Ala Thr Leu Gly Ala Lys Pro Asp His Gln Glu Ala Phe Glu Ala Thr
            340                 345                 350
```

```
Ala Asn Gln Gln Glu Val Ser Asp Thr Thr Ser Phe Leu Gly Gln Ala
        355                 360                 365

Phe Gly Ala Ile Pro His Gln Trp Glu Leu Pro Gly Ala Asp Pro Val
    370                 375                 380

His Gly Glu Ala Leu Gly Glu Thr Pro Asp Leu Pro Glu Ile Pro Gly
385                 390                 395                 400

Ala Ile Pro Val Gln Gly Glu Val Phe Gly Thr Ile Leu Asp Gln Gln
                405                 410                 415

Glu Thr Leu Gly Met Ser Gly Ser Val Val Pro Asp Leu Pro Val Phe
            420                 425                 430

Leu Pro Val Pro Pro Asn Pro Ile Ala Thr Phe Asn Ala Pro Ser Lys
        435                 440                 445

Trp Pro Glu Pro Gln Ser Thr Val Ser Tyr Gly Leu Ala Val Gln Gly
    450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
                485                 490                 495

Val Glu Asn Glu Lys Gln Val His Ile Ser Phe Leu Pro Ala Asn Thr
            500                 505                 510

Gln Gly Phe Pro Leu Ala Pro Glu Arg Gly Leu Phe His Ala Ser Leu
        515                 520                 525

Gly Ile Ala Gln Leu Ser Gln Ala Gly Pro Ser Lys Ser Asp Arg Gly
    530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                565                 570                 575

Thr Thr Leu Leu Pro Thr Leu Glu Lys Lys Lys Arg Lys Arg Cys Gly
            580                 585                 590

Val Cys Glu Pro Cys Gln Gln Lys Thr Asn Cys Gly Glu Cys Thr Tyr
        595                 600                 605

Cys Lys Asn Arg Lys Asn Ser His Gln Ile Cys Lys Lys Arg Lys Cys
    610                 615                 620

Glu Glu Leu Lys Lys Lys Pro Ser Val Val Val Pro Leu Glu Val Ile
625                 630                 635                 640

Lys Glu Asn Lys Arg Pro Gln Arg Glu Lys Lys Pro Lys Val Leu Lys
                645                 650                 655

Ala Asp Phe Asp Asn Lys Pro Val Asn Gly Pro Lys Ser Glu Ser Met
            660                 665                 670

Asp Tyr Ser Arg Cys Gly His Gly Glu Glu Gln Lys Leu Glu Leu Asn
        675                 680                 685

Pro His Thr Val Glu Asn Val Thr Lys Asn Glu Asp Ser Met Thr Gly
    690                 695                 700

Ile Glu Val Glu Lys Trp Thr Gln Asn Lys Lys Ser Gln Leu Thr Asp
705                 710                 715                 720

His Val Lys Gly Asp Phe Ser Ala Asn Val Pro Glu Ala Glu Lys Ser
                725                 730                 735

Lys Asn Ser Glu Val Asp Lys Lys Arg Thr Lys Ser Pro Lys Leu Phe
            740                 745                 750

Val Gln Thr Val Arg Asn Gly Ile Lys His Val His Cys Leu Pro Ala
        755                 760                 765
```

```
Glu Thr Asn Val Ser Phe Lys Lys Phe Asn Ile Glu Glu Phe Gly Lys
    770                 775                 780

Thr Leu Glu Asn Asn Ser Tyr Lys Phe Leu Lys Asp Thr Ala Asn His
785                 790                 795                 800

Lys Asn Ala Met Ser Ser Val Ala Thr Asp Met Ser Cys Asp His Leu
                805                 810                 815

Lys Gly Arg Ser Asn Val Leu Val Phe Gln Gln Pro Gly Phe Asn Cys
            820                 825                 830

Ser Ser Ile Pro His Ser Ser His Ser Ile Ile Asn His His Ala Ser
        835                 840                 845

Ile His Asn Glu Gly Asp Gln Pro Lys Thr Pro Glu Asn Ile Pro Ser
    850                 855                 860

Lys Glu Pro Lys Asp Gly Ser Pro Val Gln Pro Ser Leu Leu Ser Leu
865                 870                 875                 880

Met Lys Asp Arg Arg Leu Thr Leu Glu Gln Val Val Ala Ile Glu Ala
                885                 890                 895

Leu Thr Gln Leu Ser Glu Ala Pro Ser Glu Asn Ser Ser Pro Ser Lys
            900                 905                 910

Ser Glu Lys Asp Glu Glu Ser Glu Gln Arg Thr Ala Ser Leu Leu Asn
        915                 920                 925

Ser Cys Lys Ala Ile Leu Tyr Thr Val Arg Lys Asp Leu Gln Asp Pro
    930                 935                 940

Asn Leu Gln Gly Glu Pro Pro Lys Leu Asn His Cys Pro Ser Leu Glu
945                 950                 955                 960

Lys Gln Ser Ser Cys Asn Thr Val Val Phe Asn Gly Gln Thr Thr Thr
                965                 970                 975

Leu Ser Asn Ser His Ile Asn Ser Ala Thr Asn Gln Ala Ser Thr Lys
            980                 985                 990

Ser His Glu Tyr Ser Lys Val Thr  Asn Ser Leu Ser Leu  Phe Ile Pro
        995                 1000                1005

Lys Ser  Asn Ser Ser Lys Ile  Asp Thr Asn Lys Ser  Ile Ala Gln
    1010                1015                1020

Gly Ile  Ile Thr Leu Asp Asn  Cys Ser Asn Asp Leu  His Gln Leu
    1025                1030                1035

Pro Pro  Arg Asn Asn Glu Val  Glu Tyr Cys Asn Gln  Leu Leu Asp
    1040                1045                1050

Ser Ser  Lys Lys Leu Asp Ser  Asp Asp Leu Ser Cys  Gln Asp Ala
    1055                1060                1065

Thr His  Thr Gln Ile Glu Glu  Asp Val Ala Thr Gln  Leu Thr Gln
    1070                1075                1080

Leu Ala  Ser Ile Ile Lys Ile  Asn Tyr Ile Lys Pro  Glu Asp Lys
    1085                1090                1095

Lys Val  Glu Ser Thr Pro Thr  Ser Leu Val Thr Cys  Asn Val Gln
    1100                1105                1110

Gln Lys  Tyr Asn Gln Glu Lys  Gly Thr Met Gln Gln  Lys Pro Pro
    1115                1120                1125

Ser Ser  Val His Asn Asn His  Gly Ser Ser Leu Thr  Lys Gln Lys
    1130                1135                1140

Asn Pro  Thr Gln Lys Lys Thr  Lys Ser Thr Pro Ser  Arg Asp Arg
    1145                1150                1155

Arg Lys  Lys Lys Pro Thr Val  Val Ser Tyr Gln Glu  Asn Asp Arg
    1160                1165                1170

Gln Lys  Trp Glu Lys Leu Ser  Tyr Met Tyr Gly Thr  Ile Cys Asp
```

```
    1175                1180                1185

Ile Trp  Ile Ala Ser Lys Phe  Gln Asn Phe Gly Gln  Phe Cys Pro
    1190                1195                1200

His Asp  Phe Pro Thr Val Phe  Gly Lys Ile Ser Ser  Ser Thr Lys
    1205                1210                1215

Ile Trp  Lys Pro Leu Ala Gln  Thr Arg Ser Ile Met  Gln Pro Lys
    1220                1225                1230

Thr Val  Phe Pro Pro Leu Thr  Gln Ile Lys Leu Gln  Arg Tyr Pro
    1235                1240                1245

Glu Ser  Ala Glu Glu Lys Val  Lys Val Glu Pro Leu  Asp Ser Leu
    1250                1255                1260

Ser Leu  Phe His Leu Lys Thr  Glu Ser Asn Gly Lys  Ala Phe Thr
    1265                1270                1275

Asp Lys  Ala Tyr Asn Ser Gln  Val Gln Leu Thr Val  Asn Ala Asn
    1280                1285                1290

Gln Lys  Ala His Pro Leu Thr  Gln Pro Ser Ser Pro  Pro Asn Gln
    1295                1300                1305

Cys Ala  Asn Val Met Ala Gly  Asp Asp Gln Ile Arg  Phe Gln Gln
    1310                1315                1320

Val Val  Lys Glu Gln Leu Met  His Gln Arg Leu Pro  Thr Leu Pro
    1325                1330                1335

Gly Ile  Ser His Glu Thr Pro  Leu Pro Glu Ser Ala  Leu Thr Leu
    1340                1345                1350

Arg Asn  Val Asn Val Val Cys  Ser Gly Gly Ile Thr  Val Val Ser
    1355                1360                1365

Thr Lys  Ser Glu Glu Glu Val  Cys Ser Ser Ser Phe  Gly Thr Ser
    1370                1375                1380

Glu Phe  Ser Thr Val Asp Ser  Ala Gln Lys Asn Phe  Asn Asp Tyr
    1385                1390                1395

Ala Met  Asn Phe Phe Thr Asn  Pro Thr Lys Asn Leu  Val Ser Ile
    1400                1405                1410

Thr Lys  Asp Ser Glu Leu Pro  Thr Cys Ser Cys Leu  Asp Arg Val
    1415                1420                1425

Ile Gln  Lys Asp Lys Gly Pro  Tyr Tyr Thr His Leu  Gly Ala Gly
    1430                1435                1440

Pro Ser  Val Ala Ala Val Arg  Glu Ile Met Glu Asn  Arg Tyr Gly
    1445                1450                1455

Gln Lys  Gly Asn Ala Ile Arg  Ile Glu Ile Val Val  Tyr Thr Gly
    1460                1465                1470

Lys Glu  Gly Lys Ser Ser His  Gly Cys Pro Ile Ala  Lys Trp Val
    1475                1480                1485

Leu Arg  Arg Ser Ser Asp Glu  Glu Lys Val Leu Cys  Leu Val Arg
    1490                1495                1500

Gln Arg  Thr Gly His His Cys  Pro Thr Ala Val Met  Val Val Leu
    1505                1510                1515

Ile Met  Val Trp Asp Gly Ile  Pro Leu Pro Met Ala  Asp Arg Leu
    1520                1525                1530

Tyr Thr  Glu Leu Thr Glu Asn  Leu Lys Ser Tyr Asn  Gly His Pro
    1535                1540                1545

Thr Asp  Arg Arg Cys Thr Leu  Asn Glu Asn Arg Thr  Cys Thr Cys
    1550                1555                1560

Gln Gly  Ile Asp Pro Glu Thr  Cys Gly Ala Ser Phe  Ser Phe Gly
    1565                1570                1575
```

```
Cys Ser  Trp Ser Met Tyr Phe  Asn Gly Cys Lys Phe  Gly Arg Ser
    1580                 1585                 1590

Pro Ser  Pro Arg Arg Phe Arg  Ile Asp Pro Ser Ser  Pro Leu His
    1595                 1600                 1605

Thr Tyr  Tyr Glu Arg Ile Thr  Lys Gly Arg Asn Pro  Glu Arg Arg
    1610                 1615                 1620

Tyr Met  Lys Pro Glu Arg Ile  Ser Pro Gly His Glu  Ala Met Glu
    1625                 1630                 1635

Lys Asn  Leu Glu Asp Asn Leu  Gln Ser Leu Ala Thr  Arg Leu Ala
    1640                 1645                 1650

Pro Ile  Tyr Lys Gln Tyr Ala  Pro Val Ala Tyr Gln  Asn Gln Val
    1655                 1660                 1665

Glu Tyr  Glu Asn Val Ala Arg  Glu Cys Arg Leu Gly  Ser Lys Glu
    1670                 1675                 1680

Gly Arg  Pro Phe Ser Gly Val  Thr Ala Cys Leu Asp  Phe Cys Ala
    1685                 1690                 1695

His Pro  His Arg Asp Ile His  Asn Met Asn Asn Gly  Ser Thr Val
    1700                 1705                 1710

Val Cys  Thr Leu Thr Arg Glu  Asp Asn Arg Ser Leu  Gly Val Ile
    1715                 1720                 1725

Pro Gln  Asp Glu Gln Leu His  Val Leu Pro Leu Tyr  Lys Leu Ser
    1730                 1735                 1740

Asp Thr  Asp Glu Phe Gly Ser  Lys Glu Gly Met Glu  Ala Lys Ile
    1745                 1750                 1755

Lys Ser  Gly Ala Ile Glu Val  Leu Ala Pro Arg Arg  Lys Lys Arg
    1760                 1765                 1770

Thr Cys  Phe Thr Gln Pro Val  Pro Arg Ser Gly Lys  Lys Arg Ala
    1775                 1780                 1785

Ala Met  Met Thr Glu Val Leu  Ala His Lys Ile Arg  Ala Val Glu
    1790                 1795                 1800

Lys Lys  Pro Ile Pro Arg Ile  Lys Arg Lys Asn Asn  Ser Thr Thr
    1805                 1810                 1815

Thr Asn  Asn Ser Lys Pro Ser  Ser Leu Pro Thr Leu  Gly Ser Asn
    1820                 1825                 1830

Thr Glu  Thr Val Gln Pro Glu  Val Lys Ser Glu Thr  Glu Pro His
    1835                 1840                 1845

Phe Ile  Leu Lys Ser Ser Asp  Asn Thr Lys Thr Tyr  Ser Leu Met
    1850                 1855                 1860

Pro Ser  Ala Pro His Pro Val  Lys Glu Ala Ser Pro  Gly Phe Ser
    1865                 1870                 1875

Trp Ser  Pro Lys Thr Ala Ser  Ala Thr Pro Ala Pro  Leu Lys Asn
    1880                 1885                 1890

Asp Ala  Thr Ala Ser Cys Gly  Phe Ser Glu Arg Ser  Ser Thr Pro
    1895                 1900                 1905

His Cys  Thr Met Pro Ser Gly  Arg Leu Ser Gly Ala  Asn Ala Ala
    1910                 1915                 1920

Ala Ala  Asp Gly Pro Gly Ile  Ser Gln Leu Gly Glu  Val Ala Pro
    1925                 1930                 1935

Leu Pro  Thr Leu Ser Ala Pro  Val Met Glu Pro Leu  Ile Asn Ser
    1940                 1945                 1950

Glu Pro  Ser Thr Gly Val Thr  Glu Pro Leu Thr Pro  His Gln Pro
    1955                 1960                 1965
```

```
Asn His  Gln Pro Ser Phe Leu  Thr Ser Pro Gln Asp  Leu Ala Ser
    1970                 1975                 1980

Ser Pro  Met Glu Glu Asp Glu  Gln His Ser Glu Ala  Asp Glu Pro
    1985                 1990                 1995

Pro Ser  Asp Glu Pro Leu Ser  Asp Asp Pro Leu Ser  Pro Ala Glu
    2000                 2005                 2010

Glu Lys  Leu Pro His Ile Asp  Glu Tyr Trp Ser Asp  Ser Glu His
    2015                 2020                 2025

Ile Phe  Leu Asp Ala Asn Ile  Gly Gly Val Ala Ile  Ala Pro Ala
    2030                 2035                 2040

His Gly  Ser Val Leu Ile Glu  Cys Ala Arg Arg Glu  Leu His Ala
    2045                 2050                 2055

Thr Thr  Pro Val Glu His Pro  Asn Arg Asn His Pro  Thr Arg Leu
    2060                 2065                 2070

Ser Leu  Val Phe Tyr Gln His  Lys Asn Leu Asn Lys  Pro Gln His
    2075                 2080                 2085

Gly Phe  Glu Leu Asn Lys Ile  Lys Phe Glu Ala Lys  Glu Ala Lys
    2090                 2095                 2100

Asn Lys  Lys Met Lys Ala Ser  Glu Gln Lys Asp Gln  Ala Ala Asn
    2105                 2110                 2115

Glu Gly  Pro Glu Gln Ser Ser  Glu Val Asn Glu Leu  Asn Gln Ile
    2120                 2125                 2130

Pro Ser  His Lys Ala Leu Thr  Leu Thr His Asp Asn  Val Val Thr
    2135                 2140                 2145

Val Ser  Pro Tyr Ala Leu Thr  His Val Ala Gly Pro  Tyr Asn His
    2150                 2155                 2160

Trp Val
    2165


<210> SEQ ID NO 5
<211> LENGTH: 4005
<212> TYPE: DNA
<213> ORGANISM: Homo sapiens
<220> FEATURE:
<221> NAME/KEY: CDS
<222> LOCATION: (1)..(4005)

<400> SEQUENCE: 5

atg tct cga tcc cgc cat gca agg cct tcc aga tta gtc agg aag gaa       48
Met Ser Arg Ser Arg His Ala Arg Pro Ser Arg Leu Val Arg Lys Glu
1               5                   10                  15

gat gta aac aaa aaa aag aaa aac agc caa cta cga aag aca acc aag       96
Asp Val Asn Lys Lys Lys Lys Asn Ser Gln Leu Arg Lys Thr Thr Lys
            20                  25                  30

gga gcc aac aaa aat gtg gca tca gtc aag act tta agc cct gga aaa      144
Gly Ala Asn Lys Asn Val Ala Ser Val Lys Thr Leu Ser Pro Gly Lys
        35                  40                  45

tta aag caa tta att caa gaa aga gat gtt aag aaa aaa aca gaa cct      192
Leu Lys Gln Leu Ile Gln Glu Arg Asp Val Lys Lys Lys Thr Glu Pro
    50                  55                  60

aaa cca ccc gtg cca gtc aga agc ctt ctg aca aga gct gga gca gca      240
Lys Pro Pro Val Pro Val Arg Ser Leu Leu Thr Arg Ala Gly Ala Ala
65                  70                  75                  80

cgc atg aat ttg gat agg act gag gtt ctt ttt cag aac cca gag tcc      288
Arg Met Asn Leu Asp Arg Thr Glu Val Leu Phe Gln Asn Pro Glu Ser
                85                  90                  95

tta acc tgc aat ggg ttt aca atg gcg cta cga agc acc tct ctt agc      336
Leu Thr Cys Asn Gly Phe Thr Met Ala Leu Arg Ser Thr Ser Leu Ser
```

```
            100                 105                 110

agg cga ctc tcc caa ccc cca ctg gtc gta gcc aaa tcc aaa aag gtt      384
Arg Arg Leu Ser Gln Pro Pro Leu Val Val Ala Lys Ser Lys Lys Val
        115                 120                 125

cca ctt tct aag ggt tta gaa aag caa cat gat tgt gat tat aag ata      432
Pro Leu Ser Lys Gly Leu Glu Lys Gln His Asp Cys Asp Tyr Lys Ile
    130                 135                 140

ctc cct gct ttg gga gta aag cac tca gaa aat gat tcg gtt cca atg      480
Leu Pro Ala Leu Gly Val Lys His Ser Glu Asn Asp Ser Val Pro Met
145                 150                 155                 160

caa ggc acc caa gtc ctt cct gat ata gag act cta att ggt gta caa      528
Gln Gly Thr Gln Val Leu Pro Asp Ile Glu Thr Leu Ile Gly Val Gln
                165                 170                 175

aat ccc tct tta ctt aaa ggt aag agc caa gag aca act cag ttt tgg      576
Asn Pro Ser Leu Leu Lys Gly Lys Ser Gln Glu Thr Thr Gln Phe Trp
            180                 185                 190

tcc caa aga gtt gag gat tcc aag atc aat atc cct acc cac agt ggc      624
Ser Gln Arg Val Glu Asp Ser Lys Ile Asn Ile Pro Thr His Ser Gly
        195                 200                 205

cct gca gct gag atc ctt cct ggg cca ctg gaa ggg aca cgc tgt ggt      672
Pro Ala Ala Glu Ile Leu Pro Gly Pro Leu Glu Gly Thr Arg Cys Gly
    210                 215                 220

gaa gga cta ttc tct gaa gag aca ttg aat gat acc agt ggt tcc cca      720
Glu Gly Leu Phe Ser Glu Glu Thr Leu Asn Asp Thr Ser Gly Ser Pro
225                 230                 235                 240

aaa atg ttt gct cag gac aca gtg tgt gct cct ttt ccc caa aga gca      768
Lys Met Phe Ala Gln Asp Thr Val Cys Ala Pro Phe Pro Gln Arg Ala
                245                 250                 255

acc ccc aaa gtt acc tct caa gga aac ccc agc att cag tta gaa gag      816
Thr Pro Lys Val Thr Ser Gln Gly Asn Pro Ser Ile Gln Leu Glu Glu
            260                 265                 270

ttg ggt tca cga gta gaa tct ctt aag tta tct gat tct tac ctg gat      864
Leu Gly Ser Arg Val Glu Ser Leu Lys Leu Ser Asp Ser Tyr Leu Asp
        275                 280                 285

ccc att aaa agt gaa cat gat tgc tac ccc acc tcc agt ctt aat aag      912
Pro Ile Lys Ser Glu His Asp Cys Tyr Pro Thr Ser Ser Leu Asn Lys
    290                 295                 300

gtt ata cct gac ttg aac ctt aga aac tgc ttg gct ctt ggt ggg tct      960
Val Ile Pro Asp Leu Asn Leu Arg Asn Cys Leu Ala Leu Gly Gly Ser
305                 310                 315                 320

acg tct cct acc tct gta ata aaa ttc ctc ttg gca ggc tca aaa caa     1008
Thr Ser Pro Thr Ser Val Ile Lys Phe Leu Leu Ala Gly Ser Lys Gln
                325                 330                 335

gcg acc ctt ggt gct aaa cca gat cat caa gag gcc ttc gaa gct act     1056
Ala Thr Leu Gly Ala Lys Pro Asp His Gln Glu Ala Phe Glu Ala Thr
            340                 345                 350

gca aat caa cag gaa gtt tct gat acc acc tct ttc cta gga cag gcc     1104
Ala Asn Gln Gln Glu Val Ser Asp Thr Thr Ser Phe Leu Gly Gln Ala
        355                 360                 365

ttt ggt gct atc cca cat caa tgg gaa ctt cct ggt gct gac cca gtt     1152
Phe Gly Ala Ile Pro His Gln Trp Glu Leu Pro Gly Ala Asp Pro Val
    370                 375                 380

cat ggt gag gcc ctg ggt gag acc cca gat cta cca gag att cct ggt     1200
His Gly Glu Ala Leu Gly Glu Thr Pro Asp Leu Pro Glu Ile Pro Gly
385                 390                 395                 400

gct att cca gtc caa gga gag gtc ttt ggt act att tta gac caa caa     1248
Ala Ile Pro Val Gln Gly Glu Val Phe Gly Thr Ile Leu Asp Gln Gln
                405                 410                 415

gaa act ctt ggt atg agt ggg agt gtt gtc cca gac ttg cct gtc ttc     1296
```

```
Glu Thr Leu Gly Met Ser Gly Ser Val Val Pro Asp Leu Pro Val Phe
            420                 425                 430

ctt cct gtt cct cca aat cca att gct acc ttt aat gct cct tcc aaa     1344
Leu Pro Val Pro Pro Asn Pro Ile Ala Thr Phe Asn Ala Pro Ser Lys
        435                 440                 445

tgg cct gag ccc caa agc act gtc tca tat gga ctt gca gtc cag ggt     1392
Trp Pro Glu Pro Gln Ser Thr Val Ser Tyr Gly Leu Ala Val Gln Gly
    450                 455                 460

gct ata cag att ttg cct ttg ggc tca gga cac act cct caa tca tca     1440
Ala Ile Gln Ile Leu Pro Leu Gly Ser Gly His Thr Pro Gln Ser Ser
465                 470                 475                 480

tca aac tca gag aaa aat tca tta cct cca gta atg gct ata agc aat     1488
Ser Asn Ser Glu Lys Asn Ser Leu Pro Pro Val Met Ala Ile Ser Asn
                485                 490                 495

gta gaa aat gag aag cag gtt cat ata agc ttc ctg cca gct aac act     1536
Val Glu Asn Glu Lys Gln Val His Ile Ser Phe Leu Pro Ala Asn Thr
            500                 505                 510

cag ggg ttc cca tta gcc cct gag aga gga ctc ttc cat gct tca ctg     1584
Gln Gly Phe Pro Leu Ala Pro Glu Arg Gly Leu Phe His Ala Ser Leu
        515                 520                 525

ggt ata gcc caa ctc tct cag gct ggt cct agc aaa tca gac aga ggg     1632
Gly Ile Ala Gln Leu Ser Gln Ala Gly Pro Ser Lys Ser Asp Arg Gly
    530                 535                 540

agc tcc cag gtc agt gta acc agc aca gtt cat gtt gtc aac acc aca     1680
Ser Ser Gln Val Ser Val Thr Ser Thr Val His Val Val Asn Thr Thr
545                 550                 555                 560

gtg gtg act atg cca gtg cca atg gtc agt acc tcc tct tct tcc tat     1728
Val Val Thr Met Pro Val Pro Met Val Ser Thr Ser Ser Ser Ser Tyr
                565                 570                 575

acc act ttg cta ccg act ttg gaa aag aag aaa aga aag cga tgt ggg     1776
Thr Thr Leu Leu Pro Thr Leu Glu Lys Lys Lys Arg Lys Arg Cys Gly
            580                 585                 590

gtc tgt gaa ccc tgc cag cag aag acc aac tgt ggt gaa tgc act tac     1824
Val Cys Glu Pro Cys Gln Gln Lys Thr Asn Cys Gly Glu Cys Thr Tyr
        595                 600                 605

tgc aag aac aga aag aac agc cat cag atc tgt aag aaa aga aaa tgt     1872
Cys Lys Asn Arg Lys Asn Ser His Gln Ile Cys Lys Lys Arg Lys Cys
    610                 615                 620

gag gag ctg aaa aag aaa cca tct gtt gtt gtg cct ctg gag gtt ata     1920
Glu Glu Leu Lys Lys Lys Pro Ser Val Val Val Pro Leu Glu Val Ile
625                 630                 635                 640

aag gaa aac aag agg ccc cag agg gaa aag aag ccc aaa gtt tta aag     1968
Lys Glu Asn Lys Arg Pro Gln Arg Glu Lys Lys Pro Lys Val Leu Lys
                645                 650                 655

gtt tta aga aga agc agt gat gaa gaa aaa gtt ctt tgt ttg gtc cgg     2016
Val Leu Arg Arg Ser Ser Asp Glu Glu Lys Val Leu Cys Leu Val Arg
            660                 665                 670

cag cgt aca ggc cac cac tgt cca act gct gtg atg gtg gtg ctc atc     2064
Gln Arg Thr Gly His His Cys Pro Thr Ala Val Met Val Val Leu Ile
        675                 680                 685

atg gtg tgg gat ggc atc cct ctt cca atg gcc gac cgg cta tac aca     2112
Met Val Trp Asp Gly Ile Pro Leu Pro Met Ala Asp Arg Leu Tyr Thr
    690                 695                 700

gag ctc aca gag aat cta aag tca tac aat ggg cac cct acc gac aga     2160
Glu Leu Thr Glu Asn Leu Lys Ser Tyr Asn Gly His Pro Thr Asp Arg
705                 710                 715                 720

aga tgc acc ctc aat gaa aat cgt acc tgt aca tgt caa gga att gat     2208
Arg Cys Thr Leu Asn Glu Asn Arg Thr Cys Thr Cys Gln Gly Ile Asp
                725                 730                 735
```

```
cca gag act tgt gga gct tca ttc tct ttt ggc tgt tca tgg agt atg     2256
Pro Glu Thr Cys Gly Ala Ser Phe Ser Phe Gly Cys Ser Trp Ser Met
            740                 745                 750

tac ttt aat ggc tgt aag ttt ggt aga agc cca agc ccc aga aga ttt     2304
Tyr Phe Asn Gly Cys Lys Phe Gly Arg Ser Pro Ser Pro Arg Arg Phe
        755                 760                 765

aga att gat cca agc tct ccc tta cat acc tac tat gaa aga att act     2352
Arg Ile Asp Pro Ser Ser Pro Leu His Thr Tyr Tyr Glu Arg Ile Thr
    770                 775                 780

aaa gga cgt aat cca gaa aga aga tat atg aaa ccg gaa cga atc agt     2400
Lys Gly Arg Asn Pro Glu Arg Arg Tyr Met Lys Pro Glu Arg Ile Ser
785                 790                 795                 800

ccg gga cac gag gcc atg gaa aaa aac ctt gaa gat aac tta cag agt     2448
Pro Gly His Glu Ala Met Glu Lys Asn Leu Glu Asp Asn Leu Gln Ser
                805                 810                 815

ttg gct aca cga tta gct cca att tat aag cag tat gct cca gta gct     2496
Leu Ala Thr Arg Leu Ala Pro Ile Tyr Lys Gln Tyr Ala Pro Val Ala
            820                 825                 830

tac caa aat cag gtg gaa tat gaa aat gtt gcc cga gaa tgt cgg ctt     2544
Tyr Gln Asn Gln Val Glu Tyr Glu Asn Val Ala Arg Glu Cys Arg Leu
        835                 840                 845

ggc agc aag gaa ggt cgt ccc ttc tct ggg gtc act gct tgc ctg gac     2592
Gly Ser Lys Glu Gly Arg Pro Phe Ser Gly Val Thr Ala Cys Leu Asp
    850                 855                 860

ttc tgt gct cat ccc cac agg gac att cac aac atg aat aat gga agc     2640
Phe Cys Ala His Pro His Arg Asp Ile His Asn Met Asn Asn Gly Ser
865                 870                 875                 880

act gtg gtt tgt acc tta act cga gaa gat aac cgc tct ttg ggt gtt     2688
Thr Val Val Cys Thr Leu Thr Arg Glu Asp Asn Arg Ser Leu Gly Val
                885                 890                 895

att cct caa gat gag cag ctc cat gtg cta cct ctt tat aag ctt tca     2736
Ile Pro Gln Asp Glu Gln Leu His Val Leu Pro Leu Tyr Lys Leu Ser
            900                 905                 910

gac aca gat gag ttt ggc tcc aag gaa gga atg gaa gcc aag atc aaa     2784
Asp Thr Asp Glu Phe Gly Ser Lys Glu Gly Met Glu Ala Lys Ile Lys
        915                 920                 925

tct ggg gcc atc gag gtc ctg gca ccc cgc cgc aaa aaa aga acg tgt     2832
Ser Gly Ala Ile Glu Val Leu Ala Pro Arg Arg Lys Lys Arg Thr Cys
    930                 935                 940

ttc act cag cct gtt ccc cgt tct gga aag aag agg gct gcg atg atg     2880
Phe Thr Gln Pro Val Pro Arg Ser Gly Lys Lys Arg Ala Ala Met Met
945                 950                 955                 960

aca gag gtt ctt gca cat aag ata agg gca gtg gaa aag aaa cct att     2928
Thr Glu Val Leu Ala His Lys Ile Arg Ala Val Glu Lys Lys Pro Ile
                965                 970                 975

ccc cga atc aag cgg aag aat aac tca aca aca aca aac aac agt aag     2976
Pro Arg Ile Lys Arg Lys Asn Asn Ser Thr Thr Thr Asn Asn Ser Lys
            980                 985                 990

cct tcg tca ctg cca acc tta ggg  agt aac act gag acc  gtg caa cct   3024
Pro Ser Ser Leu Pro Thr Leu Gly  Ser Asn Thr Glu Thr  Val Gln Pro
        995                 1000                1005

gaa gta  aaa agt gaa acc gaa  ccc cat ttt atc tta  aaa agt tca      3069
Glu Val  Lys Ser Glu Thr Glu  Pro His Phe Ile Leu  Lys Ser Ser
    1010                 1015                 1020

gac aac  act aaa act tat tcg  ctg atg cca tcc gct  cct cac cca      3114
Asp Asn  Thr Lys Thr Tyr Ser  Leu Met Pro Ser Ala  Pro His Pro
    1025                 1030                 1035

gtg aaa  gag gca tct cca ggc  ttc tcc tgg tcc ccg  aag act gct      3159
Val Lys  Glu Ala Ser Pro Gly  Phe Ser Trp Ser Pro  Lys Thr Ala
    1040                 1045                 1050
```

```
tca gcc  aca cca gct cca ctg  aag aat gac gca aca  gcc tca tgc      3204
Ser Ala  Thr Pro Ala Pro Leu  Lys Asn Asp Ala Thr  Ala Ser Cys
    1055                 1060                 1065

ggg ttt  tca gaa aga agc agc  act ccc cac tgt acg  atg cct tcg      3249
Gly Phe  Ser Glu Arg Ser Ser  Thr Pro His Cys Thr  Met Pro Ser
    1070                 1075                 1080

gga aga  ctc agt ggt gcc aat  gca gct gct gct gat  ggc cct ggc      3294
Gly Arg  Leu Ser Gly Ala Asn  Ala Ala Ala Ala Asp  Gly Pro Gly
    1085                 1090                 1095

att tca  cag ctt ggc gaa gtg  gct cct ctc ccc acc  ctg tct gct      3339
Ile Ser  Gln Leu Gly Glu Val  Ala Pro Leu Pro Thr  Leu Ser Ala
    1100                 1105                 1110

cct gtg  atg gag ccc ctc att  aat tct gag cct tcc  act ggt gtg      3384
Pro Val  Met Glu Pro Leu Ile  Asn Ser Glu Pro Ser  Thr Gly Val
    1115                 1120                 1125

act gag  ccg cta acg cct cat  cag cca aac cac cag  ccc tcc ttc      3429
Thr Glu  Pro Leu Thr Pro His  Gln Pro Asn His Gln  Pro Ser Phe
    1130                 1135                 1140

ctc acc  tct cct caa gac ctt  gcc tct tct cca atg  gaa gaa gat      3474
Leu Thr  Ser Pro Gln Asp Leu  Ala Ser Ser Pro Met  Glu Glu Asp
    1145                 1150                 1155

gag cag  cat tct gaa gca gat  gag cct cca tca gac  gaa ccc cta      3519
Glu Gln  His Ser Glu Ala Asp  Glu Pro Pro Ser Asp  Glu Pro Leu
    1160                 1165                 1170

tct gat  gac ccc ctg tca cct  gct gag gag aaa ttg  ccc cac att      3564
Ser Asp  Asp Pro Leu Ser Pro  Ala Glu Glu Lys Leu  Pro His Ile
    1175                 1180                 1185

gat gag  tat tgg tca gac agt  gag cac atc ttt ttg  gat gca aat      3609
Asp Glu  Tyr Trp Ser Asp Ser  Glu His Ile Phe Leu  Asp Ala Asn
    1190                 1195                 1200

att ggt  ggg gtg gcc atc gca  cct gct cac ggc tcg  gtt ttg att      3654
Ile Gly  Gly Val Ala Ile Ala  Pro Ala His Gly Ser  Val Leu Ile
    1205                 1210                 1215

gag tgt  gcc cgg cga gag ctg  cac gct acc act cct  gtt gag cac      3699
Glu Cys  Ala Arg Arg Glu Leu  His Ala Thr Thr Pro  Val Glu His
    1220                 1225                 1230

ccc aac  cgt aat cat cca acc  cgc ctc tcc ctt gtc  ttt tac cag      3744
Pro Asn  Arg Asn His Pro Thr  Arg Leu Ser Leu Val  Phe Tyr Gln
    1235                 1240                 1245

cac aaa  aac cta aat aag ccc  caa cat ggt ttt gaa  cta aac aag      3789
His Lys  Asn Leu Asn Lys Pro  Gln His Gly Phe Glu  Leu Asn Lys
    1250                 1255                 1260

att aag  ttt gag gct aaa gaa  gct aag aat aag aaa  atg aag gcc      3834
Ile Lys  Phe Glu Ala Lys Glu  Ala Lys Asn Lys Lys  Met Lys Ala
    1265                 1270                 1275

tca gag  caa aaa gac cag gca  gct aat gaa ggt cca  gaa cag tcc      3879
Ser Glu  Gln Lys Asp Gln Ala  Ala Asn Glu Gly Pro  Glu Gln Ser
    1280                 1285                 1290

tct gaa  gta aat gaa ttg aac  caa att cct tct cat  aaa gca tta      3924
Ser Glu  Val Asn Glu Leu Asn  Gln Ile Pro Ser His  Lys Ala Leu
    1295                 1300                 1305

aca tta  acc cat gac aat gtt  gtc acc gtg tcc cct  tat gct ctc      3969
Thr Leu  Thr His Asp Asn Val  Val Thr Val Ser Pro  Tyr Ala Leu
    1310                 1315                 1320

aca cac  gtt gcg ggg ccc tat  aac cat tgg gtc tga                   4005
Thr His  Val Ala Gly Pro Tyr  Asn His Trp Val
    1325                 1330
```

<210> SEQ ID NO 6

<211> LENGTH: 1334
<212> TYPE: PRT
<213> ORGANISM: Homo sapiens

<400> SEQUENCE: 6

```
Met Ser Arg Ser Arg His Ala Arg Pro Ser Arg Leu Val Arg Lys Glu
1               5                   10                  15

Asp Val Asn Lys Lys Lys Lys Asn Ser Gln Leu Arg Lys Thr Thr Lys
            20                  25                  30

Gly Ala Asn Lys Asn Val Ala Ser Val Lys Thr Leu Ser Pro Gly Lys
        35                  40                  45

Leu Lys Gln Leu Ile Gln Glu Arg Asp Val Lys Lys Lys Thr Glu Pro
    50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95

Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
        115                 120                 125

Pro Leu Ser Lys Gly Leu Glu Lys Gln His Asp Cys Asp Tyr Lys Ile
    130                 135                 140

Leu Pro Ala Leu Gly Val Lys His Ser Glu Asn Asp Ser Val Pro Met
145                 150                 155                 160

Gln Gly Thr Gln Val Leu Pro Asp Ile Glu Thr Leu Ile Gly Val Gln
                165                 170                 175

Asn Pro Ser Leu Leu Lys Gly Lys Ser Gln Glu Thr Thr Gln Phe Trp
            180                 185                 190

Ser Gln Arg Val Glu Asp Ser Lys Ile Asn Ile Pro Thr His Ser Gly
        195                 200                 205

Pro Ala Ala Glu Ile Leu Pro Gly Pro Leu Glu Gly Thr Arg Cys Gly
    210                 215                 220

Glu Gly Leu Phe Ser Glu Glu Thr Leu Asn Asp Thr Ser Gly Ser Pro
225                 230                 235                 240

Lys Met Phe Ala Gln Asp Thr Val Cys Ala Pro Phe Pro Gln Arg Ala
                245                 250                 255

Thr Pro Lys Val Thr Ser Gln Gly Asn Pro Ser Ile Gln Leu Glu Glu
            260                 265                 270

Leu Gly Ser Arg Val Glu Ser Leu Lys Leu Ser Asp Ser Tyr Leu Asp
        275                 280                 285

Pro Ile Lys Ser Glu His Asp Cys Tyr Pro Thr Ser Ser Leu Asn Lys
    290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
                325                 330                 335

Ala Thr Leu Gly Ala Lys Pro Asp His Gln Glu Ala Phe Glu Ala Thr
            340                 345                 350

Ala Asn Gln Gln Glu Val Ser Asp Thr Thr Ser Phe Leu Gly Gln Ala
        355                 360                 365

Phe Gly Ala Ile Pro His Gln Trp Glu Leu Pro Gly Ala Asp Pro Val
    370                 375                 380

His Gly Glu Ala Leu Gly Glu Thr Pro Asp Leu Pro Glu Ile Pro Gly
```

```
385                 390                 395                 400

Ala Ile Pro Val Gln Gly Glu Val Phe Gly Thr Ile Leu Asp Gln Gln
                405                 410                 415

Glu Thr Leu Gly Met Ser Gly Ser Val Val Pro Asp Leu Pro Val Phe
            420                 425                 430

Leu Pro Val Pro Pro Asn Pro Ile Ala Thr Phe Asn Ala Pro Ser Lys
        435                 440                 445

Trp Pro Glu Pro Gln Ser Thr Val Ser Tyr Gly Leu Ala Val Gln Gly
    450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
                485                 490                 495

Val Glu Asn Glu Lys Gln Val His Ile Ser Phe Leu Pro Ala Asn Thr
            500                 505                 510

Gln Gly Phe Pro Leu Ala Pro Glu Arg Gly Leu Phe His Ala Ser Leu
        515                 520                 525

Gly Ile Ala Gln Leu Ser Gln Ala Gly Pro Ser Lys Ser Asp Arg Gly
    530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                565                 570                 575

Thr Thr Leu Leu Pro Thr Leu Glu Lys Lys Lys Arg Lys Arg Cys Gly
            580                 585                 590

Val Cys Glu Pro Cys Gln Gln Lys Thr Asn Cys Gly Glu Cys Thr Tyr
        595                 600                 605

Cys Lys Asn Arg Lys Asn Ser His Gln Ile Cys Lys Lys Arg Lys Cys
    610                 615                 620

Glu Glu Leu Lys Lys Lys Pro Ser Val Val Val Pro Leu Glu Val Ile
625                 630                 635                 640

Lys Glu Asn Lys Arg Pro Gln Arg Glu Lys Lys Pro Lys Val Leu Lys
                645                 650                 655

Val Leu Arg Arg Ser Ser Asp Glu Glu Lys Val Leu Cys Leu Val Arg
            660                 665                 670

Gln Arg Thr Gly His His Cys Pro Thr Ala Val Met Val Val Leu Ile
        675                 680                 685

Met Val Trp Asp Gly Ile Pro Leu Pro Met Ala Asp Arg Leu Tyr Thr
    690                 695                 700

Glu Leu Thr Glu Asn Leu Lys Ser Tyr Asn Gly His Pro Thr Asp Arg
705                 710                 715                 720

Arg Cys Thr Leu Asn Glu Asn Arg Thr Cys Thr Cys Gln Gly Ile Asp
                725                 730                 735

Pro Glu Thr Cys Gly Ala Ser Phe Ser Phe Gly Cys Ser Trp Ser Met
            740                 745                 750

Tyr Phe Asn Gly Cys Lys Phe Gly Arg Ser Pro Ser Pro Arg Arg Phe
        755                 760                 765

Arg Ile Asp Pro Ser Ser Pro Leu His Thr Tyr Tyr Glu Arg Ile Thr
    770                 775                 780

Lys Gly Arg Asn Pro Glu Arg Arg Tyr Met Lys Pro Glu Arg Ile Ser
785                 790                 795                 800

Pro Gly His Glu Ala Met Glu Lys Asn Leu Glu Asp Asn Leu Gln Ser
                805                 810                 815
```

```
Leu Ala Thr Arg Leu Ala Pro Ile Tyr Lys Gln Tyr Ala Pro Val Ala
            820                 825                 830

Tyr Gln Asn Gln Val Glu Tyr Glu Asn Val Ala Arg Glu Cys Arg Leu
        835                 840                 845

Gly Ser Lys Glu Gly Arg Pro Phe Ser Gly Val Thr Ala Cys Leu Asp
    850                 855                 860

Phe Cys Ala His Pro His Arg Asp Ile His Asn Met Asn Asn Gly Ser
865                 870                 875                 880

Thr Val Val Cys Thr Leu Thr Arg Glu Asp Asn Arg Ser Leu Gly Val
                885                 890                 895

Ile Pro Gln Asp Glu Gln Leu His Val Leu Pro Leu Tyr Lys Leu Ser
            900                 905                 910

Asp Thr Asp Glu Phe Gly Ser Lys Glu Gly Met Glu Ala Lys Ile Lys
        915                 920                 925

Ser Gly Ala Ile Glu Val Leu Ala Pro Arg Arg Lys Lys Arg Thr Cys
    930                 935                 940

Phe Thr Gln Pro Val Pro Arg Ser Gly Lys Lys Arg Ala Ala Met Met
945                 950                 955                 960

Thr Glu Val Leu Ala His Lys Ile Arg Ala Val Glu Lys Lys Pro Ile
                965                 970                 975

Pro Arg Ile Lys Arg Lys Asn Asn Ser Thr Thr Thr Asn Asn Ser Lys
            980                 985                 990

Pro Ser Ser Leu Pro Thr Leu Gly  Ser Asn Thr Glu Thr  Val Gln Pro
        995                 1000                1005

Glu Val  Lys Ser Glu Thr Glu  Pro His Phe Ile Leu  Lys Ser Ser
    1010                1015                1020

Asp Asn  Thr Lys Thr Tyr Ser  Leu Met Pro Ser Ala  Pro His Pro
    1025                1030                1035

Val Lys  Glu Ala Ser Pro Gly  Phe Ser Trp Ser Pro  Lys Thr Ala
    1040                1045                1050

Ser Ala  Thr Pro Ala Pro Leu  Lys Asn Asp Ala Thr  Ala Ser Cys
    1055                1060                1065

Gly Phe  Ser Glu Arg Ser Ser  Thr Pro His Cys Thr  Met Pro Ser
    1070                1075                1080

Gly Arg  Leu Ser Gly Ala Asn  Ala Ala Ala Ala Asp  Gly Pro Gly
    1085                1090                1095

Ile Ser  Gln Leu Gly Glu Val  Ala Pro Leu Pro Thr  Leu Ser Ala
    1100                1105                1110

Pro Val  Met Glu Pro Leu Ile  Asn Ser Glu Pro Ser  Thr Gly Val
    1115                1120                1125

Thr Glu  Pro Leu Thr Pro His  Gln Pro Asn His Gln  Pro Ser Phe
    1130                1135                1140

Leu Thr  Ser Pro Gln Asp Leu  Ala Ser Ser Pro Met  Glu Glu Asp
    1145                1150                1155

Glu Gln  His Ser Glu Ala Asp  Glu Pro Pro Ser Asp  Glu Pro Leu
    1160                1165                1170

Ser Asp  Asp Pro Leu Ser Pro  Ala Glu Glu Lys Leu  Pro His Ile
    1175                1180                1185

Asp Glu  Tyr Trp Ser Asp Ser  Glu His Ile Phe Leu  Asp Ala Asn
    1190                1195                1200

Ile Gly  Gly Val Ala Ile Ala  Pro Ala His Gly Ser  Val Leu Ile
    1205                1210                1215
```

```
Glu Cys  Ala Arg Arg Glu Leu  His Ala Thr Thr Pro  Val Glu His
    1220                1225                1230

Pro Asn  Arg Asn His Pro Thr  Arg Leu Ser Leu Val  Phe Tyr Gln
    1235                1240                1245

His Lys  Asn Leu Asn Lys Pro  Gln His Gly Phe Glu  Leu Asn Lys
    1250                1255                1260

Ile Lys  Phe Glu Ala Lys Glu  Ala Lys Asn Lys Lys  Met Lys Ala
    1265                1270                1275

Ser Glu  Gln Lys Asp Gln Ala  Ala Asn Glu Gly Pro  Glu Gln Ser
    1280                1285                1290

Ser Glu  Val Asn Glu Leu Asn  Gln Ile Pro Ser His  Lys Ala Leu
    1295                1300                1305

Thr Leu  Thr His Asp Asn Val  Val Thr Val Ser Pro  Tyr Ala Leu
    1310                1315                1320

Thr His  Val Ala Gly Pro Tyr  Asn His Trp Val
    1325                1330


<210> SEQ ID NO 7
<211> LENGTH: 68
<212> TYPE: DNA
<213> ORGANISM: Artificial sequence
<220> FEATURE:
<223> OTHER INFORMATION: Artificially synthesized primer sequence

<400> SEQUENCE: 7

gcaagaattc ctcgagccac catggactac aaagacgatg acgacaagtc tcgatcccgc     60

catgcaag                                                              68


<210> SEQ ID NO 8
<211> LENGTH: 38
<212> TYPE: DNA
<213> ORGANISM: Artificial sequence
<220> FEATURE:
<223> OTHER INFORMATION: Artificially synthesized primer sequence

<400> SEQUENCE: 8

gagtgaattc ctcgatcaga cccaatggtt atagggcc                             38


<210> SEQ ID NO 9
<211> LENGTH: 41
<212> TYPE: DNA
<213> ORGANISM: Artificial sequence
<220> FEATURE:
<223> OTHER INFORMATION: Artificially synthesized primer sequence

<400> SEQUENCE: 9

gcaagaattc ctcgagccac catgtctcga tcccgccatg c                         41


<210> SEQ ID NO 10
<211> LENGTH: 52
<212> TYPE: DNA
<213> ORGANISM: Artificial sequence
<220> FEATURE:
<223> OTHER INFORMATION: Artificially synthesized primer sequence

<400> SEQUENCE: 10

gagtgaattc ctcgattact tgtcgtcatc gtctttgtag tcgacccaat gg             52


<210> SEQ ID NO 11
<211> LENGTH: 19
<212> TYPE: DNA
<213> ORGANISM: Artificial sequence
```

<220> FEATURE:
<223> OTHER INFORMATION: Artificially synthesized primer sequence

<400> SEQUENCE: 11
agccacatcg ctcagacac 19

<210> SEQ ID NO 12
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 12
gcccaatacg accaaatcc 19

<210> SEQ ID NO 13
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 13
ctttgaggct ctgcagctta g 21

<210> SEQ ID NO 14
<211> LENGTH: 22
<212> TYPE: DNA
<213> ORGANISM: Artificial sequence
<220> FEATURE:
<223> OTHER INFORMATION: Artificially synthesized primer sequence

<400> SEQUENCE: 14
tctgctttgc atatctcctg aa 22

<210> SEQ ID NO 15
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 15
gggggaatgg accttgtata g 21

<210> SEQ ID NO 16
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 16
gcaaagctcc taccgtacca 20

<210> SEQ ID NO 17
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 17
tctccaacat cctgaacctc a 21

<210> SEQ ID NO 18
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 18
ttgctattct tcggccagtt 20

<210> SEQ ID NO 19
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 19
gctgtgacag gtacccaacc 20

<210> SEQ ID NO 20
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 20
catgcaggtg agttgtcaga a 21

<210> SEQ ID NO 21
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 21
ggctgagcac cactacgact 20

<210> SEQ ID NO 22
<211> LENGTH: 25
<212> TYPE: DNA
<213> ORGANISM: Artificial sequence
<220> FEATURE:
<223> OTHER INFORMATION: Artificially synthesized primer sequence

<400> SEQUENCE: 22
gcattataaa atttcccaaa tcatc 25

<210> SEQ ID NO 23
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 23
atttcccgct ctggttcag 19

<210> SEQ ID NO 24
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 24
gttttctcca cggatgttgc 20

<210> SEQ ID NO 25
<211> LENGTH: 18
<212> TYPE: DNA
<213> ORGANISM: Artificial sequence
<220> FEATURE:
<223> OTHER INFORMATION: Artificially synthesized primer sequence

<400> SEQUENCE: 25
acgccgagtt gagcaaga 18

<210> SEQ ID NO 26
<211> LENGTH: 18
<212> TYPE: DNA
<213> ORGANISM: Artificial sequence
<220> FEATURE:
<223> OTHER INFORMATION: Artificially synthesized primer sequence

<400> SEQUENCE: 26
tctgcctcct ccacgaag 18

<210> SEQ ID NO 27
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 27
ggtaccccga catccactt 19

<210> SEQ ID NO 28
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 28
gcctgttctg gaaccatacc t 21

<210> SEQ ID NO 29
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 29
ccgcttgtta ggtcgccgca 20

<210> SEQ ID NO 30
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 30
tgggctgagg gccggagaaa 20

<210> SEQ ID NO 31

<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 31
acacgcacca ccaccacaac a 21

<210> SEQ ID NO 32
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 32
ccggcgagtt tgccaagagc 20

<210> SEQ ID NO 33
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 33
cgacttcacc aactggttct g 21

<210> SEQ ID NO 34
<211> LENGTH: 18
<212> TYPE: DNA
<213> ORGANISM: Artificial sequence
<220> FEATURE:
<223> OTHER INFORMATION: Artificially synthesized primer sequence

<400> SEQUENCE: 34
atgcaggttg tgcgatca 18

<210> SEQ ID NO 35
<211> LENGTH: 22
<212> TYPE: DNA
<213> ORGANISM: Artificial sequence
<220> FEATURE:
<223> OTHER INFORMATION: Artificially synthesized primer sequence

<400> SEQUENCE: 35
tgggatattc aggttcatgt tg 22

<210> SEQ ID NO 36
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 36
actggagttt ggcaggagag 20

<210> SEQ ID NO 37
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 37
gcggccacga cacgaggaat 20

<210> SEQ ID NO 38
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 38
cgcccatcag cccactctcg 20

<210> SEQ ID NO 39
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 39
ccaagcccca gaagattag 19

<210> SEQ ID NO 40
<211> LENGTH: 17
<212> TYPE: DNA
<213> ORGANISM: Artificial sequence
<220> FEATURE:
<223> OTHER INFORMATION: Artificially synthesized primer sequence

<400> SEQUENCE: 40
tggagctaat cgtgtag 17

<210> SEQ ID NO 41
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 41
ggtgcactga aatggaaagg 20

<210> SEQ ID NO 42
<211> LENGTH: 18
<212> TYPE: DNA
<213> ORGANISM: Artificial sequence
<220> FEATURE:
<223> OTHER INFORMATION: Artificially synthesized primer sequence

<400> SEQUENCE: 42
actggcacgc tccatgac 18

<210> SEQ ID NO 43
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 43
ggtgcactga gctcgaaag 19

<210> SEQ ID NO 44
<211> LENGTH: 20
<212> TYPE: DNA

```
<213> ORGANISM: Artificial sequence
<220> FEATURE:
<223> OTHER INFORMATION: Artificially synthesized primer sequence

<400> SEQUENCE: 44

aagaggtgtc ggatgacagg                                              20


<210> SEQ ID NO 45
<211> LENGTH: 27
<212> TYPE: DNA
<213> ORGANISM: Artificial sequence
<220> FEATURE:
<221> NAME/KEY: CDS
<222> LOCATION: (1)..(27)
<223> OTHER INFORMATION: Sequence of FLAG tag

<400> SEQUENCE: 45

atg gac tac aaa gac gat gac gac aag                                27
Met Asp Tyr Lys Asp Asp Asp Asp Lys
1               5


<210> SEQ ID NO 46
<211> LENGTH: 9
<212> TYPE: PRT
<213> ORGANISM: Artificial sequence
<220> FEATURE:
<223> OTHER INFORMATION: Sequence of FLAG tag

<400> SEQUENCE: 46

Met Asp Tyr Lys Asp Asp Asp Asp Lys
1               5
```

METHOD FOR PRODUCING PLURIPOTENT STEM CELLS

TECHNICAL FIELD

The present invention relates to a method of producing pluripotent stem cells (PSCs), more specifically to a method of producing pluripotent stem cells with enhanced differentiation efficacies. Also included in this invention are the proteins used to realize this process.

BACKGROUND ART

PSCs are defined as cell entities which have both the capacity to differentiate toward multiple cell lineages non-identical to themselves (pluripotency) and a capability of producing a cell having an identical capacity to the originated cell as a daughter cell when they divide (self-renewal), which is considered to include embryonic stem (ES) cell and induced pluripotent stem (iPS) cell. And because of these characteristics, ES cell and iPS cell are strongly anticipated to play important roles in regenerative medicine and/or drug screening.

However, it has been recently reported that mouse PSCs and human PSCs do not share some of their fundamental properties and moreover, human PSCs are generally considered to have lower differentiation capabilities when compared to mouse PSCs.

Mouse PSCs can be challenged experimentally for their pluripotency with some accuracy. For example, mouse ES cells can be injected into a cavity of blastocyst where the injected cells intermingle with the host inner cell mass (ICM), followed by a normal development of ES cell-derived cells in an embryo, which is called as chimera formation. The fact that mouse ES cells can synchronize their development with a timing-matched ICM is a good verdict for pluripotency. In this case, as development further proceeds, it is known that part of the injected ES cells might also contribute to the germline. This germline transmission means that these cells can contribute to the next generation and further corroborates the compatibility as normal cells in a more generic term.

There also exists an "ultimate" way to show pluripotency. When we inhibit the first cell cleavage of a mouse fertilized egg transiently and culture it in a culture dish, we can obtain a tetraploid blastocyst. The tetraploid blastocyst looks almost normal but will not continue development into embryo further. Therefore, just by putting tetraploid embryos back to a uterus of pseudo-pregnant female mouse would not produce a live pup. But if we inject stem cells with differentiation capabilities into these tetraploid blastocysts and let them contribute to the chimera formation as mentioned above, the PSCs now would be fully responsible to contribute to development as they are the sole cells with normal karyotype. In this way, we can obtain a completely PSC-derived body in a single generation. This methodology is called the tetraploid-complementation assay and the obtained pups are called as all-iPS mice, according to the PSCs injected. This multiple tests enable strict assessment of pluripotencies in mouse and mouse iPS cells have been shown to exhibit strict pluripotencies using the battery of such multiple tests.

In sharp contrast, human pluripotencies cannot be scrutinized in these fashions because of ethical issues. An alternative way to show pluripotency in human contexts is teratoma formation. When stem cells are transplanted into nude mice subcutaneously, these cells when supported by the host blood supply, do differentiate at random to form an organ. The formed stem cell-derived tumor mass will be pathologically examined to find ectoderm, mesoderm and endoderm, and thereby, the originated stem cells are qualified as pluripotent. However, this methodology whereby we assess pluripotency by teratoma formation is inherently problematic. That is, even if the original stem cells have insufficient efficacy of differentiation, any differentiation efficacy above zero could be judged as "pluripotency" if three germ layers are observed. Teratoma assay would judge the pluripotency without considering the existence of residual undifferentiated cells within the teratoma. With the current paradigm of teratoma assay, the mere presence of a limited number of bona fide pluripotent cells within the cell population would be sufficient and the current teratoma assay has no implication about the quantitative trait of pluripotency. For example, mouse iPS cells derived using c-Myc, albeit showing three-germ-layer differentiation in teratoma assays, were prone to give iPS cell-derived tumors upon chimera formation. An alternative to teratoma assay would be to independently direct cell differentiation toward the three germ layers. However, there is no "golden standard" in any cell differentiation protocol making this strategy inapplicable for quantitative analysis.

There is also a more profound and fundamental problem with human PSCs. This is about the possible absence of an ideal PSC for human which bears the capacity to be amenable to equally robust differentiation toward all the cell lineages. Osafune et al. have reported that no two human ES cell lines showed quasi-identical gene expression profile, and thus each ES cell line has own propensity to differentiate into a specific germ layer, and further, suggested that human ES cells do not have sufficient pluripotency in terms of quantitative evaluation (non-patent literature 1).

It took 17 years after the discovery of mouse ES cell to establish human ES cell. In retrospect, the major reason for this delay was that human ES cell could not be established in the same way as in the mouse ES cell. Although mouse ES cells are dependent to leukemia inhibitory factor (LIF) for their self renewal, human ES cell cannot show self renewal ability in a medium added with LIF. Thomson et al. found that human ES cell requires fibroblast growth factor (FGF) and Activin/Nodal for its maintenance (non-patent literature 2). These differential requirements for mouse and human ES cell self renewal diversify into different intracellular signaling pathways: JAK/STAT signaling and SMAD2/3 signaling for mouse and human ES cell, respectively. The currently major view is that SMAD2/3 signaling in human PSCs activates the expression of NANOG. In parallel, SMAD2/3 signaling is a critical factor for the mesendoderm development in mammals and therefore a high concentration of Activin is required for proper mesendoderm differentiation of PSCs. It is therefore interesting to note that the current human PSC self renewal signaling crossovers with the signal which would induce its mesendodermal differentiation.

Mouse and human ES cells both originate from blastocysts. However, most probably owing to their difference in the culture conditions, their characteristics significantly differ. A major contrast is albeit mouse ES cells retain characteristics of their originated blastocyst inner cells, human ES cells are more akin to the primitive ectoderm of the epiblast, which appears after some development of the blastocyst. Then, the epiblast stem cell (EpiSC) was established directly from mouse epiblasts using culture condition equivalent to human ES cells (non-patent literature 3 and 4). This had led the stem cell biologists to discriminate two stages of pluripotency. One is the blastocyst-type pluripotency, represented by mouse ES as well as iPS cells and the other is the epiblast-type pluripotency, which includes human ES, human iPS cells and mouse EpiSCs. The former pluripotency is now called "naive" and the latter "primed", originally coined by Smith et al. (non-patent literature 5).

Naive and primed pluripotencies share the three germ layer differentiation capabilities and teratoma assay-compatibilities upon transplantation into nude mouse. However, naive PSCs are more similar to the earlier stage (blastocyst) of development closer to fertilized ovum, are easier to be established in culture and possess fuller pluripotency in that an individual body completely derived from these cells can be generated. In contrast, primed PSCs are more akin to the epiblast, an embryonic stage following the blastocyst, and are empirically tougher to establish. Additionally, as described above, primed PSCs have clear differentiation propensities (non-patent literature 1). Finally, it has been recognized that primed PSCs poorly synchronize their development with early embryo and therefore do not produce chimera, and thus it is known that primed human PSCs are inferior to mouse naive PSCs in differentiation efficacy including pluripotency.

In practicing regenerative medicine and drug development, human PSCs are being anticipated to exert their high differentiation capabilities in order to supply various cell types, tissues and organogenesis. In this line, it seems desirable to enhance differentiation efficacy of primed human PSCs. However, this kind of innovation remains to be developed.

PRIOR ART DOCUMENTS

Non-Patent Literature

[Non-patent literature 1] Osafune, K. et al., *Nat Biotechnol.* 2008, 26, 313-315.

[Non-patent literature 2] Thomson, J. A. et al., *Science* 1998, 282, 1145-7.

[Non-patent literature 3] Brons, I. et al., *Nature* 2007, 448, 191-5.

[Non-patent literature 4] Tesar, P. J. et al., *Nature* 2007, 448, 196-9.

[Non-patent literature 5] Nichols, J., *Cell Stem Cell* 2009, 4, 487-92.

DISCLOSURE OF THE INVENTION

Problems to be Solved by the Invention

The present invention has been made to address the other problems referred to in the cited art above, and objects of the invention are to provide a method for producing PSCs with improved differentiation capabilities and also substances which enable such production.

Measures to Solve the Referred Problems

In order to achieve the purposes, the present inventors have comparatively studied the differences in the characteristics of mouse PSCs and human PSCs.

Mouse PSCs bear characteristics close to inner clump of cells of the pre-implantation blastocyst. In contrast, human PSCs are most akin to the primitive ectodermal cells of the post-implantation epiblast. We can assume by this difference between mouse and human pluripotencies that human PSCs is inherently inferior to mouse PSCs for its differentiation capabilities.

There is two distinct phases of reprogramming during development. One occurs during the transition from a fertilized egg to a pre-implantation embryo (which we shall refer to as "reprogramming during early development") and another happens post-implantation during the establishment of the germ cell lineage ("germline reprogramming"). From this viewpoint, the present inventors examined factors expressed in the "germline reprogramming" to reset cell memories acquired from the blastocyst to the epiblast stage, and thereby the present inventors have come up with TET1.

It has been shown that TET1 protein is an enzyme involved in hydroxylation of methyl group of 5-methylcytosine (5mC) to convert 5mC to 5-hydroxymethylcytosine (5hmC). It has been recently shown that TET1 is involved in demethylation of 5mC to cytosine. It is also supposed that TET1 protein can competitively inhibit the binding of the DNA methyltransferases such as DNMT1, DNMT3a and DNMT3b to their target DNA methylation sites leading to a hypomethylated genome. Therefore, TET1 protein function is strongly suggested in the process of DNA demethylation and/or the maintenance of a hypomethylated state. Moreover in mice, TET1 protein expression can be observed in the development of early embryo from the fertilized egg to the blastocyst onward, in the primordial germ cells and in ES cells established from blastocysts. Coupled with its function in DNA demethylation, TET1 protein is strongly suggested to be involved in reprogramming processes. However, the role of TET1 protein in the human is totally unexplored.

Given the situation, the present inventors investigated the expression of TET1 at the transcriptional as well as translational levels. As a result, the present inventors found that human iPS cells, just like mouse ES cells, abundantly express TET1 mRNA. The present inventors have also identified two novel TET1 mRNA (cDNA) sequences which differed from the known sequences in terms of the presence or absence of a part of exons and therefore the present inventors succeeded in finding novel splice variants for TET1.

However, to their surprises, the present inventors were unable to detect TET1 at the protein level in human iPS cells, unlike in mouse ES cells. The inventors have deduced that this differential expressivity of TET1 protein between mouse PSCs and human PSCs might be causal for the observed difference in the differentiation capacities of these two cell entities and have therefore investigated a way to overexpress TET1 protein in human PSCs. In this line of investigations, the inventors have found that placing a peptide-tag at the wild-type TET1 protein's N-terminus allowed them to stably express TET1 protein in human PSCs. The inventors have further demonstrated that simply replacing its second amino acid to another one renders the protein more stable.

The inventors succeeded in forcing TET1 expression in hiPSCs by exploiting the mutant TET1 protein (modified TET1 protein) which can be stably expressed in hiPSCs, which led them to notice that expression of T and SOX17, mesendodermal markers usually expressed in conventional hiPSCs, was missing. This showed that the mutant TET1 protein can cancel some of the differentiation biases (propensities), an inherent nature of the current human iPSCs.

When mutant TET1-introduced hiPSCs were induced toward neuroectoderm (ectoderm), the expression of OCT3/4 and NANOG which operate in resisting cell differentiation were rapidly diminished. Especially, NANOG operates by counteracting differentiation signals to most kinds of cells and therefore, the swift down-regulation of this factor upon mutant-TET1 introduction could be a reason for the observed decrease in the differentiation resistance by this factor and the enhanced pluripotency. Moreover, the inventors demonstrated that mutant-TET1 introduction renders hiPSCs more amenable to neural differentiation judged by the enhanced up-regulation of the neural markers SOX2 and SOX1. Especially, SOX1 up-regulation was mostly sensitive to the mutant TET1-introduction as shown by the 60-fold upregulation of SOX1 when compared to their parental control cells produced without TET1 introduction, which suggests that differentiation capacity to neurons of PSCs increased about 60-fold by introduction of this protein.

In corroboration with these transcription factors' regulations, conditions which would poorly produce neurons from conventional TET1-non-expressing hiPSC were able to induce neurons at 100% efficiency for mutant TET1-expressing iPSCs. In addition to this ectodermal differentiation, the inventors showed that the mutant-TET1 introduction allowed them to increase the efficacy of definitive endoderm differentiation.

Even more surprisingly, the effect on differentiation efficacy of TET1 was also exerted when the second amino acid was simply replaced with another amino acid and furthermore, even when the dioxygenase catalytic domain was omitted. This indicates the observed effect of TET1 introduction does not rely on the DNA demethylating activity that the dioxygenase domain is responsible for but rather on the DNA-binding properties of TET1.

The present inventors further demonstrate that the mutant-TET1, when introduced together with the so-called reprogramming factors (Oct3/4, Sox2, Klf4 and c-Myc) into somatic cells not only enhance the differentiation efficacy of the obtained iPSCs but also the yield (production efficacy) of such iPSC clones.

The inventors also found that the TET1-introduced iPSCs have significantly reduced levels of various cancer-related markers (such as GPC4, GAGE2B and GAGE7) when compared to the parental cell line which indicates that, in addition to improving the differentiation potentials (and/or the production efficiency of such cells), TET1-introduced iPSCs bear enhanced safety.

This invention was completed according to the mentioned experimental results obtained by the inventors and provides a method which allows the production of PSCs with enhanced efficacies for cell differentiation. Furthermore, this invention also provides materials to practice the production of PSCs such as mutant TET1 proteins, novel TET1 protein isoforms which can be used as raw material for these mutant TET1 proteins as well as nucleic acids which code for such proteins. More in details, the present invention provides the following aspects.

<1> A method for producing pluripotent stem cells, comprising:

introducing at least one molecule selected from the group consisting of (a) to (c) into pluripotent stem cells (PSCs) or somatic cells which are to be induced toward PSCs;

(a) TET1 protein,
(b) a nucleic acid that encodes TET1 protein, and
(c) a vector into which a nucleic acid that encodes TET1 protein has been inserted.

<2> The method of <1>, wherein said TET1 protein is a mutant TET1 protein which has enhanced stability as compared to a wild type TET1 protein.

<3> The method of <2>, wherein said mutant TET1 protein is a mutant TET1 protein in which the second amino acid from their N-terminus differs from the wild-type TET1's second amino acid from their N-terminus.

<4> The method of <2> or <3>, wherein said mutant TET1 protein lacks its dioxygenase domain.

<5> The method of <1>, wherein said TET1 protein is a protein consisting of the amino acid sequence of SEQ ID NO: 2, 4 or 6.

<6> A mutant TET1 protein which has enhanced stability as compared to a wild type TET1 protein.

<7> The protein of <6>, wherein the second amino acid from their N-terminus differs from the wild-type TET1's second amino acid from their N-terminus.

<8> The protein of <7>, which lacks its dioxygenase domain.

<9> A protein consisting of the amino acid sequence of SEQ ID NO: 4 or 6.

<10> A nucleic acid encoding the protein as described in any one of <6> to <9>.

<11> A vector into which the nucleic acid of <10> has been inserted.

<12> A pluripotent stem cell (PSC) or somatic cell which is to be induced toward PSC into which at least one molecule selected from the group consisting of (a) to (c) has been introduced;

(a) TET1 protein,
(b) a nucleic acid that encodes TET1 protein, and
(c) a vector into which a nucleic acid that encodes TET1 protein has been inserted.

The Effects of the Invention

The invention accordingly provides a way to enhance the differentiation efficacy of PSCs. Furthermore, the invention can also allow increasing the production efficacy of iPS cell reprogramming. Moreover, it is also possible to produce highly safe PSCs with suppressed tumorigenicity.

EMBODIMENTS FOR CARRYING OUT THE INVENTION

Figure 1:
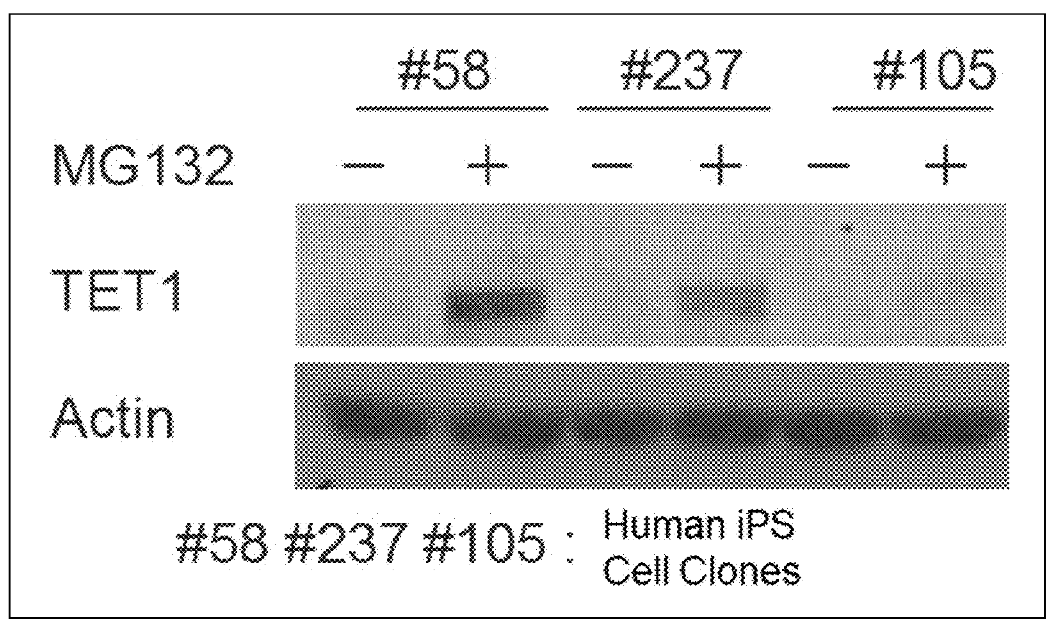
FIG. 1 The picture shows the result of the western blotting for analyzing the expression amount of TET1 protein in individual human iPS cells (#58, #237 and #105) with or without proteasome inhibitor (MG132).

<The Method for Producing PSCs of this Invention>

This invention provides the methods for producing PSCs which comprises introducing at least one molecule selected from the group consisting of (a) to (c) into pluripotent stem cells (PSCs) or somatic cells which are to be induced toward PSCs;

(a) TET1 protein, (b) a nucleic acid that encodes TET1 protein, and (c) a vector into which a nucleic acid that encodes TET1 protein has been inserted.

Furthermore, according to the production method, PSCs with enhanced differentiation capacity can be produced. Furthermore, according to the production method, by introducing the TET1 protein etc. into the somatic cells, it becomes possible to produce iPS cells with higher efficacy. Moreover, it is also possible to produce highly safe PSCs with suppressed tumorigenicity.

In this invention, "pluripotent stem cell (PSC)" denotes for a cell with a dual capacity of being able to differentiate into multiple cell lineages different from itself (pluripotency) and at the same time being able to divide into daughter cells which bear the same capacity with itself (self renewal).

In this invention, "differentiation capacity" denotes for a cell capacity to change into a different kind of cell. And an "enhancement of differentiation efficacy" in this invention specifically denotes not only an increase of cell differentiation probability as monitored by increased differentiation marker expression (in case of neural induction the markers could be SOX2, SOX1, NEUROGENIN1, NEUROGENIN2, NEUROD1, ASCL1, PAX6, ZNF521 or OTX2) but also a significant repression of other cell lineage choice (in case where ectoderm specification is required such other lineage markers could be T and SOX17) as well as significant repression of factors which act to resist differentiation signals such as NANOG. As shown in the following examples, the differentiation capacities of a PSC are in a repressed state which can be expressed as differentiation resistance and also proper differentiation can be blocked by an inherent differentiation propensity toward an undesired cell fate. To this line, the present invention provides a way to cancel these robust differentiation resistance or propensity enabling a PSC to faithfully execute its pluripotency. In this way, when mentioning about the enhancement of differentiation capacity, this will automatically include an improvement in the pluripotency.

Candidate pluripotent stem cell lines where the invention could be applied to enhance the differentiation capacities includes embryonic stem cell (ES cell), epiblast stem cell (EpiSC), embryonal carcinoma cell (EC cell), embryonic germ cell (EG cell), multipotent germ stem cell (mGS cell) and MUSE cell (refer to Kuroda Y. et al., Proc. Natl. Acad. Sci. U.S.A., 2010. 107, 8639-43), cells which can be obtained from various sources of the organism. Moreover, the list includes cells such as iPS cells which have been induced to obtain pluripotency artificially from somatic cells obtained from the organism.

There is no specific restriction for the source organism of these cells and examples thereof include human as well as non-human (mouse, rat, cattle, horse, porcine, goat, monkey, dog, cat, bird, etc.) animals.

PSCs can be staged either in an earlier developmental stage (blastocyst) where the corresponding PSCs are called naive PSCs or also in a developmental stage which appears after the blastocyst and called the epiblast in which case the PSCs are called primed PSCs. It is generally believed that the latter PSCs have lower differentiation capacities compared to the former PSCs. Therefore, it is conceivable that the production method presented in the invention will impact more the primed PSCs. Examples of primed PSCs in this context include ES cells and iPS cells from human, monkey, porcine, ovine, dog and cow and also include EpiSC obtained from human as well as non-human sources.

In the production method described in this invention, the preferred "TET1 protein" used to be introduced in pluripotent stem cells or a somatic cell to be induced to pluripotent stem cells is a "mutant TET1 protein".

In this present invention, the "mutant TET1 protein" may be a protein obtained by artificially introducing a mutation into the wild type TET1 protein as described below or a protein whereby a mutation naturally (non-artificially) occurred in the wild type TET1 protein as long as it has a function of enhancing differentiation efficacy of PSCs when it is introduced into the PSCs. In order to assess such enhancement of a PSC differentiation efficacy, one can for example introduce the TET1 protein into PSCs and evaluate the expression of factors which induce differentiation into different cell lineage, differentiation markers, factors which represent the differentiation propensity or factors which exhibit differentiation resistance, during various differentiation paradigms.

As for the mutant TET1 protein, it is preferred that the TET1 protein has an increased stability when expressed in a primed pluripotent stem cell. One can assess if the protein is more stable or not by known protein detection method such as Western blotting as shown in Examples shown below.

Preferred examples of "a mutant protein having enhanced stability as compared to the wild type TET1 protein" include a protein in which the second amino acid from the N-terminus is different from that of the wild type TET1 protein.

The TET1 protein which differs from the wild type TET1 in its second N-terminus amino acid can be obtained, as shown below, by artificially introducing a mutation to the wild type TET1 protein. Such a mutant TET1 protein may be a mutant protein having the mutation that occurred naturally.

An example of the TET1 mutant having amino acid substitution includes a TET1 protein in which the second amino acid from the N-terminus (which is a serine in the case of human TET1 protein) has been replaced with a different amino acid (for an example glycine). Although there is no particular restriction about the method to change the second amino acid from the N-terminus of TET1 protein, we can for example use site-directed mutagenesis (Kramer W. & Fritz H J., Methods Enzymol., 1987. 154, 350).

An example of the TET1 mutant having amino acid insertion or addition includes a TET1 protein in which one or plural amino acids have been inserted between the first and the second amino acid of the N-terminus of the wild type TET1 protein or a TET1 protein in which one or plural amino acids have been added to the N-terminus of the wild type TET1 protein. In these cases, plural amino acids could be any plural number for example two to 100 amino acids (preferably 2 to 50 or even more preferably 2 to 10 amino acids). There is no restriction for the method used to insert or add amino acids in the way and so, polymerase chain reaction (PCR) can be performed by using a primer containing an oligonucleotide encoding an amino acid or a peptide to be inserted or added.

An example of the TET1 mutant having amino acid deletion includes a TET1 protein in which one or plural amino acids have been deleted from the N-terminal portion of the wild type TET1 protein. In this case, from the perspective of retaining the functions of the TET1 protein without impairing the DNA binding region, it is preferable that one or plural amino acids have been deleted in the region from amino acid number 1 to 584 counted from the N-terminus of the wild type TET1 protein. In this case too, there is no restriction of the number of "plural" amino acids to be deleted, but the number is for example 2 to 100 (preferably 2 to 50 and more preferably 2 to 10). There is no restriction for the method used to delete amino acids in the way and so, a DNA encoding a TET1 protein having a deletion can be obtained by PCR.

Also as will be shown in the working example 9, it is possible to obtain an enhancement of the differentiation efficacy of the PSCs if the DNA binding motif of TET1 is preserved and therefore the de-methylating activity is redundant. Therefore the mutant TET1 protein may be a mutant having a deletion of a region locating C-terminus side from the DNA binding region (CXXC domain), and more specifically may be a mutant TET1 protein which lacks its dioxygenase domain or may be a mutant TET1 protein which lacks both the cysteine-rich and the dioxygenase domains.

In this invention, the DNA-binding domain of TET1 protein refers to the amino acid stretch encompassing the lysine 585 to lysine 613 of the human TET1 protein (SEQ ID NO: 2, 4 or 6). The dioxygenase domain refers to the amino acid stretch encompassing amino acids 1611 to 2074 in SEQ ID NO: 2, amino acids 1640 to 2103 in SEQ ID NO: 4 or amino acids 809 to 1272 in SEQ ID NO: 6. Also the cysteine-rich domain refers to the amino acid stretch encompassing amino acids 1418 to 1610 in SEQ ID NO: 2, amino acids 1418 to 1608 and 1638 to 1639 in SEQ ID NO: 4 or amino acids 657 to 777 and 807 to 808 in SEQ ID NO: 6.

So far mentioned are examples of the preferred examples for the mutant proteins used in this invention, however, as far as that by introducing it into a pluripotent stem cell, the cell exhibit enhanced differentiation capability, one can also use TET1 proteins which bear other mutation. For example, considering that TET1, TET2 and TET3 proteins all share quasi-equivalent catalytic (dioxygenase) domains, one can swap the TET1-dioxygenase domain with that of TET2 or TET3 protein, or can directly or indirectly combine the TET1-DNA-binding domain and the dioxygenase domain of TET2 or TET3 protein for such purpose.

For the production method of this invention, it is also conceivable to introduce the wild-type TET1 protein into a pluripotent stem cell. The "wild-type TET1 protein" in this invention typically refers to proteins of SEQ ID NO: 2, 4 or 6 or their naturally occurring homologues which are supposedly degraded in primed pluripotent stem cells. When using such wild-type TET1 protein, it is preferable to use an excess amount of the protein in such a way it exceeds the capacity of a given pluripotent stem cell to degrade it. Or from the point of view of inhibiting such degradation in a pluripotent stem cell, one may additionally use a decoy of TET1 protein. For such a decoy, one may use a polypeptide derived from the N-terminus of the wild-type TET1 protein.

As shown in the examples described later, in order to enhance the differentiation potential of pluripotent stem cells, it is necessary that the function of the DNA-binding domain of the protein having the amino acid sequence of SEQ ID NO: 2, 4 or 6 is maintained. Therefore, such homolog of the protein having the amino acid sequence of SEQ ID NO: 2, 4 or 6 is preferably a natural protein with sequence homology of over 70% (for example, 75%, 80% 85%, 90%, 95%, 97%, over 99%) to the DNA-binding domain (CXXC domain) of the protein. Such natural proteins can be listed as identified by accession number XP_003359270, XP_004777901, XP_005602635, XP_002805756, XP 003928828, XP 002735044, XP 005168673, of CG43444, and the like.

In this invention, a "homology in amino acid sequence" denotes a perfect match and the proportion (in %) of the matched amino acids (similar amino acids) regarding their physical-chemical properties including basicity and acidity and can be determined by using BLASTP program (Altschul et al. J. Mol. Biol., 215: 403-410, 1990), and the like. The program is based on the BLAST algorithm originally proposed by Karlin and Altschul (Proc. Natl. Acad. Sci. USA, 87:2264-2268, 1990, Proc. Natl. Acad. Sci. USA, 90:5873-5877, 1993). More specifically, BLAST homology search of the NCBI page (http://blast.ncbi.nlm.nih.gov/Blast.cgi), the default parameters, the program including "protein blast" and "blastx" can be used to determine homology. These methods for analyses are well known to those in the art.

Also, in case that the mutant TET1 protein described in this invention may be degraded in primed pluripotent stem cells, one may use excess amount overexpression or decoy strategy described above for wild-type TET1 protein.

For the preparation of mutant TET1 proteins in this invention, we previously mentioned methods where one can modify nucleic acids which code for wild-type TET1 protein. Those in the art may for example be able to produce such mutant TET1 proteins by introducing the nucleic acids encoding the mutant TET1 proteins by baculovirus-infection of Sf9 insect cells. Moreover, besides such genetically mutant preparations, one may directly synthesize mutant TET1 proteins used in this invention by a commercially available poly-peptide synthesizer in a chemical fashion.

To prepare such wild-type TET1 protein, those skilled in the art can obtain nucleic acid coding for said protein by using know method such as hybridization technologies onto cDNA library or genomic DNA library obtained from human or non-human tissues which express TET1 protein and then, use the preparation method mentioned for the preparation of the mutant TET1 protein such as introducing the nucleic acid obtained as above into an insect cell. Alternatively, one can also synthesize such wild-type TET1 protein using a commercially available polypeptide synthesizer according the amino acid sequence shown in SEQ ID NO: 2.

For the methods to introduce the nucleic acids encoding the mutant TET1 proteins into PSCs or the after-mentioned somatic cells which will be utilized to induce PSCs, we do not have any particular restrictions and therefore are able to use methods such as viral infection, lipofection, liposome introduction, electroporation, Ca phosphate, DEAE dextran or microinjection of the expression vectors which bear the nucleic acids encoding the TET1 proteins (for example its cDNA) within appropriate expression vectors which are known to function in the desired cell types.

Such expression vectors include, for examples, viral expression systems such as lentivirus, retrovirus, adenovirus, adeno-associated virus, herpes virus, Sendai virus as well as mammalian expression plasmid vectors such as episomal vectors, PiggyBac transposon vectors. Among these, from the standpoint that the nucleic acids encoding the TET1 proteins are not integrated into the cell's genome, it is preferable to use episomal vectors or Sendai virus. Moreover, from the standpoint that the nucleic acids are temporarily introduced in the genome but will be able to be removed away by transposase, it is preferable to use PiggyBac transposon vector.

For such expression vectors, we can exploit promoters such as CAG, SRα, SV40, LTR, CMV, RSV or HSV-TK promoters. Such promoter selection can include promoters where the expression of the genes introduced beneath can be controlled by the presence or absence of the added agents (for example tetracycline). The expression vectors can also bear, in addition to the promoter, enhancer, poly A addition signal, selection markers (for examples, puromycin-resistance or neomycin-resistance genes) or SV40 replication origin.

The modes of expression of the aforementioned TET1 protein-encoding nucleic acids introduced into PSCs can either be transient, inducible or constitutive. However, regarding its function in extinguishing the expression of NANOG, an inhibitory factor for differentiation induction, and also that differentiation may be hindered if the so-called reprogramming signal by TET1 persists during differentiation process from PSCs produced by the method of this invention to other cell lineage, the preferred expression modes should be transient or inducible. Such controlled expression period is preferably between one day before the commencement of the differentiation of PSCs produced by the method of this invention and 4 days after it.

Methods wherein we can introduce the TET1 protein into each cells include the use of protein cell transfection agents, introducing a protein transduction domain (PTD) fused to the mutant protein, electroporation or direct microinjection.

For the culture conditions used on or after introduction of the mutant TET1 proteins or the nucleic acid encoding it or a vector inserted with the nucleic acid, there is no specific restriction but could be specified by conditions used by those in the art such as culture media constituents, culture temperature, culture humidity, carbon dioxide and/or oxygen tension. Regarding the hydroxylation reaction that the TET1 may provide, it is preferable that Fe, α-ketoglutarate or ascorbic acid (vitamin C) are included in the culture media.

The types of somatic cells to be reprogrammed to PSCs by introduction of the TET1 protein can be anything, and examples thereof include fibroblasts, epithelial cells, blood cells, arbitrary cells derived from an animal. Reprogramming of such cells toward PSCs (especially toward iPS cells) can be achieved by introducing such "reprogramming factors" into somatic cells to erase the cellular memory of each somatic cell.

Such "reprogramming factors" denote any factors with the capacity of harnessing pluripotency to the somatic cells when introduced singly or in concert with other factors such as OCT3/4, c-MYC, L-MYC, N-MYC, SOX2, KLF4, KLF5, KLF2, LIN28, NANOG, ECAT1, ESG1, FBX15, ERAS, ECAT7, ECAT8, GDF3, SOX15, ECAT15-1, ECAT15-2, Fth117, SALL1, SALL4, REX1, UTF1, TCL1, STELLA, β-catenin, ESRRB, PRDM14, TBX3, STAT3, GATA3 and GRB2 proteins as well as miR-199a-3p, miR-291-3p, miR-294, miR-295 (miR-290 cluster) as well as miR-302 cluster microRNA. Among all these factors, from the viewpoint that the reprogramming occurs with relatively small number of factors, it is preferred to introduce OCT3/4, c-MYC, SOX2 and KLF4 (the so-called Yamanaka factors) into somatic cells. To reduce the tumorigenicity of the obtained PSCs, it is also preferable to replace c-MYC with L-MYC from the four factors or to introduce OCT3/4, SOX2 and KLF4 (3 factors). Moreover, from the standpoint of the induction efficacy of the PSCs, it is preferable to introduce OCT3/4, L-MYC, SOX2, KLF4 and LIN28 and also, chemical compounds or nucleic acids which can inhibit the function of p53 or p21 into the somatic cells. Meanwhile, the "reprogramming factor" does not necessarily have to be the above-described proteins and the like, and may be a low-molecular-weight compound having an alternative function to these or capable of inducing these expressions. Examples of such a low-molecular-weight compound include histone deacetylase (HDAC) inhibitors such as valproic acid (VPA), GSK-3β inhibitors such as CHIR99021, TGF-β1 type receptor inhibitors such as 616452, histone demethylase inhibitors such as tranylcypromine, cAMP production promoters such as forskolin, histone methyltransferase inhibitors such as 3-deazaneplanocin (DZNep), and combinations thereof.

In this present invention, the methods to introduce reprogramming factors into somatic cells can be anything as being discussed about the methods for introducing the TET1 proteins; by selecting the relevant publicly known method, if a protein is to be introduced, the embodiment could be the protein itself or the nucleic acids encoding such protein and if a microRNA is desired, we can introduce it as nucleic acid molecules. But if such reprogramming factors persist within the obtained PSCs, the cells may acquire some resistance against cell differentiation to other cell lineage and makes it difficult to stably harnessing new cell memories. From this point, it is preferable to introduce nucleic acids encoding the reprogramming factors through the use of episomal vectors, Sendai virus or PiggyBac transposon vector.

The timing of such introduction of reprogramming factors can be before, simultaneous or after the introduction of the TET1 proteins or the nucleic acids coding the proteins.

The culture conditions after the introductions of reprogramming factors into somatic cells can be suitably selected by those in the art among the publicly known cell culture methods. An example of such cell culture methods is to culture the cells onto feeder cells in a culture medium suited for somatic cells and then to gradually switch to media suitable for PSCs.

"Feeder cells" can be any cell lines which support the growth and the maintenance of PSCs such as mouse embryonic fibroblasts (MEFs), OP-9 cells, PA6 cells, NIH3T3 cells, M15 cells, 10T/2 cells, STO cells or SNL cells. It is also preferable that the growth of such cells are reduced by antibiotic treatment (like Mitomycin C treatment) or by irradiation.

"A culture medium suited for somatic cells" can be anything publicly known to those in the art and be further selected according the kind of somatic cells used. For examples as basic culture media, we can list Roswell Park Memorial Institute (RPMI) 1640 medium, Minimally Essential Medium (α-MEM), Dulbecco's modified Eagle Medium (DMEM) and F12 medium and to these basic media we can add supplements such as human sera, cytokines, amino acids needed to cell culture (for example L-glutamine) and antibiotics (such as streptomycin, penicillin, puromycin) to prepare "a culture medium suited for somatic cells".

"Media suitable for PSCs" can be selected according to the originated animal from a battery of publicly known media. To give an example of such media for human PSCs, DMEM/F12 supplemented with Knockout Serum Replacement (KSR; Life Technologies), L-glutamine, non-essential amino acids, 2-mercaptoethanol and FGF2 can be one option.

The aforementioned co-culture method with feeder cells is a preferred method for inducing and maintaining PSCs as it provides an easy way to maintain the undifferentiated state of the cells. However, from the standpoint of enhancing the differentiation efficacies to ectoderm lineage such as nerve cells and enabling tight control over the cell densities of the PSCs, non-feeder culture and passaging by trituration is the preferred method for the PSCs in this invention. For such non-feeder trituration passaging culture, we can use methods discussed below.

Once the reprogramming factors are introduced to somatic cells, these cells are cultured in E8 medium developed by Thomson's group (Chen G et al., Nat Methods, 2011, vol. 8, 424-429). Once iPS cell colonies become discernible, the obtained PSCs are dispersed into culture media containing KSR, FGF2, Activin A, ROCK inhibitor and fibronectin and then seeded onto collagen type I-coated culture dishes which will produce such non-feeder trituration passaging.

For such trituration passaging, the basic culture media to which KSR, FGF2 and Activin A and so on are to be supplemented can be, for example, DMEM/F12 medium or CDM medium. For the concentrations of KSR, FGF2 and Activin A added to these basic media can be within the ranges of 15-25%, 4 to 100 ng/ml and 0.01 to 20 ng/ml, respectively. In a more preferred embodiment, the concentrations are 20%, 15 ng/ml and 10 ng/ml, respectively. In addition to these supplements, other constituents such as L-glutamine, non-essential amino acids or antibiotics (such as streptomycin, penicillin or puromycin) can be added.

In addition, to enhance the efficacy of inducing PSCs, regardless the presence or absence of feeder cells, chemicals which inhibit the function of HDAC (small molecule inhibitors such as valproic acid (VPA), trichostatin A, sodium butyrate, MC1293 or M344), chemicals which inhibit the function of G9a histone methyltransferase (small molecule inhibitors such as BIX-01294), chemicals which inhibit the function of p53 (small molecule inhibitors such as Pifithrin-α(PFT-α)), chemicals which inhibit the function of p21, compounds which inhibit the function of micro RNAs including, let-7 cluster, miR-17-92, miR-21, miR-29a, miR-106a-363 or miR-106b-25, are preferably to be added when or after the reprogramming factors are introduced into somatic cells. From a similar perspective in which we anticipate that the induction efficacy of PSCs may increase upon inhibition of such factors, we can also introduce to the somatic cells nucleic acids with inhibitory effects toward HDAC, G9a, p53, p21 or micro RNAs such as let-7 cluster (siRNA, shRNA, antisense, aptamers and so on) using publicly know methods for nucleic acid delivery.

Moreover, although the aforementioned culture methods including culture conditions (such as culture temperature, oxygen and carbon dioxide concentrations) can suitably be set by those in the art, from the standpoint that it may enhance the induction efficacy of PSCs, it is preferred to culture in hypoxic condition (oxygen concentration: 5%).

Thus far, we have explained the production methods of PSCs in this present invention. For comparatively evaluating the differentiation efficacies between the PSCs induced by such methods and PSCs in which the mutant TET1 are not introduced, as will be explained in the working example 7 later, one can judge the differentiation efficacy by indexing the efficacy of cell differentiation toward the desired cell lineage (for example by dividing the cell number of the desired cell type after differentiation by the total number of PSCs before such differentiation). Moreover, as will be described in the working examples 5 and 6 later, we can measure the expression levels of differentiation markers (such as SOX1, NEUROGENIN1, NEUROGENIN2, NEUROD1, ASCL1, PAX6, ZNF521 or OTX2 for nerve cells), factors which induce differentiation to other cell lineage (for example, SOX2 when nerve differentiation is desired), factors which mark the differentiation propensities (for example, when ectoderm differentiation is desired, markers such as T and SOX17) or factors which resist proper differentiation (for examples, NANOG and OCT3/4) during the cell differentiation process and deduce and judge from these expression data whether the differentiation efficacy has been improved or not. Moreover, as will be shown in Example 11, the current human iPSCs without TET1-introduction tend to express higher levels of the differentiation markers such as FOXA2, LHX1, LIM2, SOX17, EOMES or T, in addition to undifferentiation markers such as GPC4, GAGE2B and GAGE7. Therefore, those markers can be utilized to assess the enhancement of differentiation capacities.

Also, of these markers, GPC4, GAGE2B and GAGE7 are also known as cancer-related markers. Therefore, this invention can also provide a way of assessing the "safety" (the propensity for tumorigenesis upon transplantation) of the given pluripotent stem cells by evaluating at least one marker out of GPC4, GAGE2B and GAGE7.

<Proteins, Nucleic Acids, Vectors and Cells of this Invention>

As described above, for the production method of PSC of this invention, the TET1 protein which is resistant to degradation in primed PSCs is useful. Therefore this invention provides a mutant TET1 protein having enhanced stability as compared to a wild type TET1 protein, preferably a mutant TET1 protein in which its second amino acid from the N-terminus is different from the second amino acid from the N-terminus of the wild type TET1 protein.

Moreover, the described amino acid sequence of SEQ ID NO: 4 or 6 which denote TET1 protein sequence first described by the inventors and are useful to prepare the mutant TET1 proteins as well as to provide a wild type TET1 protein to be used in the production method of this invention. Therefore, the present invention also provides these TET1 proteins.

Furthermore as described above, to express the mutant TET1 proteins having enhanced stability as compared to a wild type TET1 protein in the PSCs, the nucleic acids encoding such proteins are useful. Also, to prepare the mutant TET1 proteins and the nucleic acids encoding such proteins as well as to provide a wild type TET1 protein to be used in the production method of this invention, the nucleic acids which encode the amino acid sequences 4 or 6 of TET1 are also useful. Therefore, this present invention also provides such nucleic acids.

As mentioned above, to introduce the nucleic acids into somatic cells, it is preferable to insert the nucleic acid sequence into a vector. Therefore, this invention also provides vectors which bear a nucleic acid sequence coding the mutant TET1 protein with enhanced stability as compared to a wild type TET1 protein or a nucleic acid sequence encoding the amino acid sequence of SEQ ID NO: 4 or 6.

Moreover, according to the production method of this invention, as mentioned above, one can obtain a pluripotent stem cell with enhanced differentiation capacity. Therefore, this invention also provides pluripotent stem cells and/or somatic cells aimed to be induced to the stem cell which had been introduced by at least one molecule selected by the group (a) to (c) below:

(a) TET1 protein (b) a nucleic acid coding for TET1 protein (c) a vector into which a nucleic acid that encodes TET1 protein has been inserted

EXAMPLES

From here on, we are going to discuss our invention in details. However, the present invention is not restricted to the working examples shown below. The materials and methods used in these working examples are as follows.

<Human iPSC Production Using Episomal DNA Vectors>

The human iPSCs used in these working examples were derived using the method described by Okita K. et al. (Nat Methods, 2011, vol. 8, 409-412). Three pairs of reprogramming factors, namely a short-hairpin RNA against p53 (shp53) and POU5F1 (OCT3/4), SOX2 and KLF4, L-MYC and LIN28 are introduced in independent episomal pCXLE vectors and three vector DNAs were prepared.

In this process of the production of such iPS cells, cellular reprogramming which is a process to erase the cellular memories of the somatic cells was performed by overexpressing the so-called Yamanaka four factors (OCT3/4, SOX2, KLF4 and c-MYC). In these working examples, to decrease the likelihood of iPS cell-derived tumorigenesis which is an inherent characteristic of the introduced reprogramming factors, we have replace c-MYC by L-MYC, a reprogramming factor which is known to bear less tumorigenic property. Also, to enhance the efficacy of human iPS cell induction, LIN28 which is known to enhance induction efficacy of human iPS cells was also introduced to somatic cells. Also, as p53 acts to repress reprogramming, this factor was repressed by RNA interference (RNAi) against p53 using shp53.

If the reprogramming factors used to induce iPS cells are retained in the derived iPS cells during the course of producing of iPS cells, such iPS cells may exhibit some resistance against a certain differentiation signal such as neural induction (differentiation resistance) and have difficulty of gaining a novel cell memory. To this end, in these working examples, we chose episomal vector system to introduce genes which allow us to avoid genomic integration of the reprogramming vectors and persistent factor expression.

Next, the inventors introduced 1 μg of each the 3 vector DNA into $1.0\times10^5$ human neonatal fibroblasts using DNA transfection reagents (Human fibroblast Nucleofector™ kit) and a DNA transfection apparatus (Nucleofector™) (both from Lonza). Subsequently, the transfected cells have been maintained in E8 media, developed by Thomson et al., capable to induce iPS cells at a feeder-free condition (Chen, G et al., Nat Methods, 2011, Vol. 8, No. 5, pp424-429). During the first 5 to 10 days after transfection, hydrocortisone with fibroblast-proliferative activity was added to the E8 medium at a concentration of 100 nM, but afterward, both hydrocortisone and TGFβ were removed from the E8 medium to allow iPS cell reprogramming to occur. Cell culture media was replaced every one or two days and throughout this reprogramming process, cells were maintained in a hypoxic condition of 5% oxygen and 5% carbon dioxide within a hypoxic cell incubator.

Through these cultures, the authors were able to obtain multiple iPS cell colonies typically 25 to 30 days later after the introduction of vector DNA. Next, as will be mentioned afterward, the iPS cell colonies were individually picked up and cultured into a culture medium containing KnockOut Serum Replacement (KSR), Fibroblast Growth Factor 2 (FGF2), Activin A, ROCK inhibitor and Fibronectin and plated onto Collagen type I-coated culture dishes to isolate iPS cell clones. Examples of the obtained human iPS cell clones which were stably maintained and shown here are YMhiPSC058, YMhiPSC105 and YMhiPSC237.

When single cell-derived subclones from these original iPS cell clones were obtained and their differentiation potential were individually checked, the authors have found significant variations in the propensities of each subclones, which strongly suggests that the human iPS cell colonies induced as above are not homogeneous in terms of differentiation potential (data not shown). In the following working examples, results obtained from the YMhiPSC058sbc6 subclone, which exhibited the lowest differentiation biases among the obtained subclones, are displayed.

[Trituration Cell Passaging of Human iPS Cells at a Non-Feeder Condition]

In these working examples, human iPS cells were cultured in DMEM/F12 media (Kohjin-Bio) containing 20% KSR (Invitrogen), 15 ng/ml human FGF2 (Peprotech), 10 ng/ml heparin sulfate (SIGMA), 0.03% L-glutamine (MP Biochemicals), 1× non-essential amino acids (Invitrogen), 1× penicillin (Invitrogen) and 1× streptomycin (Invitrogen) (KFA medium hereafter), and maintained at a feeder-free condition.

At cell passaging, human iPS cells were single-cell triturated using 0.01% trypsin/0.1 mM EDTA and replated in KFA medium containing 2 μM ROCK inhibitor (Thiazovivin, WAKO) and 5 μg/ml human Fibronectin (BD Biosciences), followed by seeding onto a collagen type I-coated culture dish.

The non-feeder, trituration cell passaging method for human iPS cells has been independently established by the inventors themselves for the first time. This means that the inventors have performed pilot experiments to deduce adequate conditions which allow this non-feeder, trituration passaging of human iPS cells prior to these working examples. The reason why such pilot experiments were needed was as follows: The current lab routine for maintaining human ES cells or iPS cells alike uses mouse feeder cells which is relatively easy to keep the cells in an undifferentiated state. However, the authors have independently found that such cultures were rendering the stem cells more intractable to cell differentiation especially toward the neuroectoderm lineage. Moreover, although it is commonly accepted that trituration during human pluripotent stem cell passaging is more difficult, the inventors reckoned that such procedure is essential in controlling the cell density for proper cell differentiation.

Using a human iPS cell line (rvhiPSC08) reprogrammed by retrovirus-mediated expression of reprogramming factors (POU5F1, SOX2, KLF4 and c-MYC), the present inventors have addressed the following two points.

(1) the growth factor(s) to be added and its (their) concentration(s), and (2) the combination of the cell signaling inhibitors and the extracellular matrices to be used at the passage with trypsin.

At the time of these experiments, one of the conventional ways for culturing human pluripotent stem cells (PSCs) was to culture the cells in basal media supplemented chiefly with KSR, an Invitrogen reagent, and with human FGF2 at a concentration between 4 and 5 ng/ml and onto mouse embryonic fibroblast (MEF) feeders. In this circumstance, the MEF is supposed to provide the extracellular matrix and hence to help the attachability of PSCs onto culture surfaces but also to support cell growth by supplementing FGF2 and/or NODAL secreted by these cells, when judged by the published literature and the authors' own unpublished observations. Therefore, the inventors have investigated especially the effects of FGF2 and Activin A with NODAL-like activity to be added on top of KSR to their media. They have investigated the concentrations of FGF2 and Activin A by assessing the expression of markers such as POU5F1, SOX2 or NANOG which indicate the undifferentiated status, a mesendodermal marker T (also known as BRACHYURY) and a neuroectodermal marker SOX1. The inventors have come up with final concentrations of approximately 15 ng/ml for FGF2 and 10 ng/ml for Activin A which gave best results in stable cell proliferation of these cells, and by using KFA medium, the inventors succeeded in easily culturing human iPS cells at a non-feeder fashion.

Although the routine passaging procedure was to loosely detach human iPS cell colonies enzymatically which gave cell aggregates of average size of several tens of cells, from the viewpoints presented earlier, the inventors went on to devise a way to allow such cell trituration. It has been known that human ES cells could be single-cell passaged using ROCK inhibitors (Watanabe, K. et al., Nat Biotechnol., 2007, Vol. 25, No. 6, pp 681-686; Lin, T. et al., Nat Methods, 2009, Vol. 6, No. 11, pp 805-808). However, in these known literatures, the use of artificial extracellular matrices such as MatriGel for coating a culture dish is mandatory and therefore these methods were not user-friendly. The inventors have found a paper in which such use of artificial extracellular matrices is replaced by fibronectin which could be added directly into the culture medium to help trituration passaging (Kitajima, H. et al., Biochem Biophys Res Commun, 2010, Vol. 396, No. 4, pp 933-938). Collectively, the present inventors have deduced that by combining the KFA media, ROCK inhibitor and fibronectin to maintain human iPS cells after trypsin-single-cell passaging in collagen type I-coated culture dishes would be a feasible culture methods which finally led them to establish their own non-feeder, trituration-passaging culture method of the cells.

[Quantitative RT-PCR]

RNA was extracted using RNeasy mini kits (QIAGEN). To avoid genomic DNA contamination, RNase-free-DNase set (QIAGEN) was also used for DNase treatment. Using 1 μg of total RNA as a template, cDNA was reverse-transcribed using oligo-dT primer (TOYOBO) and Revertra Ace (TOYOBO). The cDNA was diluted 20 times in distilled water and quantitative PCR (qPCR) was performed using Fast SYBR green master mix reagent (ABI) and primers listed in Table 1 on an ABI apparatus. For each RNA sample, a triplicate of reactions were performed to obtain each mean value and values normalized against GAPDH internal controls were shown as graphs (FIGS. 2, 5, and 8-23).

TABLE 1

| Gene name of | Forward primer | | Reverse pritmer | |
|---|---|---|---|---|
| amplification target | Sequence | SEQ ID NO: | Sequence | SEQ ID NO: |
| GAPDH | agccacatcgctcagacac | 11 | gcccaatacgaccaaatcc | 12 |
| POU5F1 | ctttgaggctctgcagcttag | 13 | tctgctttgcatatctcctgaa | 14 |
| SOX2 | gggggaatggaccttgtatag | 15 | gcaaagctcctaccgtacca | 16 |
| NANOG | tctccaacatcctgaacctca | 17 | ttgctattcttcggccagtt | 18 |
| T(Brachury) | gctgtgacaggtacccaacc | 19 | catgcaggtgagttgtcagaa | 20 |
| SOX1 | ggctgagcaccactacgact | 21 | gcattataaaatttcccaaatcatc | 22 |
| PAX6 | atttcccgctctggttcag | 23 | gttttctccacggatgttgc | 24 |
| SOX17 | acgccgagttgagcaaga | 25 | tctgcctcctccacgaag | 26 |
| MIXL1 | ggtaccccgacatccactt | 27 | gcctgttctggaaccatacct | 28 |
| NEUROGENIN1 | ccgcttgttaggtcgccgca | 29 | tgggctgagggccggagaaa | 30 |
| NEUROGENIN2 | acacgcaccaccaccacaaca | 31 | ccggcgagtttgccaagagc | 32 |
| ASCL1 | cgacttcaccaactggttctg | 33 | atgcaggttgtgcgatca | 34 |
| ZNF521 | tgggatattcaggttcatgttg | 35 | actggagtttggcaggagag | 36 |

TABLE 1-continued

| Gene name of amplification target | Forward primer Sequence | SEQ ID NO: | Reverse pritmer Sequence | SEQ ID NO: |
|---|---|---|---|---|
| NUROD1 | gcggccacgacacgaggaat | 37 | cgcccatcagcccactctcg | 38 |
| TET1 | ccaagccccagaagattag | 39 | tggagctaatcgtgtag | 40 |
| DNMT3A | ggtgcactgaaatggaaagg | 41 | actggcacgctccatgac | 42 |
| DNMT3B | ggtgcactgagctcgaaag | 43 | aagaggtgtcggatgacagg | 44 |

[Western Blotting]

To reproducibly detect TET1 protein using Western blotting, the authors have performed sets of pilot experiments to optimize the method for protein extraction. It turned out that Tet1 molecules were strongly bound to DNA. The inventors have found that by cell-fractionating cell nuclei followed by protein extraction using NER solution (PIERCE) allowed them to quantitatively detect TET1 protein. It was known later that TET1 protein binds to DNA with an unprecedented affinity, which may explain the requirement of such special extraction method.

For western blotting, protein was extracted with the method and was size-fractionated using SDS-PAGE followed by electro-transfer onto a PVDF membrane. Anti-human TET1 antibody (SIGMA) and anti-human β-actin antibody (SANTA CRUZ) were diluted ×1,000 in 0.3% Triton-X100, 3% BSA and 1% normal-goat serum in PBS(−) (antibody diluting solution). Next, the membrane was incubated in the diluted primary antibody solution overnight at 4° C. After stringent washing, the membrane was incubated with HRP-conjugated secondary antibody at room temperature for one hour. After washing, ECL (GE Healthcare) was reacted with HRP present on the membrane surface, and the resulting fluorescence was developed on a film.

[Neural Differentiation of Human iPS Cells]

The neural differentiation of human iPS cells were basically performed according to the improved protocol the inventors have previously developed for mouse ES cells in that these cells efficiently differentiated to neurons (Bouhon, I. et al., Brain Res Bull, 2005, vol. 68 (1-2), pp. 62 to 75). The details are as follows:

(1) Adaptation Culture

Before each cell differentiation, human iPS cells routinely maintained in KFA at a feeder-free condition were transferred to a CDM-based medium, a step which the authors call adaptation culture. The novel CFA medium used for this adaptation culture consists of CDM medium supplemented with 40 ng/ml human recombinant FGF2 and 2 ng/ml human recombinant Activin A and was developed herein especially to switch the human PSCs from maintenance culture to neural differentiation. The details of the CDM medium can be found in Bouhon, I A et al., Brain Res Bull, 2005, Vol. 68 (1-2), pp 62-75. As cells are slightly more vulnerable to oxidative stress originated from atmospheric oxygen in this culture medium, this adaptation culture was performed in a low-oxygen $CO_2$ incubator (hypoxic condition: oxygen concentration 5%).

(2) Neural Precursor Cell Differentiation of Human iPS Cells

When confluency is attained, CFA-cultured human iPS cells were dissociated with trypsin treatment as mentioned above and resuspended at a cell density of $5\times10^4$ cells/ml in CDM medium supplemented with 10 μM Y27632 (a ROCK inhibitor) and plated down onto a low-attachment culture dish (bacterio-grade Petri dish).

Four days after the induction of differentiation, the formed cell aggregates ("spheres" hereafter) were collected and were single-cell dissociated back with Accutase (BD Biosciences). The dissociated cells were then transferred to the neural induction medium (10 μM SB431542, 30 nM IWR-1endo and 10 μM Y276732 in CDM) and plated onto Petri dishes as above. After additional four days, the collected spheres were dissociated as above and resuspended in CDM containing 10 μM SB431542 and 10 μM Y27632.

In the above procedure, SB431542 and IWR-1endo were deliberately added to the original CDM differentiation medium by taking into account the difference between mouse ES cells and human PSCs. This is because from the naïve mouse ES cells, a primitive endoderm cell population can be derived which can become a source of expressing antagonizing factors against the anti-neural TGFβ/Nodal and WNT signaling according to the inventors' previous reports. In contrast, primitive endoderm cells cannot be normally induced from human PSCs and therefore their differentiation toward neural cells would be expected to be defective if the mouse ES cell neural differentiation protocol is applied without modification. Therefore in order to assess the neural differentiation potentials of the given human iPS cells in the following Examples, the inventors have deliberately added the small molecule SB542431 to block the TGFβ/Nodal signaling and IWR-1endo, a WNT signaling antagonizing small molecule to their neural differentiation media.

After the cells were treated in CDM supplemented with SB542431 and Y27632, at similar intervals, the spheres were passaged in CDM plus Y27632 or passed to the maturation procedure as follows. In the inventors' hands, maintaining the differentiated neural precursors in CDM did not let these cells mature into neurons but kept proliferating as precursors.

(3) Maturation of Neurons

Neurons are post-mitotic and therefore do not divide anymore. With the neural differentiation protocol, proliferating neural precursor cells could be differentiated out of human PSCs. To obtain functional post-mitotic neurons with characteristic neurites, we have to keep these cells individually attached onto substrates on the bottom of a culture dish out of the formed precursor spheres (This step whereby the precursors are let to mature in a culture dish into neurons can be called as "neuron-maturation culture").

At the neuron-maturation culture, culture dish surfaces were transferred from non-attaching Petri dish plastic to neuron-permissive collagen type IV (IWAKI). For culture, the inventors have further pre-treated it with poly-L-ornithine (SIGMA) and recombinant laminin (BD Biosciences) for a certain period of time. The spheres were dissociated using Accutase as mentioned earlier. Moreover, during this maturation culture, cells were maintained in CDM containing 3 μM CHIR99021, 10 μM DAPT and 10 μM forskolin. The culture medium was replaced every second day, and after about a week, neurons with prominent neurites were observed.

Working Example 1

<Endogenous TET1 Dynamics in Human Pluripotent Stem Cells>

The mouse PSCs bear similar characteristics of the pre-implantation blastocyst's inner cell mass. In contrast, human PSCs are most akin to the post-implantation epiblast's primitive ectodermal cells. From this difference in developmental stages, it is generally assumed that human PSCs are less pluripotent than mouse PSCs. Therefore, the inventors aimed to enhance the pluripotency of human PSCs by further de-differentiating (or reprogramming) these cells from an epiblast-like (primed) state toward a blastocyst-like (naive) state.

During development, there are two kind of reprogramming. One occurs from fertilization to implantation and called the "early embryonic reprogramming" and the other occurs after implantation during the specification of the germline which is called the "germline reprogramming". From these, the inventors considered that the cell memories acquired during the process of blastocyst to epiblast transition should be erased and have come up with TET1 which seemed to be a strong candidate after examining various factors expressing during the "early embryonic reprogramming".

The expression profile for Tet1/TET1 in mammals is only reported for mice. According to these information, mouse Tet1 is known to be expressed during the early development within the nuclei of the fertilized eggs up to blastocysts (Ito S., Nature, 2010, vol. 466, 1129-1133). Another paper described this factor is also expressed specifically in the primordial germ cells in which the germ cells are specified (Hajkova P., Science, 2010, vol. 329, 78-82). Moreover, Tet1 protein is also abundantly expressed in mouse ES cells which are derived from the Tet1-expressing blastocysts. However, there was no information available about the expression profile of the human TET1 thus far.

First, the inventors investigated the expression of TET1 mRNA and protein in human iPS cells. For the detection of TET1 protein, the inventors have noticed that this protein is strongly bound to DNA and therefore exploited a strong elution method which for the first time allowed them to quantitatively detect this protein by western blotting. The results are shown in FIGS. 1 and 2.

Figure 2:
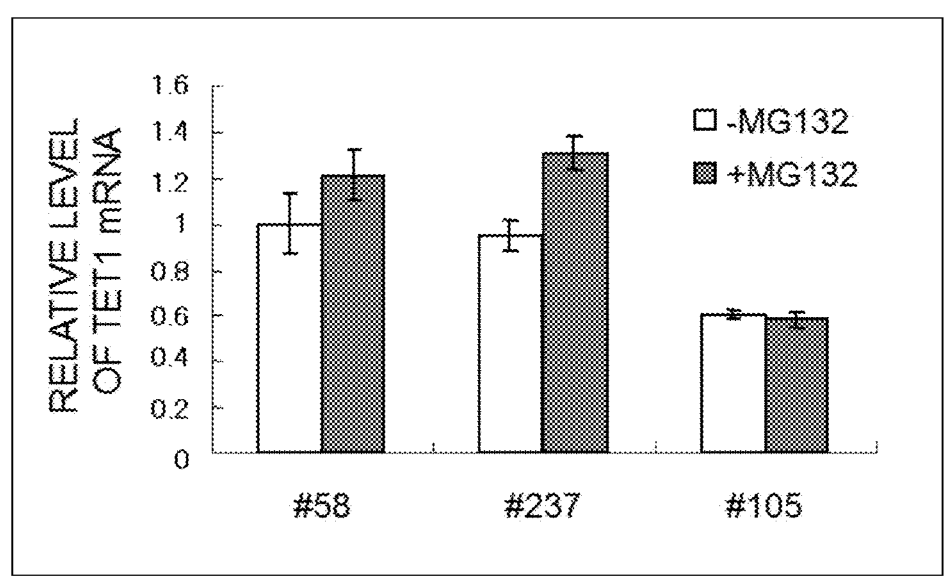
FIG. 2 The graph shows the result of the quantitative RT-PCR for analyzing the expression amount of TET1 mRNA in individual human iPS cells (#58, #237 and #105) with or without proteasome inhibitor (MG132). On the vertical axis are represented relative mean values of each sample in triplicates when normalized against GAPDH expression values of the same sample. Error bars represent standard deviations (so are in FIGS. 5, 8 to 23).

As clearly shown in FIGS. 1 and 2, albeit the fact that TET1 is expressed at the transcript level, its protein was not detected in normal conditions, a situation which contrasts to the one observed for mouse ES cells.

Therefore, the inventors went on to transiently inhibit the function of the major protein degradation pathway, the proteasome, and tried to detect TET1 with western blotting. Independent human iPS cell lines (#58, #237 and #105) were cultured in KFA medium in a routine fashion but 7 hours before nuclear extract sampling, the cells were treated with MG132 5 μM with 0.1% of DMSO as a solvent and processed for western blots. As control, cells were also treated with 0.1% DMSO alone for 7 hours before nuclear extraction and processed for western blots.

As shown in FIGS. 1 and 2, TET1 being actively transcribed in human iPS cells, was swiftly degraded at the protein level through the proteasome system. Upon MG132 treatment, although the transcription levels of TET1 were also up-regulated, these were clearly not causative of the drastic changes observed at the protein levels. Together, these results indicate that human PSCs under a normal condition do not bear TET1 protein or otherwise, its protein level in these cells stayed under the detection limit by western blots.

Working Example 2

<Determination of the Structure for Human TET1 Gene>

As has been clearly shown in the Working example 1, TET1 protein was not stabilized in human PSCs. When considering the process of human iPS cell induction, it is unlikely that the cells in the process have spent enough time under conditions similar to blastocyst- or germline-stage embryos where TET1 protein can be stably expressed and therefore, in this induction process, it is feasible to think that TET1 activity has not been sufficiently transferred to the genome. It is also noticeable that this presence or absence of TET1-genome interaction may be decisive for the difference in the differentiation efficacies between the naive mouse PSCs and the primed human PSCs.

In order to forcefully express TET1 protein in human PSCs, the inventors sought to obtain the full-length cDNA encoding human TET1 by RT-PCR. Using a human iPS cell line (rvhiPSC08), the inventors obtained the TET1 cDNA by RT-PCR using PrimeSTAR Max DNA polymerase (Takara Bio). In this step, according to the available TET1 cDNA sequence (Refseq: NM_030625), the inventors designed their PCR primers so that they can express TET1 protein which would bear FLAG tag either at its N-terminus or C-terminus as shown below and used them for RT-PCRs.

(N-Terminus FLAG Primers)

```
XhoI-Flag-hTet1-S:
                                        (SEQ ID NO: 7)
GCAAGAATTCCTCGAGCCACCATGGACTACAAAGACGATGACGACAAGTC

TCGATCCCGCCATGCAAG

XhoI-hTet1-AS:
                                        (SEQ ID NO: 8)
GAGTGAATTCCTCGATCAGACCCAATGGTTATAGGGCC

(N-terminus FLAG primers)

XhoI-hTet1-S:
                                        (SEQ ID NO: 9)
GCAAGAATTCCTCGAGCCACCATGTCTCGATCCCGCCATGC

XhoI-hTet1-Flag-AS:
                                       (SEQ ID NO: 10)
GAGTGAATTCCTCGATTACTTGTCGTCATCGTCTTTGTAGTCGACCCAAT

GG
```

Figure 3:
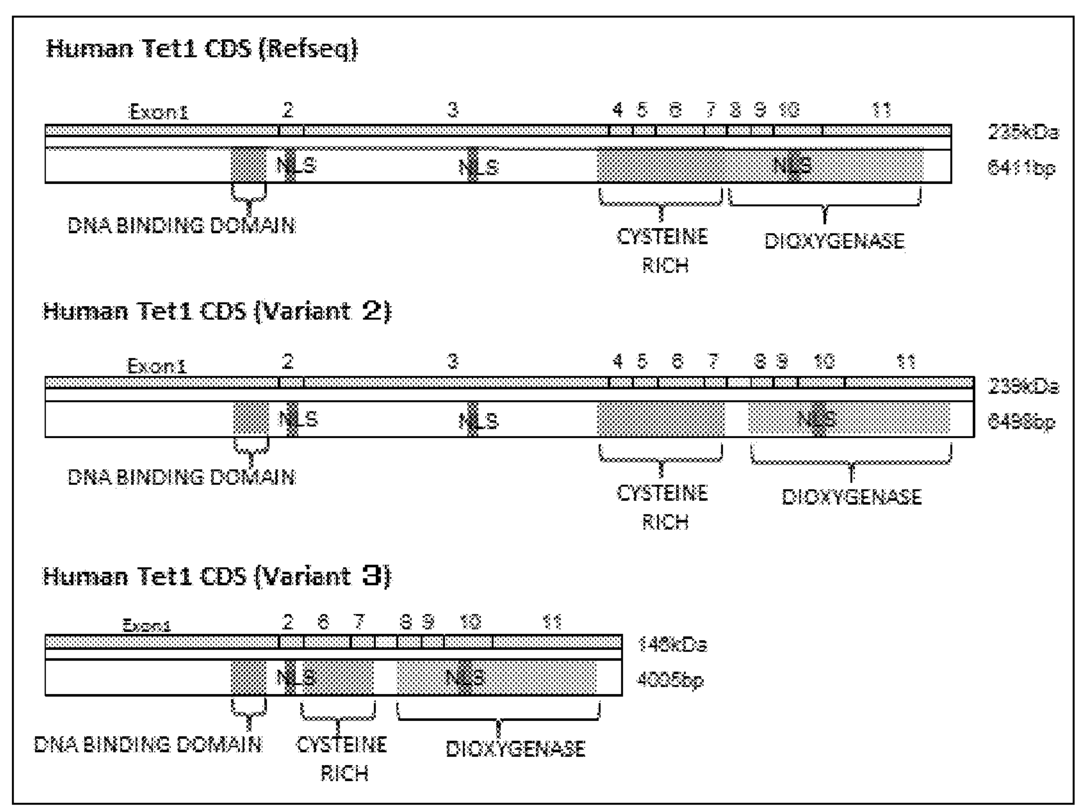
FIG. 3 The structures of the three TET1 proteins expressed in human iPS cells. At the top are shown the TET1 gene coding region (CDS) from the sequence deposited as Refseq and protein structures encoded by the CDS. At the middle and bottom are the two TET1 splice variants' CDSs and protein structures encoded by the CDSs.

The results of these RT-PCR, as depicted in FIG. 3, showed two PCR products both of which turned out to be TET1 variants but differed from the Refseq sequence (human TET1, variant 1), and therefore these two variants represent novel splice variants in PSCs.

The longer of the novel variants (human TET1, variant 2), when compared to the Refseq sequence, bears an additional sequence between the $7^{th}$ exon and the $8^{th}$ exon with a length of 87 bases. The exon sequence was confirmed to be a single exon from the comparison with the genomic sequence. This part of the TET1 protein corresponds to the N-terminal portion of the catalytic (dioxygenase) domain of TET1 deduced by crystallography. Interestingly, the corresponding exon is present in the mouse Tet1 sequence.

The shorter of the novel variants (human TET1, variant 3) turned out to miss the third to the fifth exons. As these three exons consist of 2493 base pairs, this deletion is supposed to be an in-frame deletion. Within the portion missing in variant 3 when compared to variants 1 and 2, it is reported that two nuclear localization signals are present.

Although not presented here as a figure, variant 2 appeared to be the majorly expressed form in human iPS cells by RT-PCR. In contrast, variant 1 expression, albeit in a more limited amount, was also detectable in human iPS cells. Variant 3 was also expressed in a modest way. Also not shown as a figure was the fact that all three corresponding variants were detectable in the mouse at the mRNA level.

In the sequence listing are shown: human TET1 variant 1 sequence as SEQ ID NO: 1 and the amino acid sequence encoded by this as SEQ ID NO: 2; human TET1 variant 2 sequence as SEQ ID NO: 3 and the amino acid sequence encoded by this as SEQ ID NO: 4; human TET1 variant 3 sequence as SEQ ID NO: 5 and the amino acid sequence encoded by this as SEQ ID NO: 6.

Working Example 3

<Expression of the Mutant TET1 Protein: Part 1>

The inventors have tried in expressing human TET1 (variant 2) which was amplified in the Working example 2 in human PSCs by introducing it in human PSCs.

As mentioned previously, N-terminal or C-terminal FLAG tag-containing TET1 cDNAs were amplified using human iPS cell cDNA as template using RT-PCR. The obtained 2 modified TET1 cDNAs were then independently inserted into a XhoI site in a mammalian expression vector (pCAG-ires-puro; a gift from Niwa lab at RIKEN CDB) using In-fusion HD cloning kit (Takara Bio).

Next, these expression vectors were independently transfected into the human iPS cell line (YMhiPSC058 subclone) using Nucleofector. The transfection was performed by suspending iPS cells with Human Stem Cell Nucleofector Kit 1 (Lonza) and applying electric pulse under the program B-016 which was previously shown to exhibit highest transfection efficiency toward human iPS cells.

The aforementioned expression vectors were introduced into human iPS cells and by selecting the transfected cells under the pressure of puromycin (1 μg/ml), the inventors obtained several stable transformants for both N-terminal and C-terminal FLAG-tagged TET1 clones. TET1 mRNA and protein expression levels were analyzed and shown in FIGS. 4 and 5.

Figure 4:
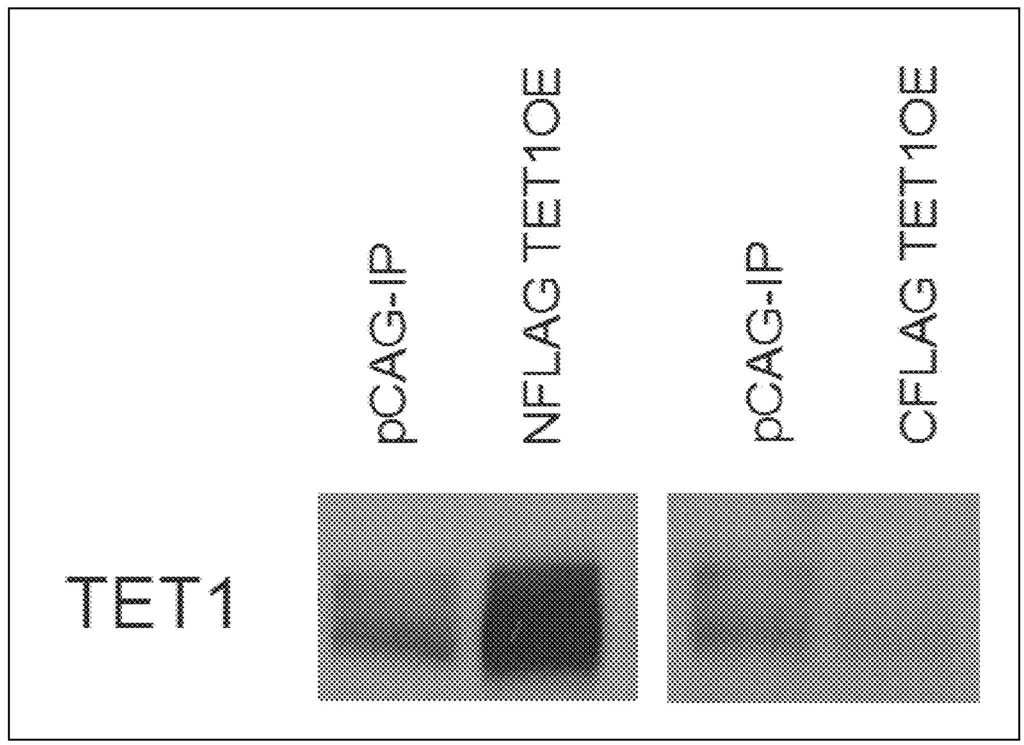
FIG. 4 The picture shows the result of the western blot for analyzing the expression amount of TET1 in control human iPS cell line which expresses a mock vector (pCAG-IP), a human iPS cell line expressing an N-terminally FLAG-tagged (NFLAG TETOE) and a human iPS cell line expressing a C-terminally FLAG-tagged (CFLAG TETOE).
Figure 5:
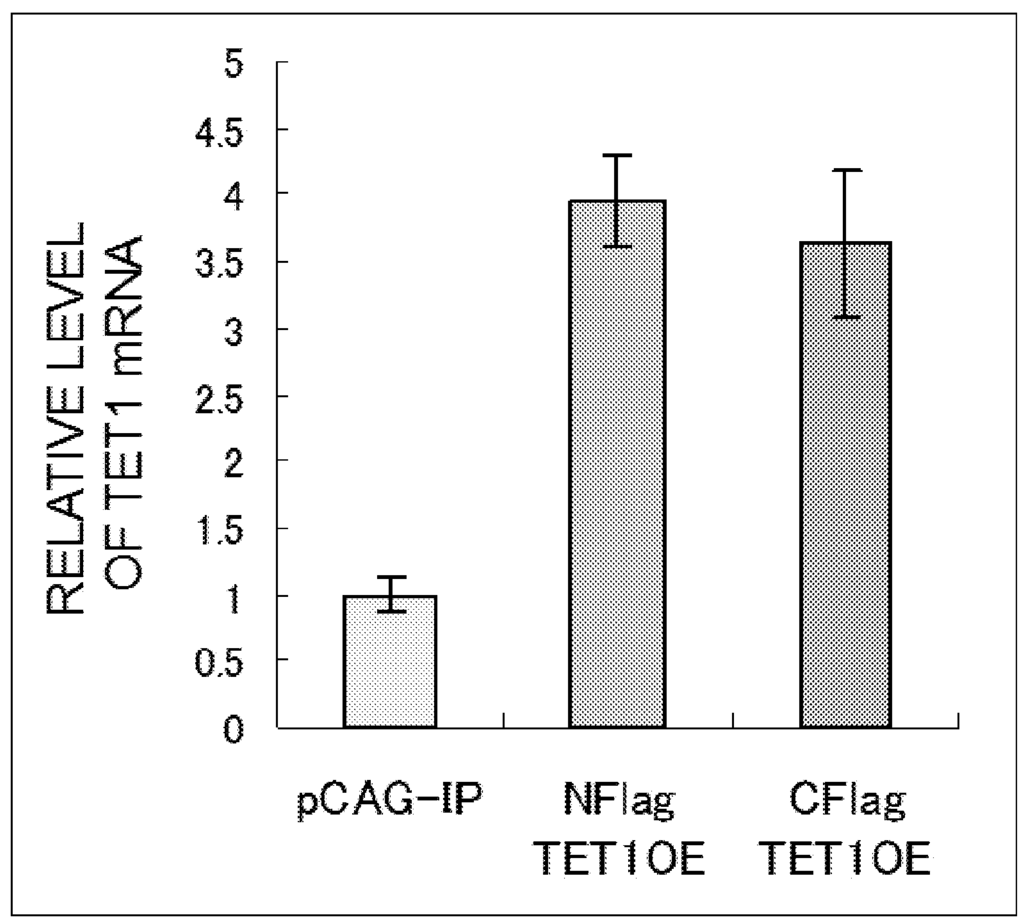
FIG. 5 The graph shows the result of quantitative RT-PCR for analyzing the expression amount of TET1 mRNA in NFLAG TET1OE, CFLAG TET1OE and pCAG-IP.

As clearly shown in FIGS. 4 and 5, TET1-expressing clones of both tags exhibited significant increases of TET1 transcription (FIG. 5). However, very interestingly, TET1 protein signal detection by western blots only showed TET1 band from the N-terminal FLAG-tagged TET1 clones (FIG. 4). This suggests that a degradation signal for TET1 protein is present at its N-terminal end.

Working Example 4

<Expression of the Mutant TET1 Protein: Part 2>

According to the results obtained in the Working example 3, the inventors evaluated the stability of the mutant TET1 protein for identifying a sequence involved in destabilization of the TET1 protein as follows.

The N-terminal portion of TET1 protein (about 600 amino acids) were fused through its C-terminus to a GFP resulting a mutant TET1 protein which was expressed in human iPS cells by the aid of Nucleofector. The GFP used in this example (Tag-GFP; Evrogen) has a shorter translation-coloring time lag compared to the conventional GFP which allows a real-time analysis of the appearance-disappearance dynamics of the fused protein.

Figure 6:
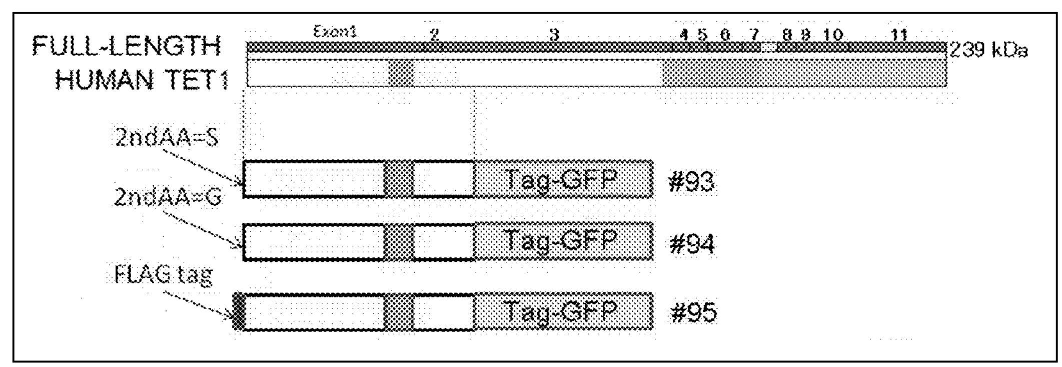
FIG. 6 Schematic figure showing the structures of the mutant TET1 proteins which were used to show the relationship between the stability and the modification in TET1 protein. At the top is shown the CDS of the human TET1 gene for the variant 2 and the protein structure encoded by the CDS. Second from the top is shown the structure for a fusion protein of the N-terminal portion of the human TET1 protein (the protein consisting of 670 amino acids) fused to GFP (#93). At the third position from the top is shown the structure for a fusion protein of the N-terminal portion of the human TET1 protein (the protein consisting of 670 amino acids) with the second amino acid serine converted to glycine, fused to GFP (#94). At the fourth position from the top is shown the structure for a fusion protein of the N-terminal portion of the human TET1 protein (the protein consisting of 670 amino acids) with a FLAG tag inserted between the first methionine and the second serine, fused to GFP (#95).

As shown in FIG. 6, the fused mutant TET1 proteins are, the wild-type TET1 N-terminal portion fused to Tag-GFP (#93), a TET1 protein N-terminal portion in which its second amino acid form the N-terminus (S: serine) has been experimentally switched to G: glycine and then fused to Tag-GFP (#94) and finally, as described in the Working example 3, TET1 N-terminal portion with a stabilizing N-terminal FLAG tag fused to Tag-GFP (#95). These were independently introduced into iPS cells. It was confirmed that all these GFP fluorescence emanating from the fused proteins were discernible within the cell nuclei of the transfected cells. To quantitatively analyze the fluorescent intensities of the individual expression constructs in each cell, human iPS cells expressing each mutant TET1-fusion protein were analyzed by FACS analyses. The results are shown in FIG. 7.

Figure 7:
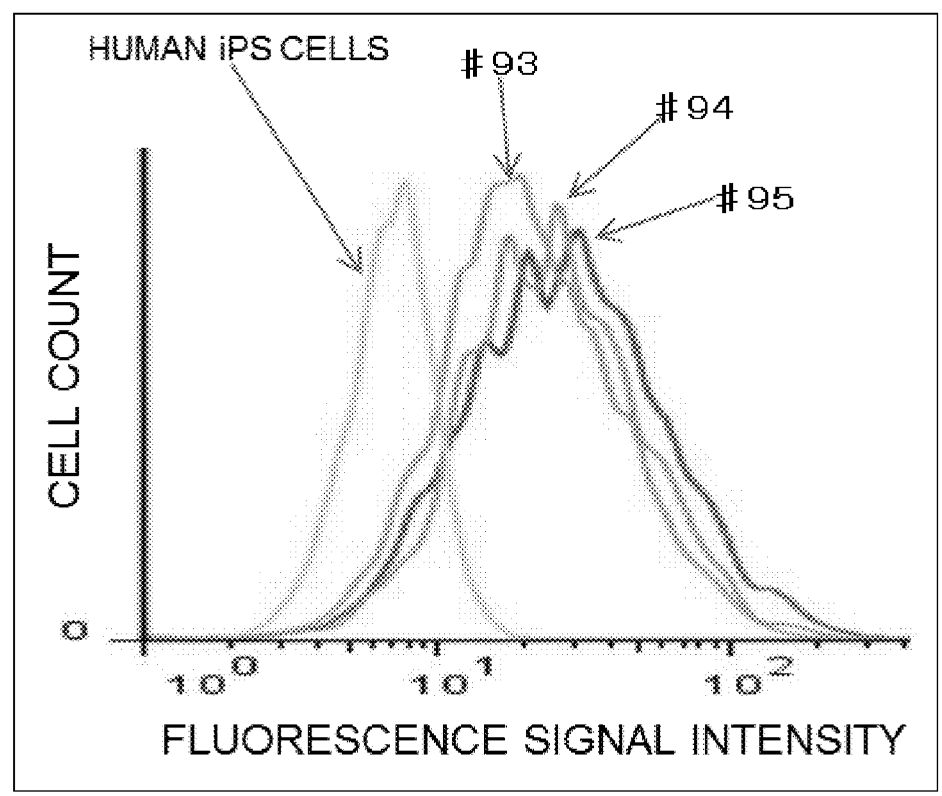
FIG. 7 A histogram showing FACS result obtained from the hiPSCs bearing the GFP-fusion protein depicted in FIG. 6 independently (#93, #94 and #95). The histogram depicted as "hiPSC" represents a negative control using human iPS cells with no GFP expression.

As clearly depicted in FIG. 7, the geometric means of the auto-fluorescence signals of the negative control non-GFP expressing iPS cells was 7.2. The geometric means of the wild-type TET1 N-terminal portion-GFP fusion expressing iPS cells (#93) was 26.3. In contrast and interestingly, the fluorescence intensity jumped up for the fusion protein in which the second amino acid from the N-terminus of TET1 was switched from serine to glycine (signal intensity: 31.6; #94 in FIG. 6). Moreover, as expected from the results shown in the Working example 3, in case where the inventors have replaced the first methionine of the wild-type TET1 by a FLAG tag, the signal intensity was significantly increased (signal internsity: 37.7; #95 in FIG. 6).

Therefore, it was concluded that the second amino acid from its N-terminus, serine, is critical in determining the stability of this protein. According to this result, it would be possible to deduce that the observed enhanced stability of the TET1 protein in the Working examples 3 and 4, where its second amino acid from its N-terminus has been replaced from serine to the second amino acid of a FLAG tag, an aspartate, was operational for this change (for the amino acid sequence of a FLAG tag, refer to SEQ ID NO: 46).

Working Example 5

<Analyses of Human iPS Cells Overexpressing the Mutant TET1 Protein (TET1-hiPSC) at their Undifferentiated State>

As been shown in the Working example 1, TET1 protein is not normally expressed in the human PSCs which are presumed to be equivalent to an epiblast-like embryonic stage. Therefore, the human iPS cells overexpressing the mutant TET1 protein (TET1-hiPSCs) can be assumed that these cells do not exist during development.

Although it is not shown as a Figure, surprisingly, TET1-hiPSC cultured in KFA medium, when maintained in an undifferentiated state, does not exert any physiological difference such as cell morphology or cell growth when compared to conventional human iPSC which does not express the mutant TET1 protein and is rather identical in appearance. Therefore, the inventors have tried to evaluate the TET1-hiPSC using the expressivities of mRNA for transcription factors which are thought to be strongly correlated with the characteristics of PSCs by RT-PCR. The obtained results are shown as "Day 0" in FIGS. 8 to 23.

Figure 8:
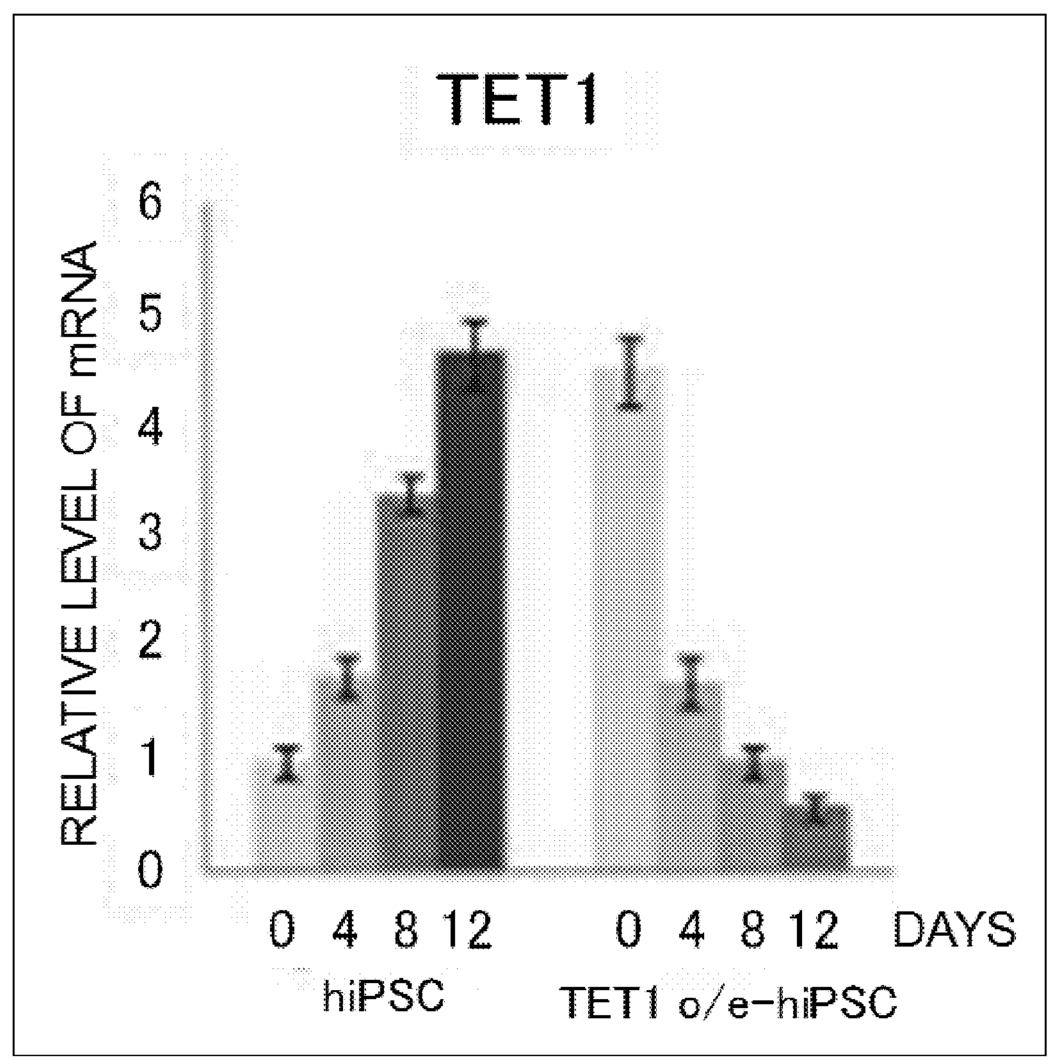
FIG. 8 The graph shows the time course of TET1 mRNA expression during the neural induction of control human iPS cell (depicted as "hiPSC" in the figure) and human iPS cell expressing N-terminally FLAG-tagged TET1 protein ("TET1o/e-hiPSC"). The vertical horizontal axis of the graph represents the days after the commencement of neural induction (also in FIGS. 9 to 23).
Figure 9:
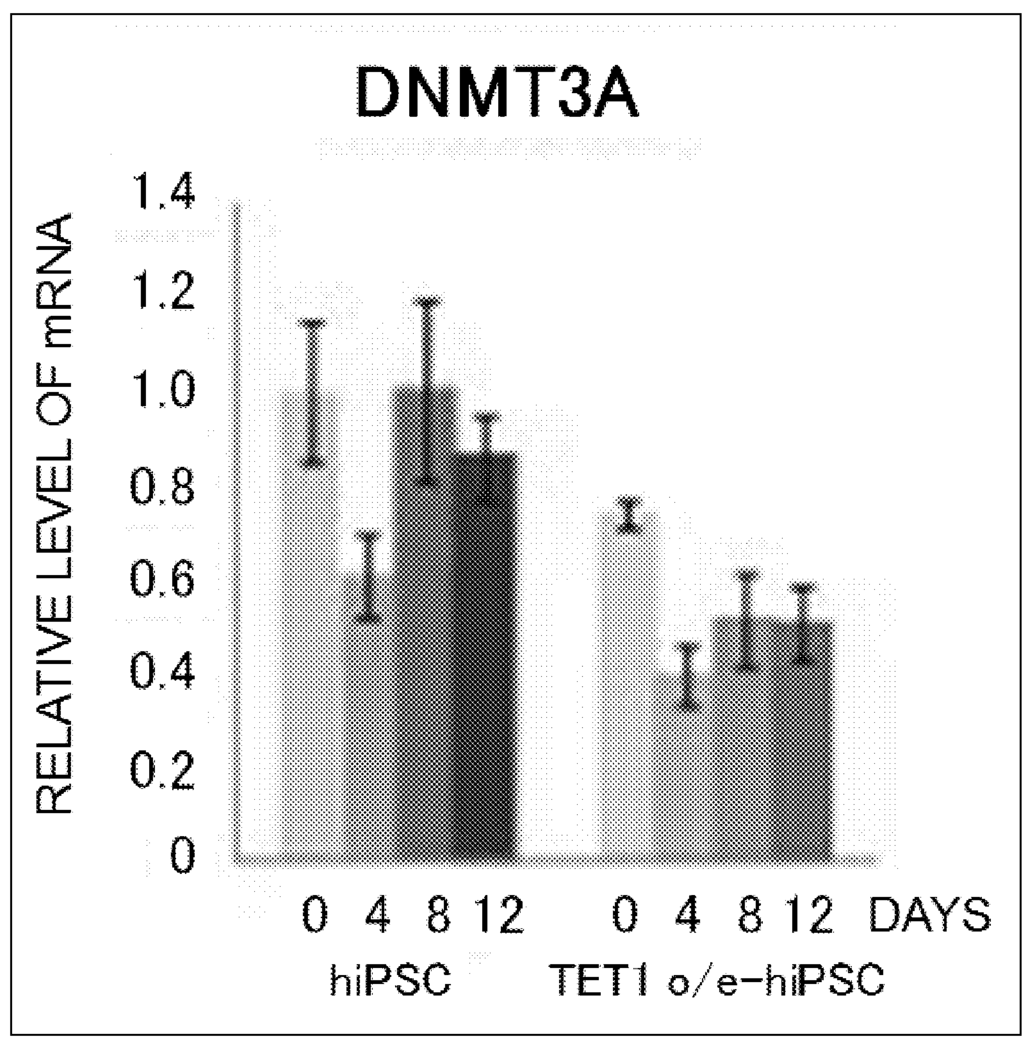
FIG. 9 The graph shows the time course of DNMT3A mRNA expression during the neural induction of hiPSC and human iPS cell expressing N-terminally FLAG-tagged TET1 protein.
Figure 10:
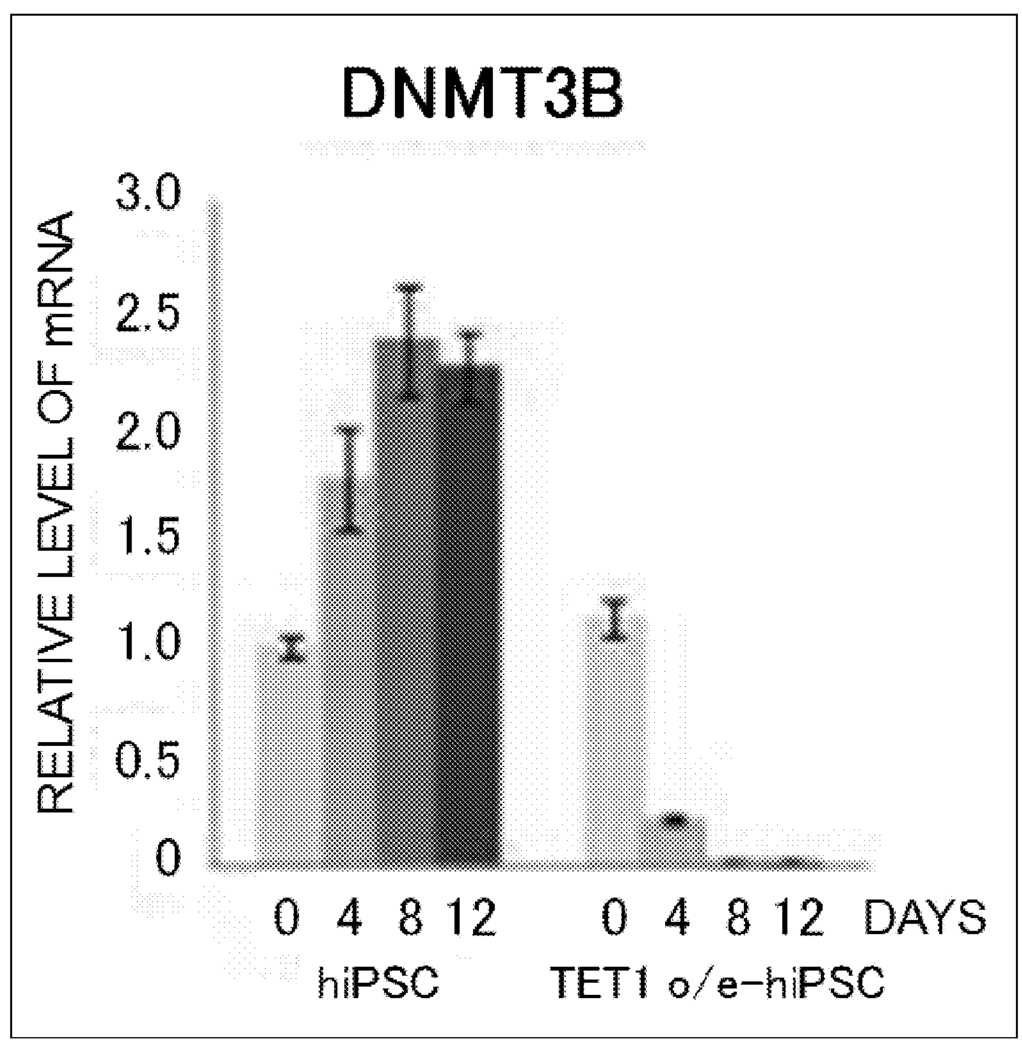
FIG. 10 The graph shows the time course of DNMT3B mRNA expression during the neural induction of hiPSC and human iPS cell expressing N-terminally FLAG-tagged TET1 protein.
Figure 11:
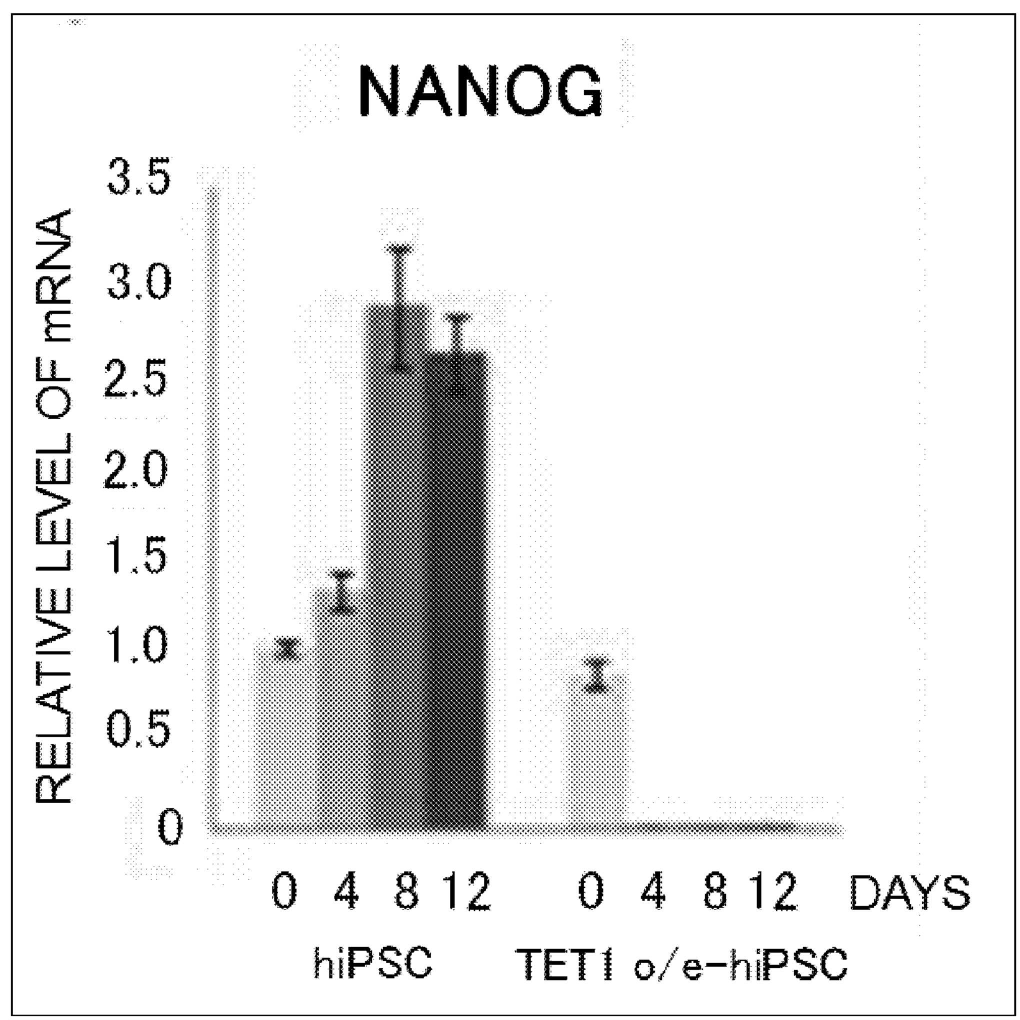
FIG. 11 The graph shows the time course of NANOG mRNA expression during the neural induction of hiPSC and human iPS cell expressing N-terminally FLAG-tagged TET1 protein.
Figure 12:
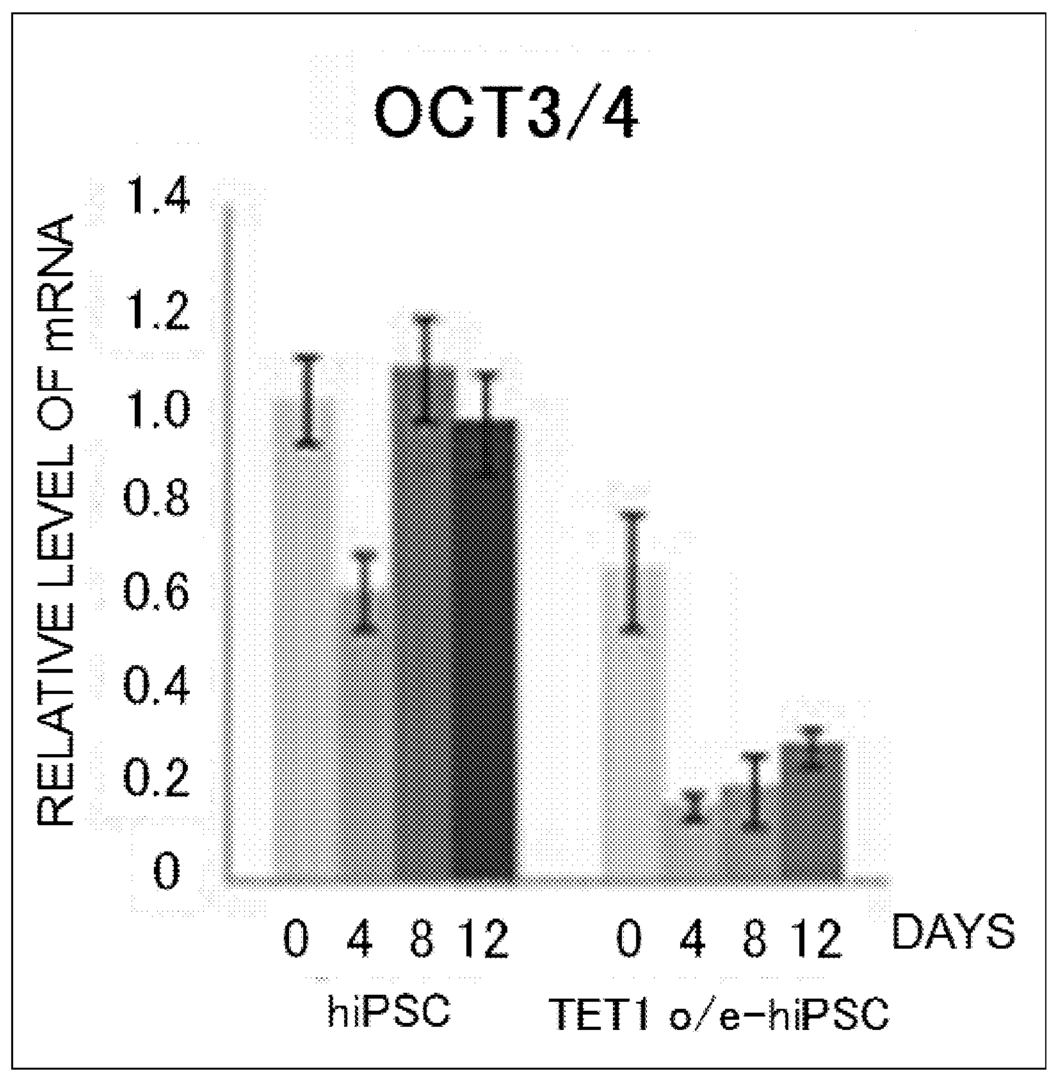
FIG. 12 The graph shows the time course of OCT3/4 mRNA expression during the neural induction of hiPSC and human iPS cell expressing N-terminally FLAG-tagged TET1 protein.
Figure 13:
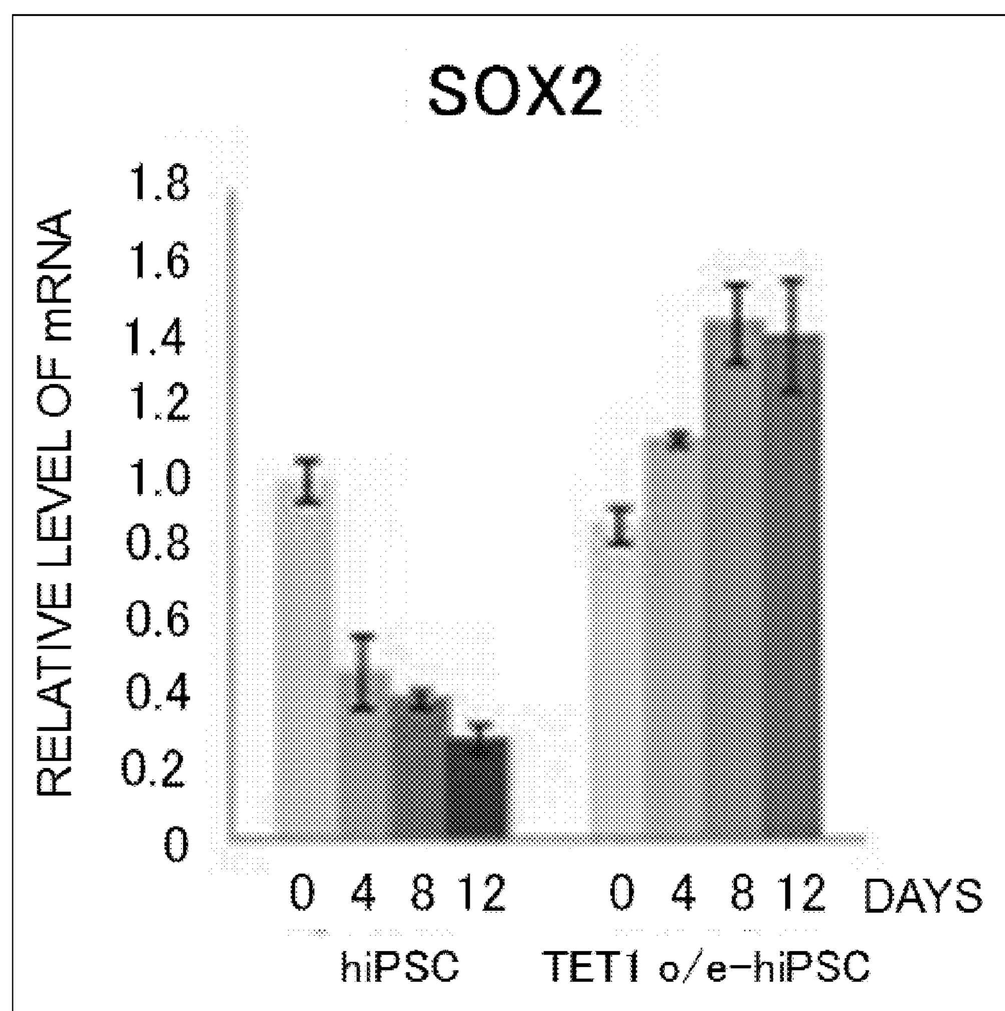
FIG. 13 The graph shows the time course of SOX2 mRNA expression during the neural induction of hiPSC and human iPS cell expressing N-terminally FLAG-tagged TET1 protein.
Figure 14:
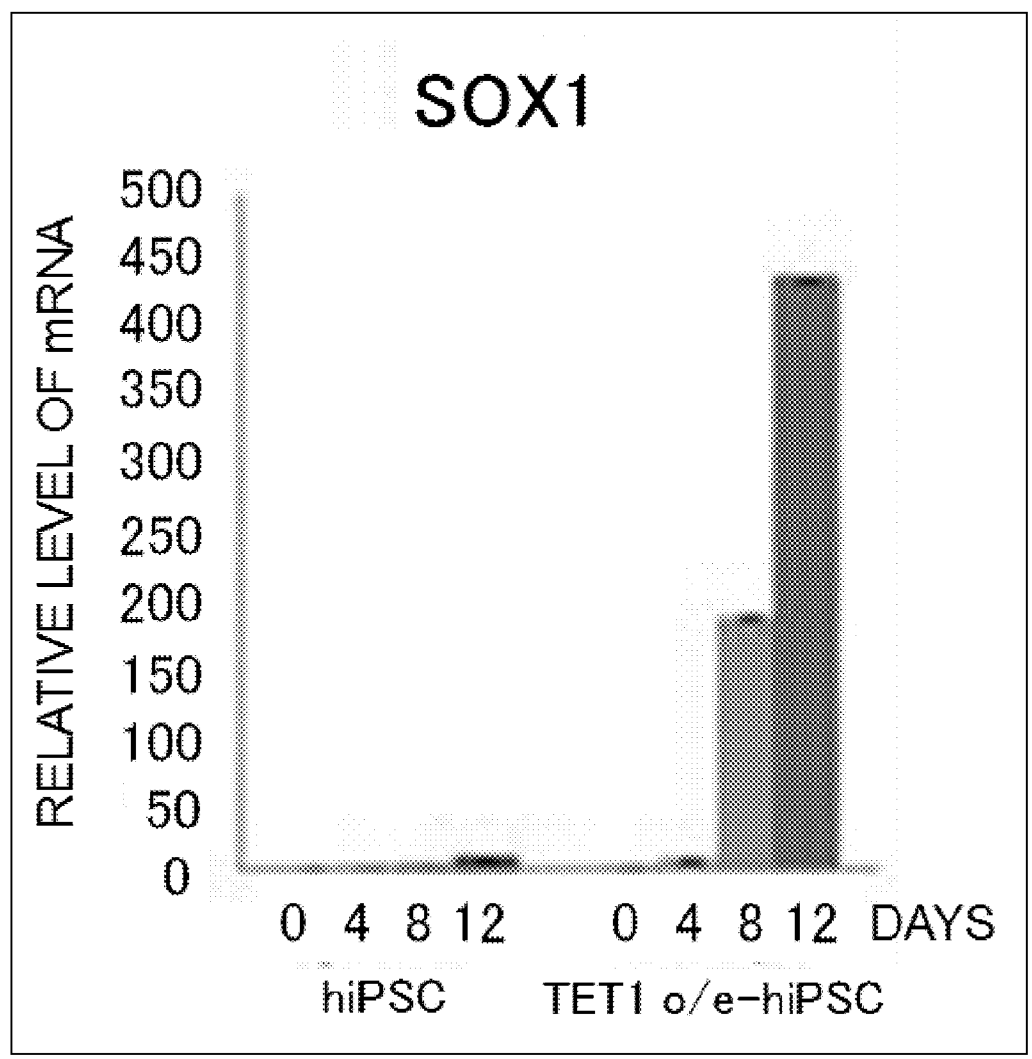
FIG. 14 The graph shows the time course of SOX1 mRNA expression during the neural induction of hiPSC and human iPS cell expressing N-terminally FLAG-tagged TET1 protein.
Figure 15:
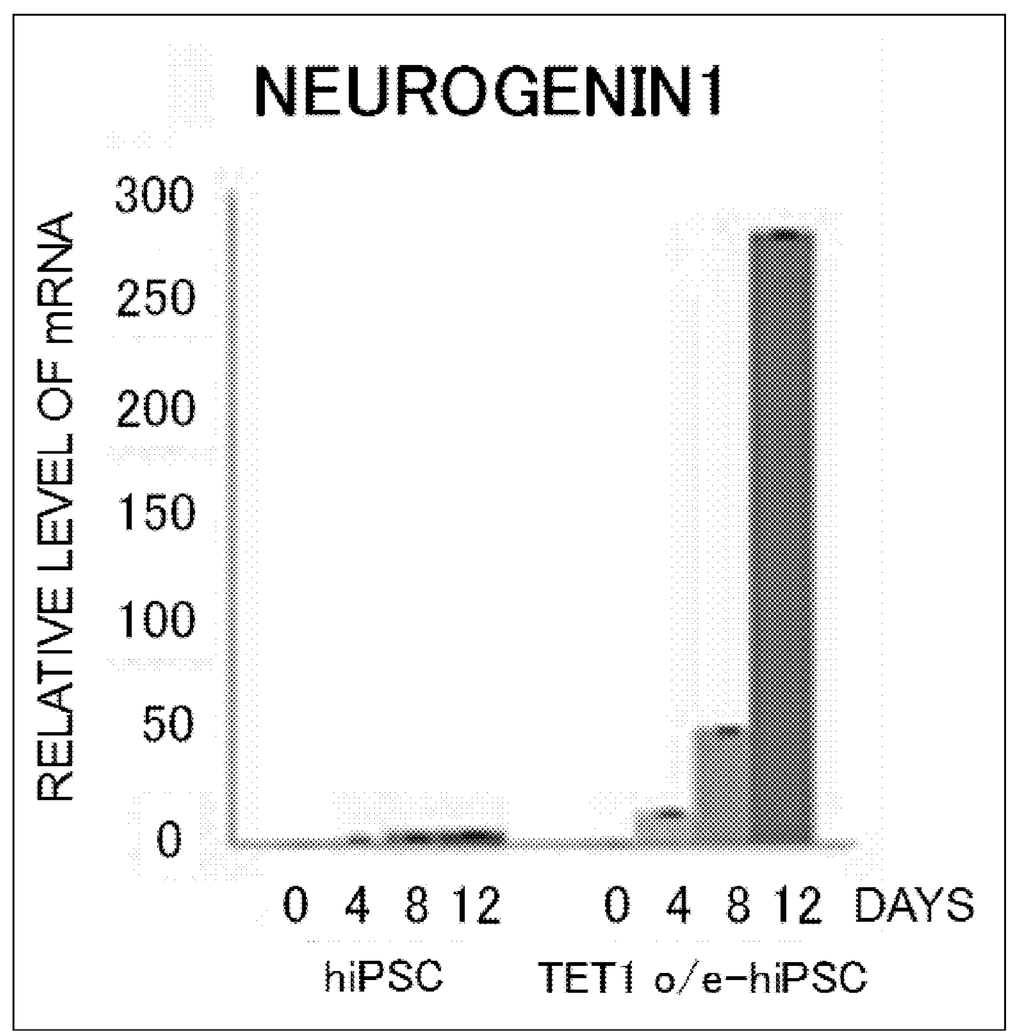
FIG. 15 The graph shows the time course of NEUROGENIN1 mRNA expression during the neural induction of hiPSC and human iPS cell expressing N-terminally FLAG-tagged TET1 protein.
Figure 16:
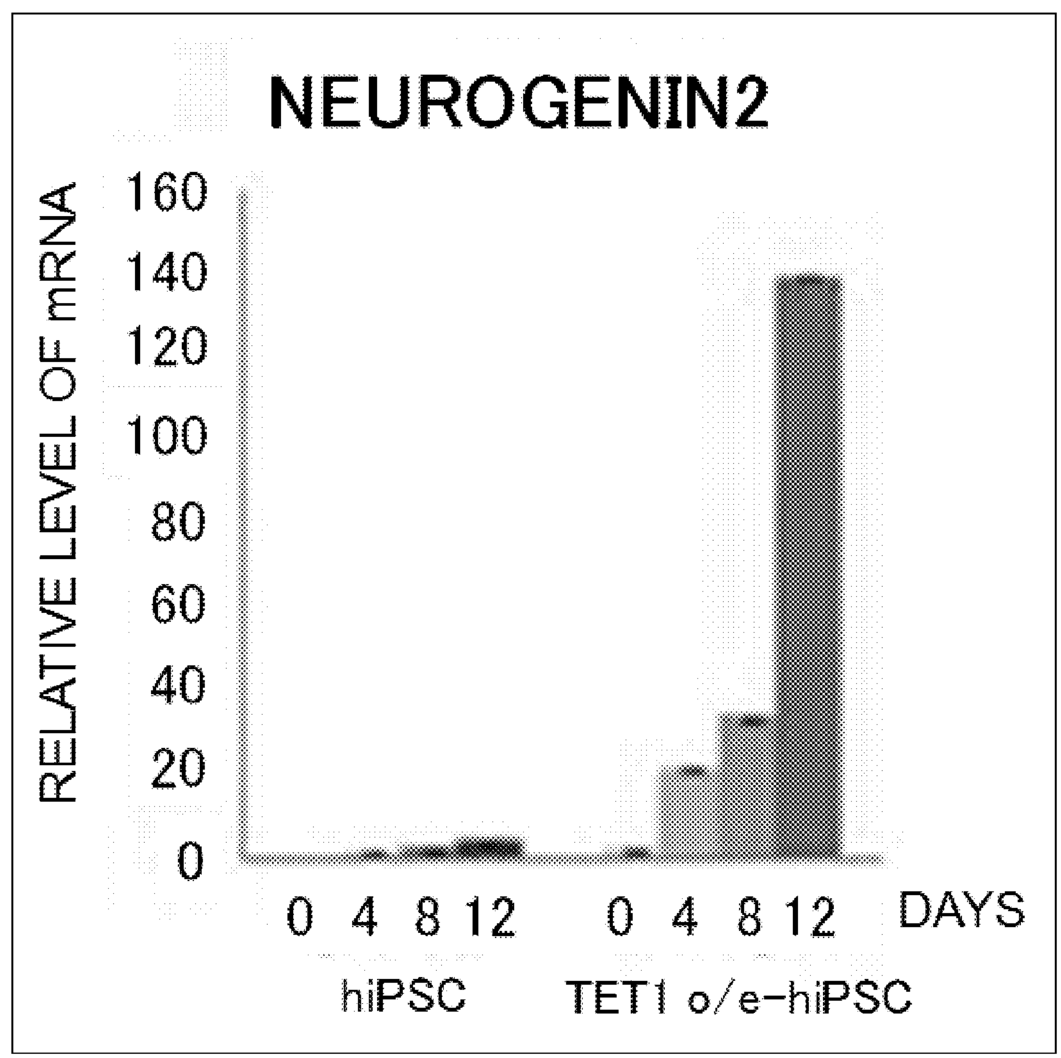
FIG. 16 The graph shows the time course of NEUROGENIN2 mRNA expression during the neural induction of hiPSC and human iPS cell expressing N-terminally FLAG-tagged TET1 protein.
Figure 17:
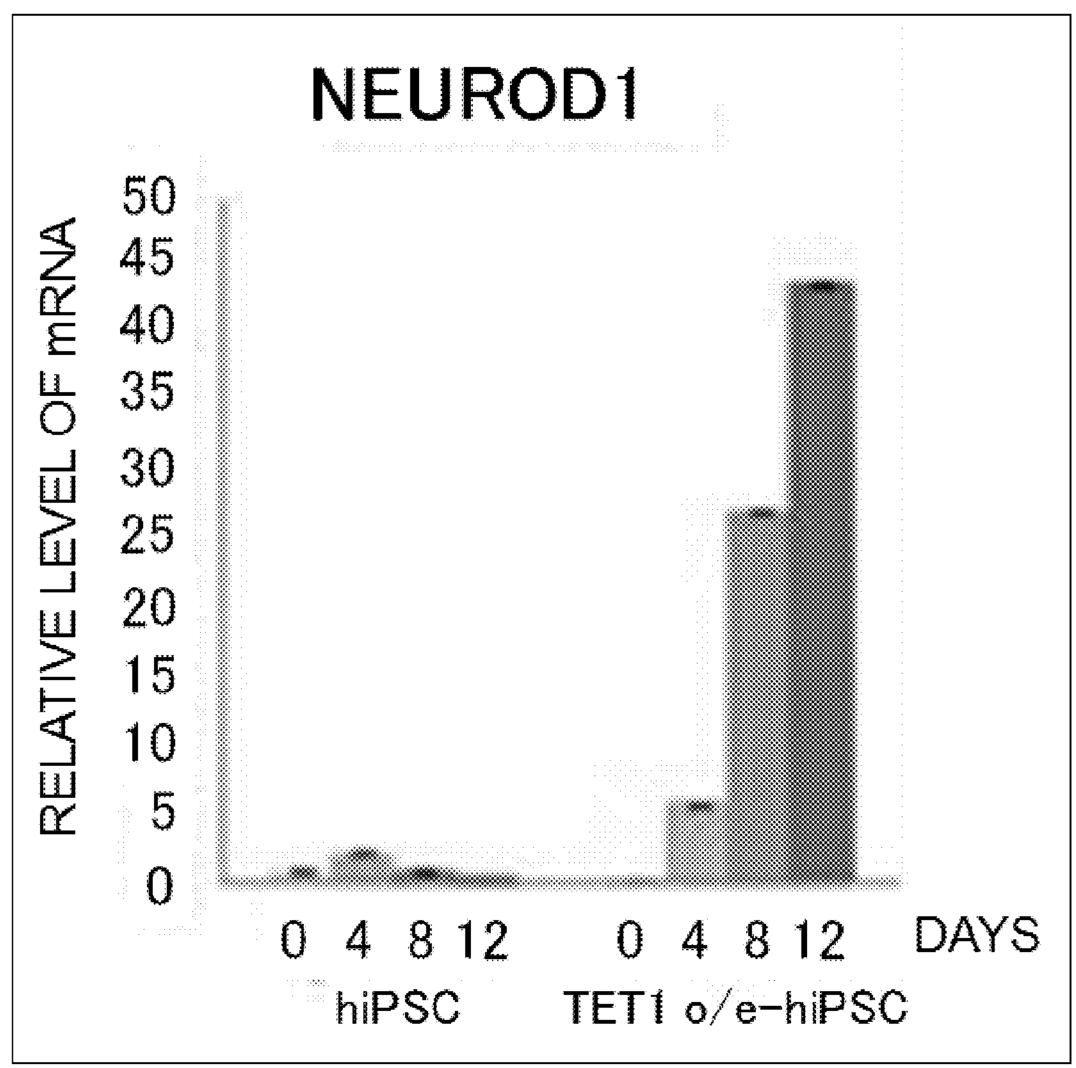
FIG. 17 The graph shows the time course of NEUROD1 mRNA expression during the neural induction of hiPSC and human iPS cell expressing N-terminally FLAG-tagged TET1 protein.
Figure 18:
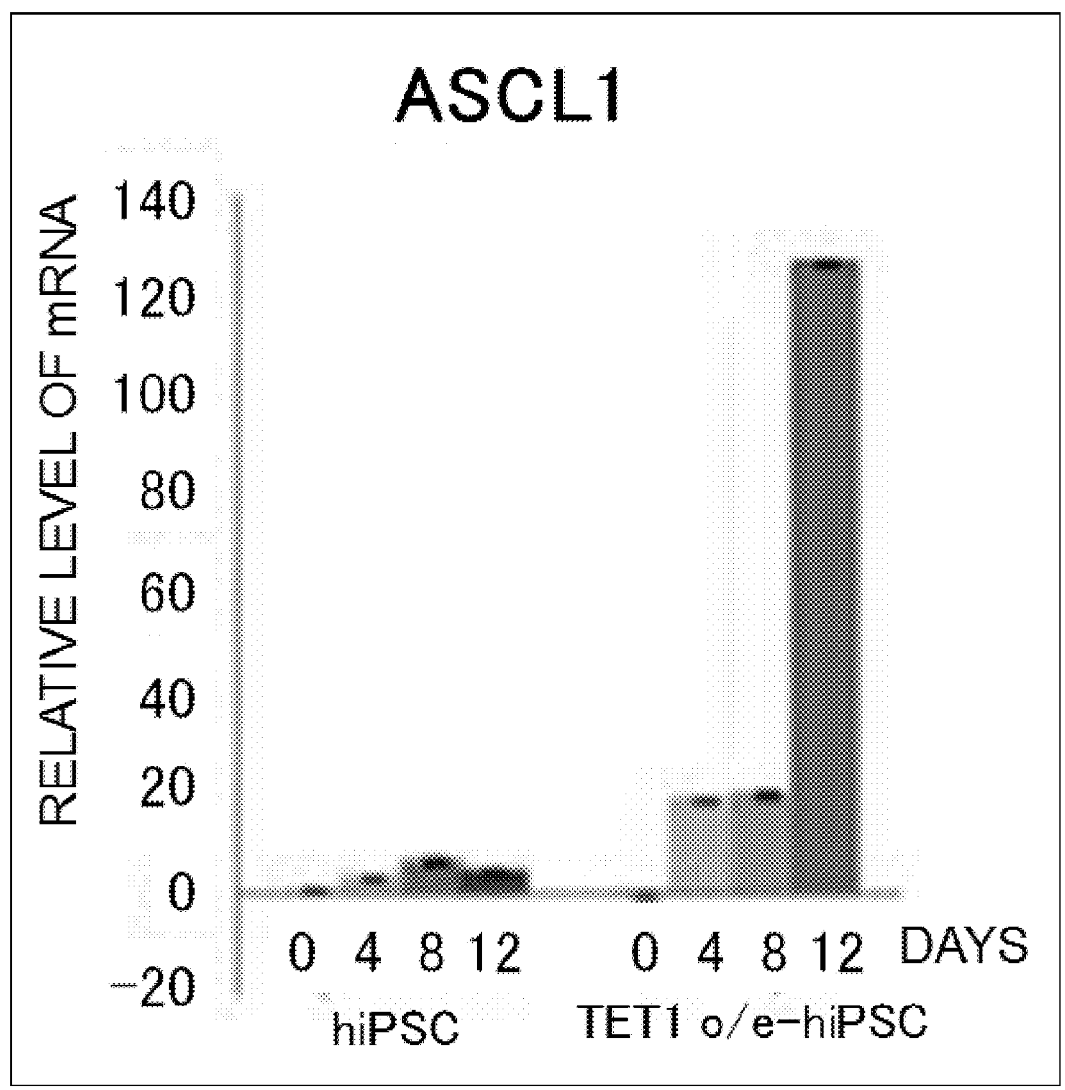
FIG. 18 The graph shows the time course of ASCL1 mRNA expression during the neural induction of hiPSC and human iPS cell expressing N-terminally FLAG-tagged TET1 protein.
Figure 19:
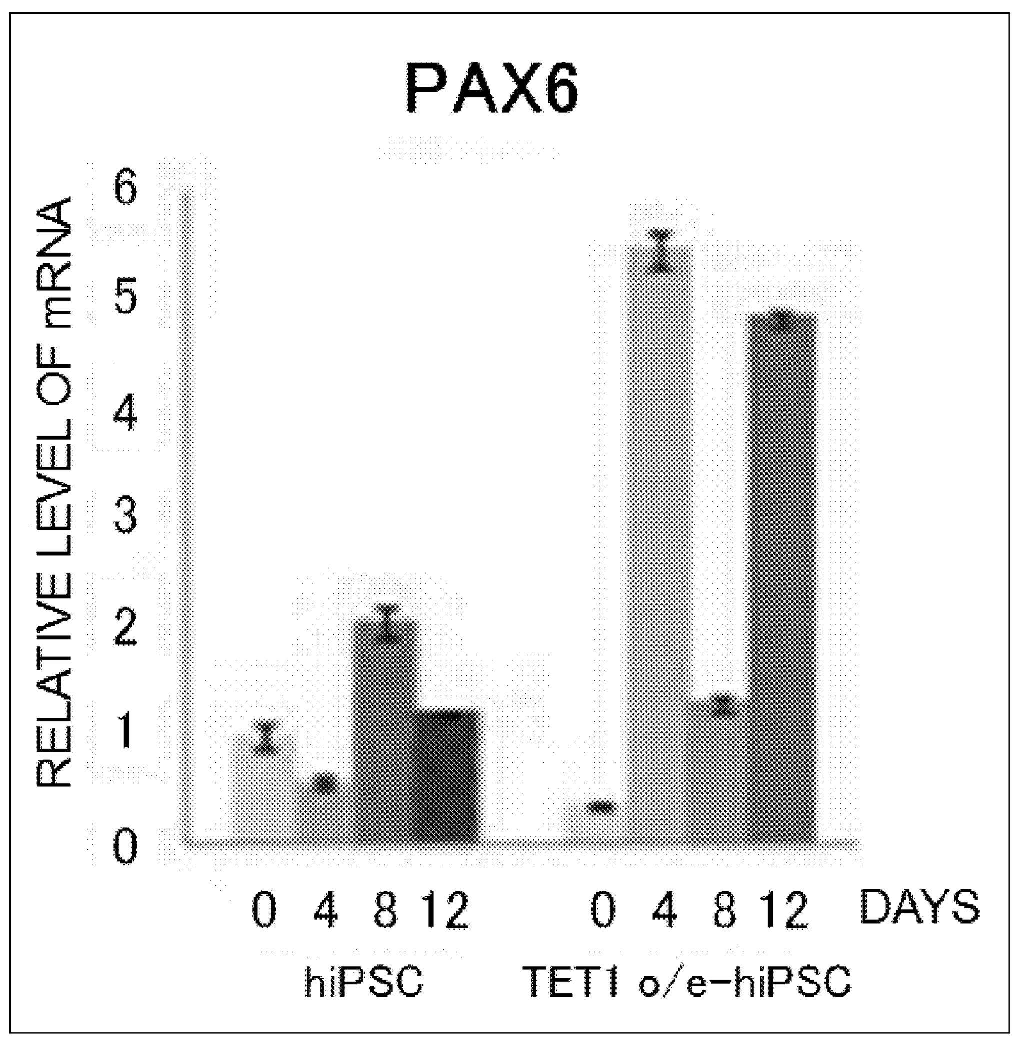
FIG. 19 The graph shows the time course of PAX6 mRNA expression during the neural induction of hiPSC and human iPS cell expressing N-terminally FLAG-tagged TET1 protein.
Figure 20:
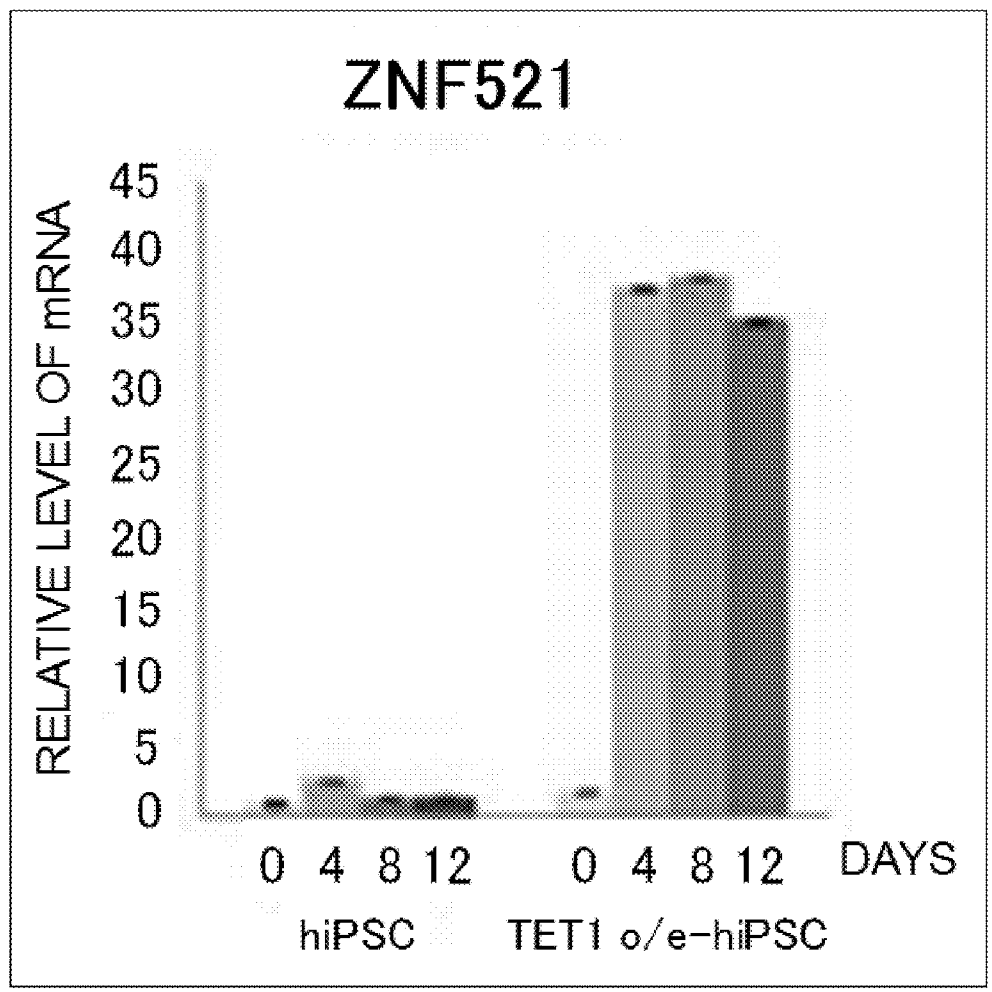
FIG. 20 The graph shows the time course of ZNF521 mRNA expression during the neural induction of hiPSC and human iPS cell expressing N-terminally FLAG-tagged TET1 protein.

As clearly shown in FIG. 8, the level of TET1 mRNA expression in TET1-hiPSC prior to differentiation (Day 0), when compared to the control hiPSC which only expresses the pCAG-IP vector alone, is more than four times and from this, one can deduce that a three-fold expression of the endogenous expression was attained from the transgene expression. Compared to this change, the expression levels of the factors which are believed to correlate to the self-renewality of PSCs at undifferentiated state such as OCT3/4, NANOG or SOX2 mRNA did not significantly differ between hiPSCs with or without TET1-overexpression (FIGS. 11-13; see data at Day 0).

Primed PSCs, which are supposed to be quasi-equivalent to epiblast-stage embryonic cells, are also supposed to have capacities to differentiation toward ectoderm or mesendoderm. To this end, interestingly, the expressivity of ectodermal differentiation markers (markers for neural differentiation: SOX1, NEUROGENIN1, NEUROGENIN2, NEUROD1, ASCL1, PAX6, ZNF521 and OTX2) did not differ between hiPSCs at their undifferentiated states regardless the presence or absence of TET1-overexpression (FIGS. 14-21; refer to Day 0 data).

Figure 22:
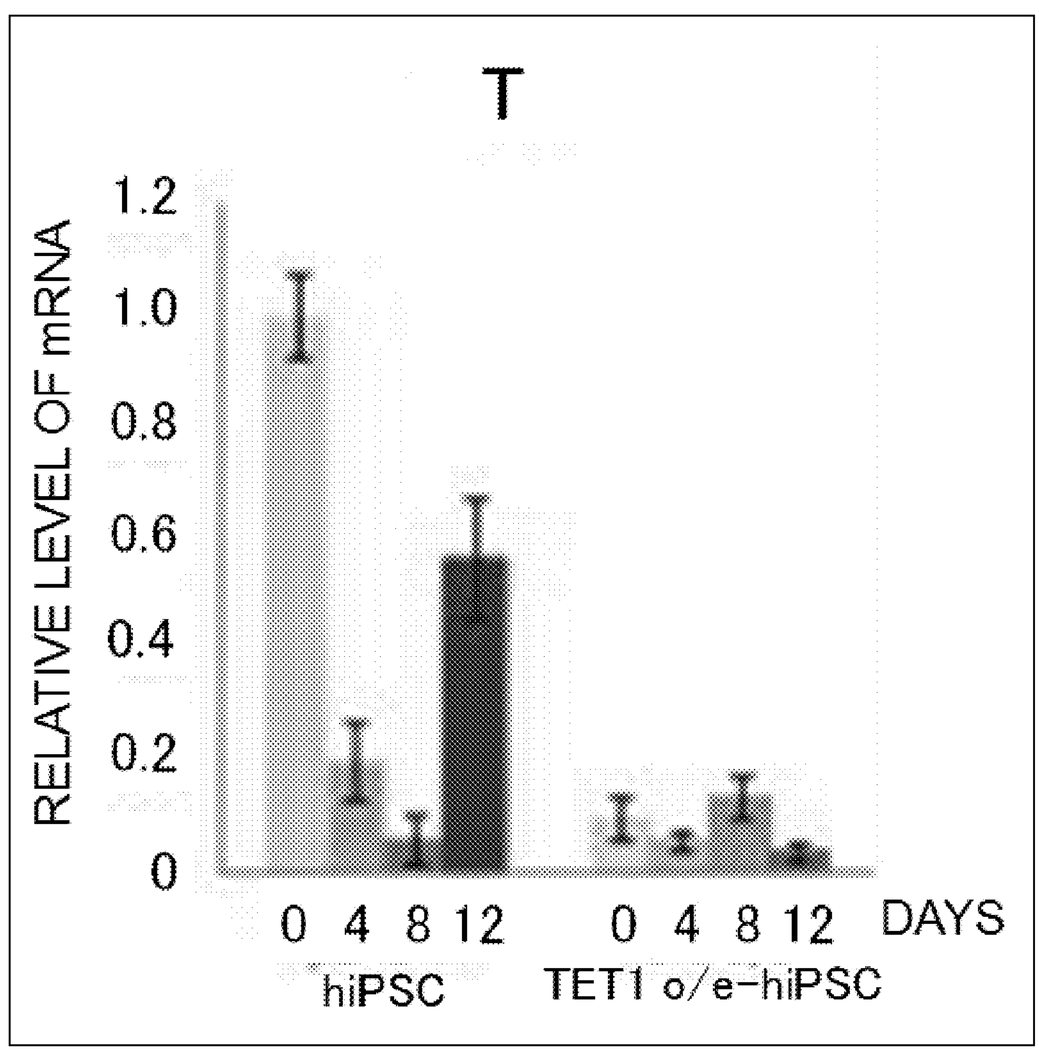
FIG. 22 The graph shows the time course of T mRNA expression during the neural induction of hiPSC and human iPS cell expressing N-terminally FLAG-tagged TET1 protein.
Figure 23:
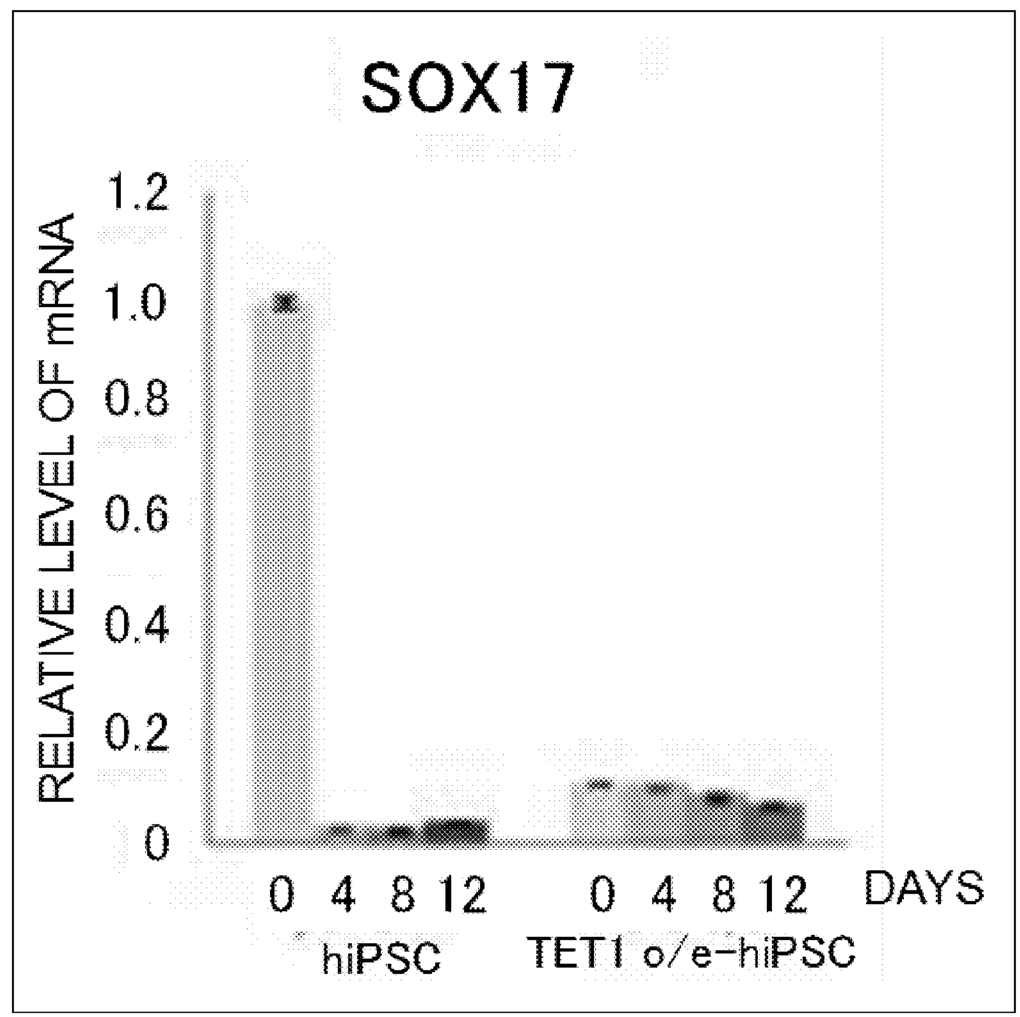
FIG. 23 The graph shows the time course of SOX17 mRNA expression during the neural induction of hiPSC and human iPS cell expressing N-terminally FLAG-tagged TET1 protein.

However, the expression levels of T and SOX17, markers for mesendoderm differentiation, differed significantly between hiPSCs with and without the TET1-overexpression. Whereas hiPSCs, where the mutant TET1 protein is not overexpressed, expressed these markers, TET1-hiPSCs which were maintained in an identical culture condition did hardly express these markers (FIGS. 22 and 23; see the data of Day 0).

It is generally believed that T or SOX17 marks that the cells are already differentiated and in principle, should not be expressed in stem cells which are supposed to be in an undifferentiated state. This is suggestive that in human iPS cells induced in a conventional method over-reacted toward Activin A, which mimics the mesendodermal inducer NODAL activity, and exited from their undifferentiated state to reach mesendodermal cell lineage characteristics. In other words, one can deduce from these facts that the conventional human PSCs bear propensity toward mesendodermal differentiation and in the strict sense of the word, are not "undifferentiated".

Working Example 6

<Validating Neural Inducibility of TET1-hiPSC: Part 1>

Evolutionarily conserved phenomena in the early development of vertebrates are that the cell differentiation is set to differentiate toward neural cells by default (default neurogenesis; Levine A J. et al., Dev. Biol., 2007, vol. 308, 247-256). If early developing cells are dissociated in medium which does not have any inductive signaling molecules, the cells are to differentiate toward neurons. Mouse ES cells were known to follow this default neurogenesis rule (Smukler S R. et al, J Cell Biol, 2006, vol. 172, 79-90). The present inventor has also previously developed a protocol to efficiently induce neural cells from mouse ES cells based on this default pathway idea (Bouhon I A. et al, Brain Res Bull, 2005, vol. 68, 62-75). To date, however, the default status of the human PSCs totally remained to be a mystery.

In order to test the differentiation capacity of TET1-hiPSC, similar to a condition which would allow a mouse ES cell to follow the default neurogenesis, the inventors analyzed their differentiation directions. To this end, as previously mentioned, TET1-hiPSC and hiPSC were maintained in parallel in KFA, and then cultured in a developmentally neutral CDM medium for 4 days, followed by a condition where Activin A/Nodal was inhibited for neurogenesis. The default differentiation was followed up to 12 days and cell samples were collected every 4 days to analyze the dynamics of transcription factors' mRNA expression. The results were shown in FIGS. 8 to 23.

During neural differentiation, OCT3/4 and NANOG expression ought to be swiftly down-regulated during the process (Zheng W. et al, Cell Stem Cell, 2012, vol. 10, 440-454). Relevant to this, as clearly shown in FIGS. 11 and 12, during the first four days of differentiation, TET1-overexpression seemed to strongly impact the expressivity of OCT3/4 and NANOG. Especially for NANOG, its expression dropped down below to one-hundredth within the first four days of differentiation in TET1-hiPSCs. In sharp contrast, the conventional human iPSCs (hiPSCs) failed to down-regulate these factor expressions but up-regulated when following the default differentiation. Although not shown in a Figure, in hiPSCs, the OCT3/4 and NANOG expressions went down gradually over a period of one month but to only one-tenth of the original expression values.

As shown in FIG. 13, SOX2 expression in differentiating TET1-hiPSC was gradually up-regulated after the beginning of differentiation induction. SOX2 represents a transcription factor whose expression is observed in the undifferentiated PSC as well as being an essential factor for the development of the nervous systems. Therefore, one can deduce that the consistent expression of SOX2 in TET1-hiPSC during its course of differentiation into the nervous systems might have been a driver for the neural differentiation. Compared to this, in hiPSC, SOX2 expression went down.

Moreover, as clearly shown in FIGS. 14 to 21, we could observe marked up-regulation of neural markers in TET1-hiPSCs (SOX1, NEUROGENIN1, NEUROGENIN2, NEUROD1, ASCL1, PAX6, ZNF521 and OTX2). In contrast, such marker expressivities were not observed for hiPSCs. Especially, the expression of SOX1 in differentiating TET1-hiPSCs at Day 12 of differentiation was 60 times than that of hiPSCs which do not express the TET1 protein. Judging from these, the overexpression of the mutant TET1 into human iPS cells renders these cells 60 times more amenable to neural differentiation.

Figure 21:
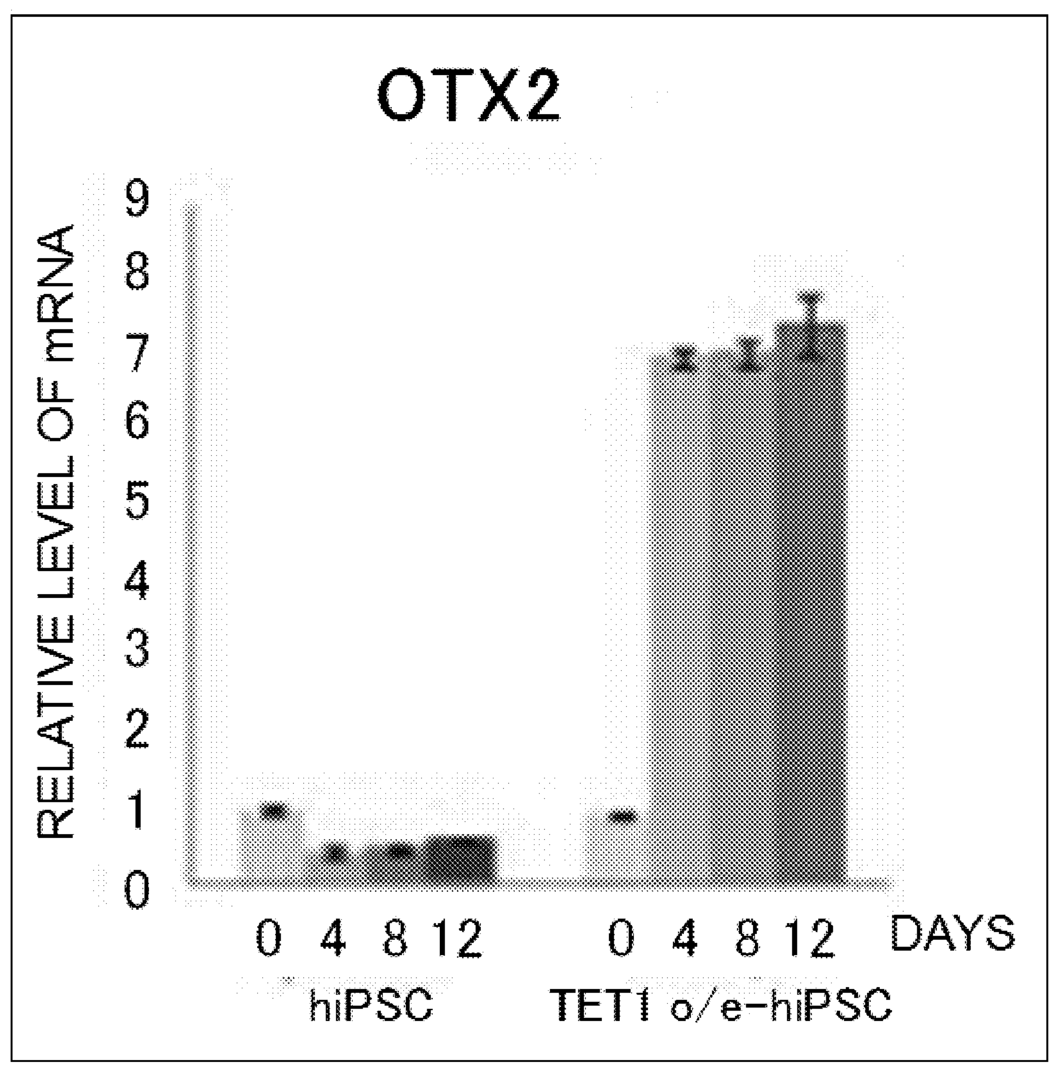
FIG. 21 The graph shows the time course of OTX2 mRNA expression during the neural induction of hiPSC and human iPS cell expressing N-terminally FLAG-tagged TET1 protein.

It is also established that the neurons induced through the default neurogenesis pathway bear the phenotypes of forebrain neurons. In close relation, as shown in FIG. 21, the mutant TET1 protein overexpression clearly allowed a marked induction of the forebrain marker OTX2. This result is therefore supportive of the fact that the mutant TET1 protein overexpression makes the human iPSCs conducive for default neurogenesis toward forebrain neurons.

As mentioned above, TET1 protein overexpression also allowed a swift down-regulation of NANOG. NANOG-down-regulation, not only for swift neural induction, is known to be prerequisites for proper differentiation into multiple cell lineages. Therefore, although here in the Working example 6 we focused on the effects of the mutant TET1 protein during neural (ectodermal) differentiation, the effects of the methods or the proteins in the present invention are not restricted to ectodermal differentiation but have larger impacts as will be shown in the Working examples 8. That is to say that the swift down-regulation of NANOG by the overexpressed TET1 protein is mechanically linked to a release of differentiation resistance and therefore operates in enhancing the pluripotency of the PSCs.

Working Example 7

<Validating Neural Inducibility of TET1-hiPSC: Part 2>

Figure 24:
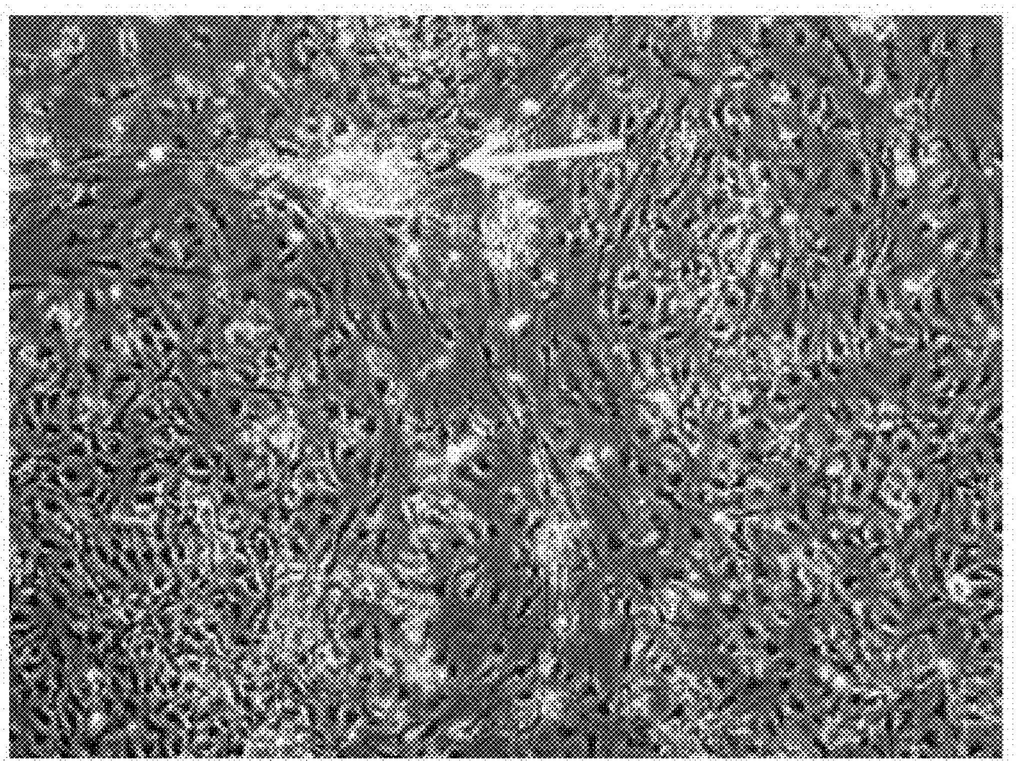
FIG. 24 A micrograph of human iPS cells plated onto laminin-coated culture dishes after 12 days of neural induction. The picture was taken 14 days after the plating of the induced cells. The arrow in the picture shows the position where an aggregate of neuron's cell somata were formed.

Here, the inventors have plated down the neural progenitor cells induced in the Working example 6 onto a laminin-coated culture dishes to observe their maturation to neurite-bearing mature neurons. The results are shown in FIGS. 24 and 25.

Figure 25:
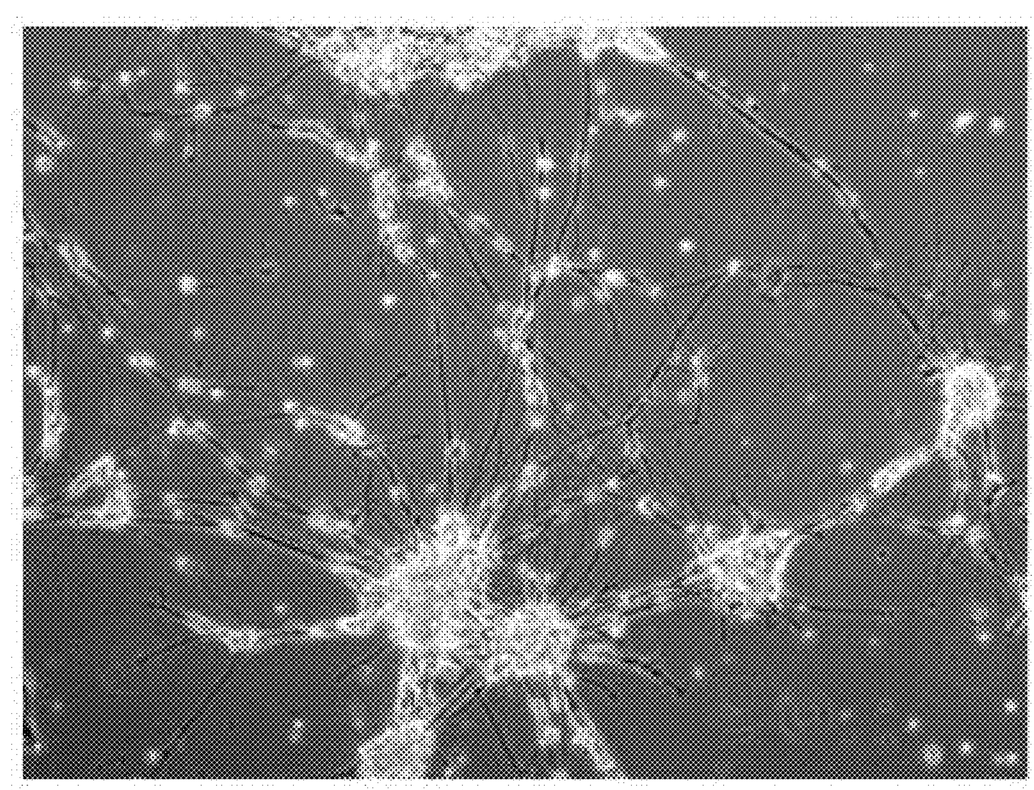
FIG. 25 A micrograph of human iPS cell expressing N-terminally FLAG-tagged TET1 protein plated onto laminin-coated culture dishes after 12 days of neural induction. The picture was taken 14 days after the plating of the induced cells.
Figure 26:
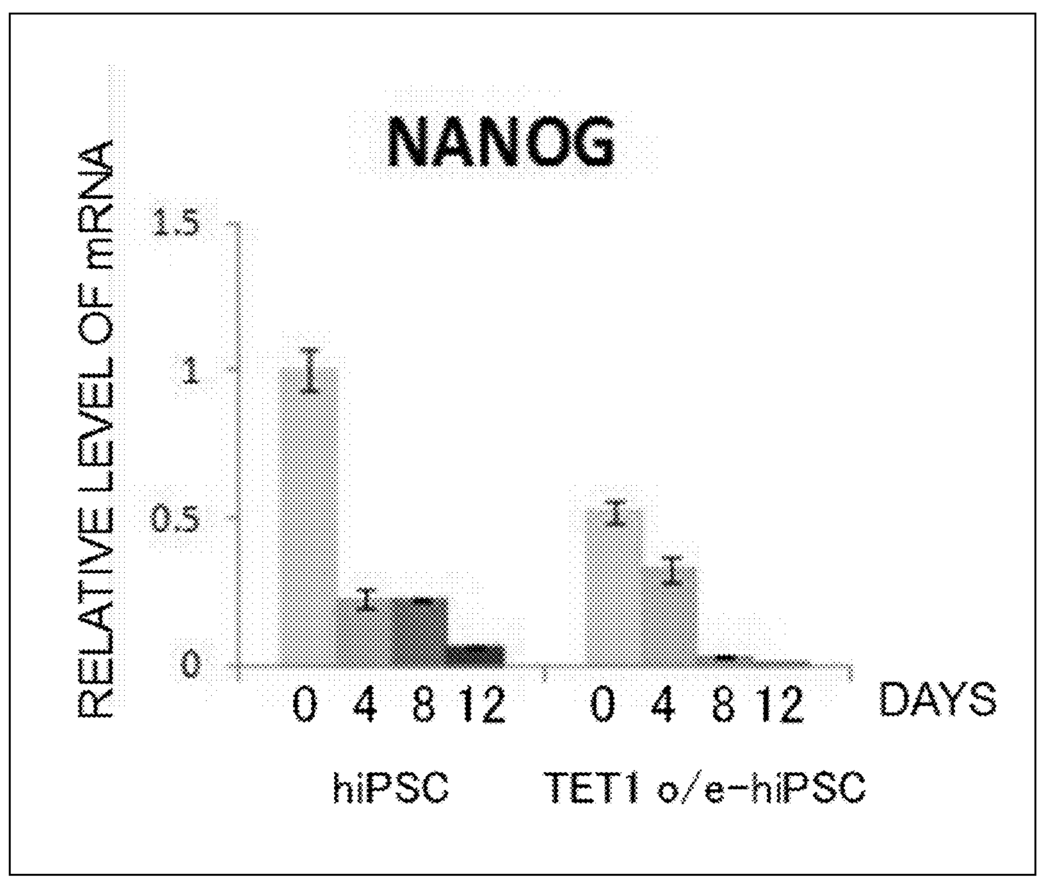
FIG. 26 The graph shows the time course of NANOG mRNA expression during the definitive endoderm induction of control human iPS cell (depicted as "hiPSC" in the figure) and human iPS cell expressing N-terminally FLAG-tagged TET1 protein ("TET1o/e-hiPSC"). The vertical axis represents a relative level obtained when the expression level in the human iPS cells before the differentiation induction is taken as 1. The horizontal axis of the graph represents the days after the commencement of definitive endoderm induction (also in FIGS. 27 to 29).
Figure 27:
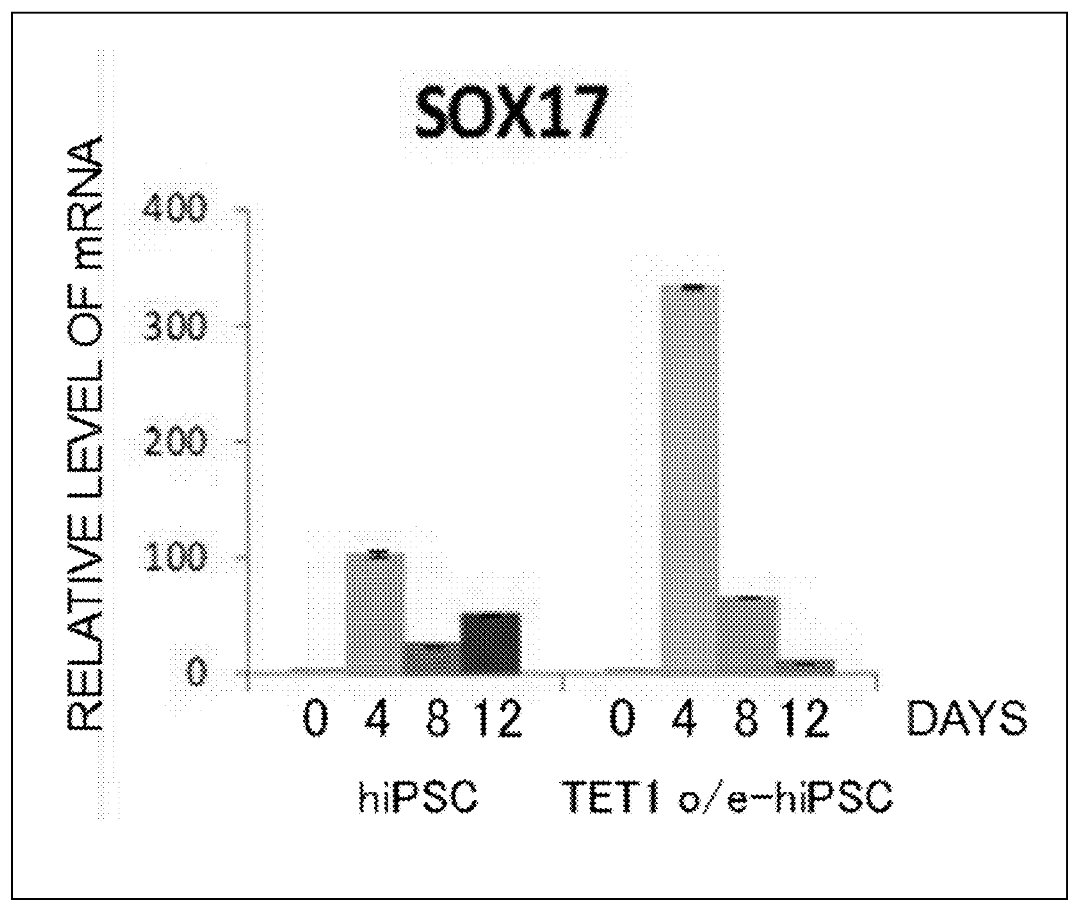
FIG. 27 The graph shows the time course of SOX17 mRNA expression during the definitive endoderm induction of hiPSC and human iPS cell expressing N-terminally FLAG-tagged TET1 protein.
Figure 28:
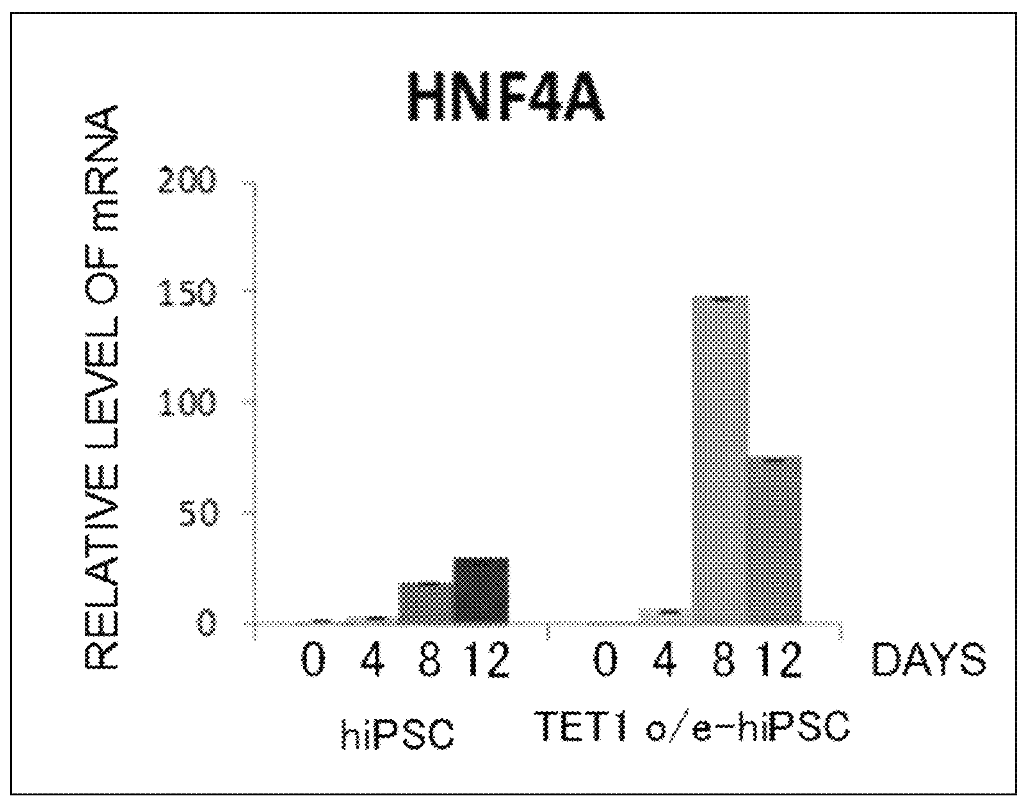
FIG. 28 The graph shows the time course of HNF4A mRNA expression during the definitive endoderm induction of hiPSC and human iPS cell expressing N-terminally FLAG-tagged TET1 protein.
Figure 29:
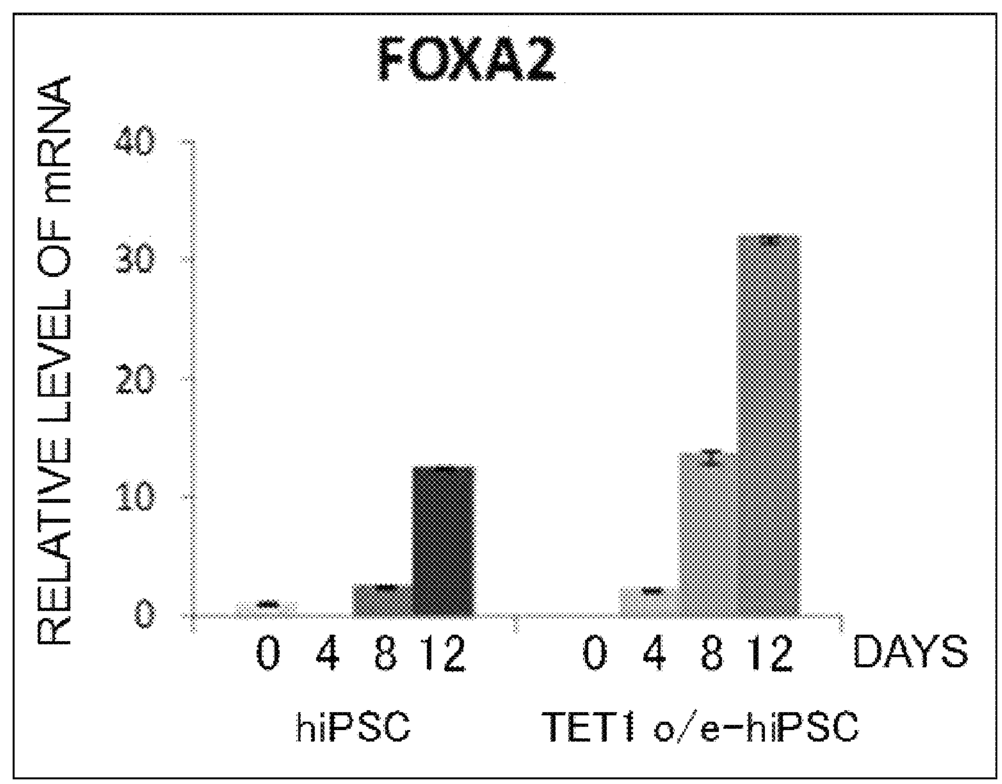
FIG. 29 The graph shows the time course of FOXA2 mRNA expression during the definitive endoderm induction of hiPSC and human iPS cell expressing N-terminally FLAG-tagged TET1 protein.

As clearly shown in FIG. 25, when TET1-hiPSCs were let to differentiate to neurons, a nearly 100% of the cells turned to neurons and no other cells were discernible in the culture. In contrast, from the conventional human iPS cells (hiPSCs), as shown in FIG. 24 by an arrow, although some neuron-aggregates were discernible, the culture became overwhelmed by growing non-neural cells leaving the proportion of neurons in a dish fairly low (FIG. 24).

Working Example 8

<Validating TET1-hiPSCs for Endodermal Differentiation>

The early mammalian development in its simplified form is a binary cell lineage choice between ectoderm which will eventually diversify into neural or dermal tissues or alternatively mesendoderm which will later diversify into mesoderm (blood, muscle, skeletal tissues) and endoderm (lung, digestive tracts). Therefore, the inventors sought to investigate the differentiation capacity to endoderm by TET1 in addition to its effect to the ectodermal differentiation.

<Endoderm Differentiation of Human iPS Cells>

Among endodermal organs, the pancreas which is related to diabetes mellitus and the liver which is the central organ for metabolism and detoxification have attracted major medical concerns and as a consequence, developments for protocols deriving these organs are under intensive investigation. The inventors have therefore modified a differentiation protocol originally devised for inducing the insulin-secreting pancreatic 13 cells (D'Amour K A, Nat Biotech, 2006, vol. 24, 1392-1401) to execute the differentiation of the definitive endoderm cells.

The modifications made to the original protocol are as follows. The basic medium RPMI used in the paper was replaced to CDM medium which the inventors have used for differentiating neurons; Wnt3a recombinant proteins were replaced with a small molecule compound CHIR99021 which also transduces through the same signaling pathway; and Cyclopamine (a hedgehog signaling antagonist) which was used to derive pancreatic lineages was omitted in the example here. The last modification is expected to orient human iPS cells toward a liver cell lineage instead.

Below, this differentiation method is explained for each stage.

Stage 1: Determination of the Definitive Endoderm (4 Days)

Human iPS cells (human iPS cell line overexpressing the mutant TET1 protein (TET1-hiPSC) and YMhiPSC058sbc6 subclone as described in the Working example 3) were routinely maintained for undifferentiated condition in KFA medium and passaged by trypsin-dissociation. After adequate treatment of trypsin, its activity was stopped using trypsin inhibitor. About 2,000 single cells obtained in this manner were individually seeded into separate non-attaching wells (Nunclon Sphera, Thermo) in CDM medium supplemented with Activin A (100 ng/ml), CHIR99021 (3 μM) and ROCK inhibitor (Y27632; 10 μM) and let them to form cell spheres. 48 hours later, the medium was changed to fresh CDM supplemented with Activin A (100 ng/ml). After another 48 hours, the cells are supposed to be determined to the definitive endoderm stage (stage marker: SOX17).

Stage 2: Primitive Gut Formation (4 Days)

Once using the differentiation procedure, cells which have fixed their cell lineage into endoderm are formed, and these cells are further induced toward the primitive anlage of the digestive organs called primitive gut. The cell spheres collected from the Stage 1 above, are now seeded into CDM supplemented with FGF10 (50 ng/ml). After 4 days of culture, the cells are supposed to differentiate into primitive gut cells (marker: HNF4A).

Stage 3: Foregut Formation (4 Days)

The descendants of the primitive gut form rostrally the thyroid and the lungs and more caudally the digestive organs. Among these, the common ancestors for all digestive organs are the foregut cells. The spheres collected from the Stage 2 will be passed into fresh CDM medium supplemented with FGF10 (50 ng/ml) and all-trans retinoic acid (2 μM) and left for additional 4 days. As a result, cells are supposed to acquire foregut characteristics (marker: FOXA2).

The conventional human iPS cells and TET1-hiPSCs were in parallel processed using the differentiation protocol mentioned above and RNA samples were collected every 4 days. The collected RNAs were used as templates for qPCR to analyze the markers of each differentiation stage described above. Moreover, NANOG expression was also monitored to assess the undifferentiated status of the cells. The obtained results are shown in FIGS. 26 to 29.

The conventionally induced human iPS cells can also be differentiated toward endoderm at least to some degree as shown in FIGS. 26 to 29. In contrast, from the TET1-hiPSCs, we could clearly observe a marked down-regulation of NANOG together with an eminent up-regulation of the endodermal markers (SOX17, HNF4A and FOXA2). Collectively from these marker expression analyses, one can deduce that TET1-iPSCs, in comparison to conventionally made iPSCs, have roughly 3-time enhanced differentiation capability toward the endoderm lineages. Therefore, in addition to the enhanced differentiation efficacy for ectoderm as described above, the differentiation efficacy toward endoderm of a PSC can also be enhanced by the introduction of the mutant TET1 protein.

Working Example 9

<Validation of the Mutant TET1 Proteins>

As described above, the inventors so far have exploited an N-terminal FLAG tagged TET1 protein (full length) as their mutant TET1 protein and observed its effects. Now, they are exploring here for another illustrative embodiment for their mutant TET1 protein which is equally capable of enhancing the differentiation efficacy of PSCs as will be shown below: this alternative embodiment is the first, N-terminal 670 amino acids of the wild-type TET1 where its second amino acid from the N-terminus was changed from serine to glycine and then fused a GFP tag (#94) as shown in FIG. 6.

First, four different human iPS cell lines were prepared as follows.

TET1o/e: YMhiPSC058sbc6 subclone (the mutant TET1 introduced hiPSCs in the Working example 3) which was introduced with the N-terminally FLAG-tagged full length TET1 protein

93: YMhiPSC058sbc subclone which was introduced with the N-terminal 670 amino acids of the wild-type TET1 which is fused to a Tag-GFP protein as shown in FIG. 6

94: YMhiPSC058sbc subclone which was introduced with the N-terminal 670 amino acids of the wild-type TET1 where its second amino acid from the N-terminus was changed from serine to glycine as shown in FIG. 6 pCAG-IP: YMhiPSC058sbc subclone which was introduced with a mock vector (pCAG-IP) to acquire the antibiotics resistance (serving as control cell line)

As shown in the Working example 3, #93-, #94-, and pCAG-IP were prepared by constructing pCAG-IP vector encoding each mutant TET1 expressing protein or pCAG-IP (mock vector) and introducing them into YMhiPSC058sbc6 subclone cells using Nucleofector, and thereby, drug-resistant clones were collected.

These iPS cell lines were processed according to the aforementioned neural differentiation protocol and marker expression was evaluated for 8 days of differentiation. The results are shown in FIGS. 30 to 32.

Figure 30:
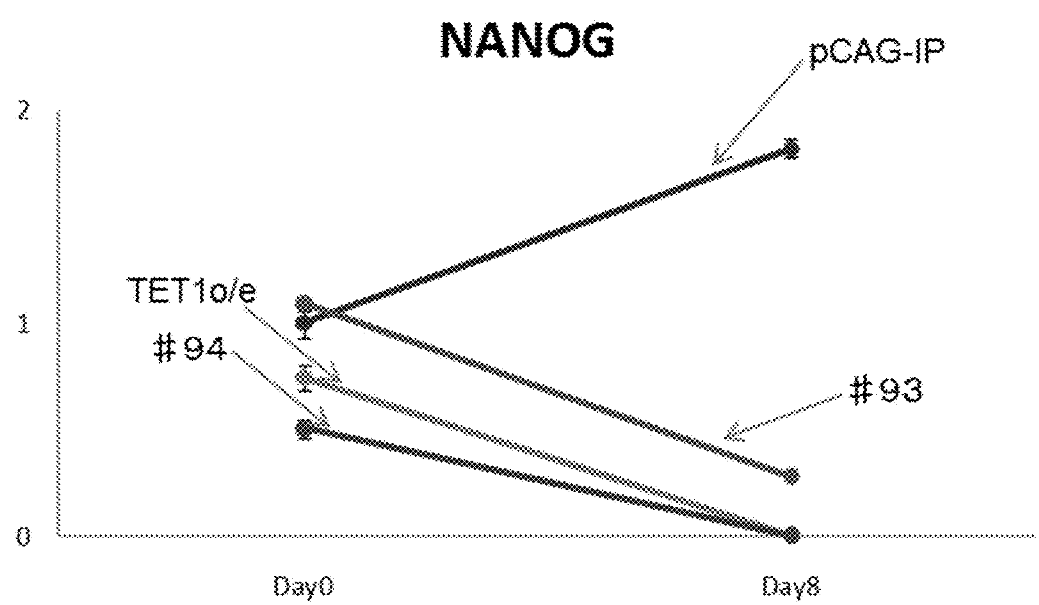
FIG. 30 The graph shows the time course of NANOG mRNA expression during the neural induction of human iPS cell bearing various transgenes: a mock vector expressing human iPS cell (pCAG-IP), human iPS cell expressing a fusion protein of the N-terminal portion of the human TET1 protein (the protein consisting of 670 amino acids) fused to GFP (#93), human iPS cell expressing a fusion protein of the N-terminal portion of the human TET1 protein (the protein consisting of 670 amino acids) with the second amino acid serine converted to glycine, fused to GFP (#94), and human iPS cell expressing N-terminally FLAG-tagged TET1 protein (full-length) ("TET1o/e-hiPSC"). The vertical axis represents a relative level obtained when the expression level in pCAG-IP before the differentiation induction is taken as 1. The horizontal axis of the graph represents the days after the commencement of neural induction (also in FIGS. 31 and 32).
Figure 31:
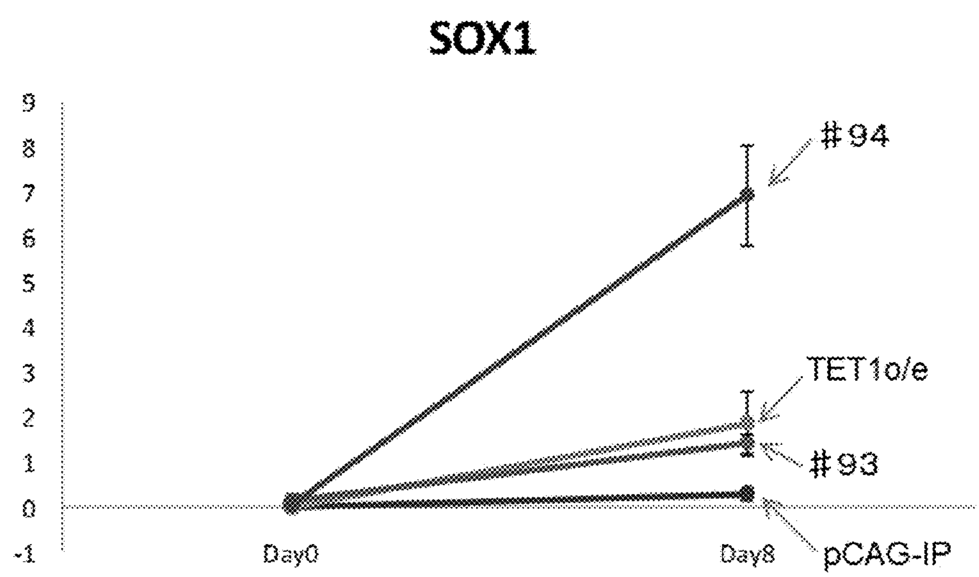
FIG. 31 The graph shows the time course of SOX1 mRNA expression during the neural induction of human iPS cell bearing various transgenes: a mock vector expressing human iPS cell, human iPS cell a fusion protein of the N-terminal portion of the human TET1 protein (the protein consisting of 670 amino acids) fused to GFP, human iPS cell expressing a fusion protein of the N-terminal portion of the human TET1 protein (the protein consisting of 670 amino acids) with the second amino acid serine converted to glycine, fused to GFP, and human iPS cell expressing N-terminally FLAG-tagged TET1 protein (full-length). In the figure, the vertical axis represents certain relative values because the value of the mock vector expressing human iPS cells (pCAGIP) before the differentiation was below the detection level.
Figure 32:
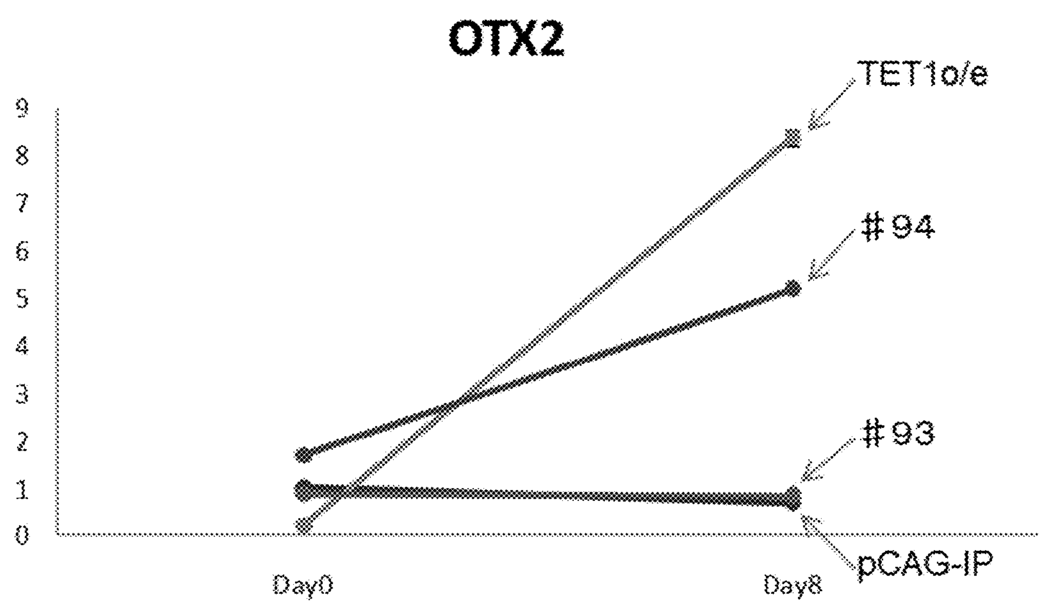
FIG. 32 The graph shows the time course of OTX2 mRNA expression during the neural induction of human iPS cell bearing various transgenes: a mock vector expressing human iPS cell (pCAG-IP), human iPS cell a fusion protein of the N-terminal portion of the human TET1 protein (the protein consisting of 670 amino acids) fused to GFP, human iPS cell expressing a fusion protein of the N-terminal portion of the human TET1 protein (the protein consisting of 670 amino acids) with the second amino acid serine converted to glycine, fused to GFP, and human iPS cell expressing N-terminally FLAG-tagged TET1 protein (full-length).

As clearly shown in FIGS. 30 to 32, not only the human iPS cell line which has received an N-terminally FLAG-tagged full length TET1 protein (TET10/e) but also the human iPS cell line, which is the alternative embodiment of this invention and was introduced with the N-terminal 670 amino acids of the wild-type TET1 where its second amino acid from the N-terminus was changed from serine to glycine fused to a Tag-GFP protein (#94), equally displayed enhanced differentiation efficacies toward neurons. Therefore, for the enhancement in the differentiation efficacy of PSCs, DNA demethylating activity exerted by the C-terminally situated dioxygenase domain of TET1 is redundant and therefore, we can deduce that DNA-binding ability of the DNA-binding domain which is situated at the N-terminal portion of TET1 is sufficient.

Working Example 10

<Validating the Effect of the Mutant TET1 Protein in the Enhancement of the Production Efficacy of iPS Cells>

The rates of reprogramming toward iPS cells, especially human ones, are fairly low. Good quality fully-reprogrammed iPS cell, i.e., those forming sharply delimited colonies under microscope observation, lines are practically tough to obtain. Also, it is empirically known that iPSC colonies with said good morphology highly expressed transcription factors (such as OCT3/4 and SOX2) related to pluripotency, and are known to self-renew while maintaining its characteristics.

Therefore, the inventors next investigated whether introducing the mutant TET1 protein of the present invention together with the so-called reprogramming factors to somatic cells for iPS cells induction would enhance the production efficacy of iPS cells using the experiment as follows.

iPSC induction was performed as described above by introducing 6 factors (Oct3/4, Sox2, Klf4, L-MYC, LIN28 and shp53) but using the episomal vector system established by Okita et al. N-terminally FLAG-tagged full length TET1 was introduced into the same vector as used in the system and iPS cells were induced based on the presence or absence thereof.

Figure 33:
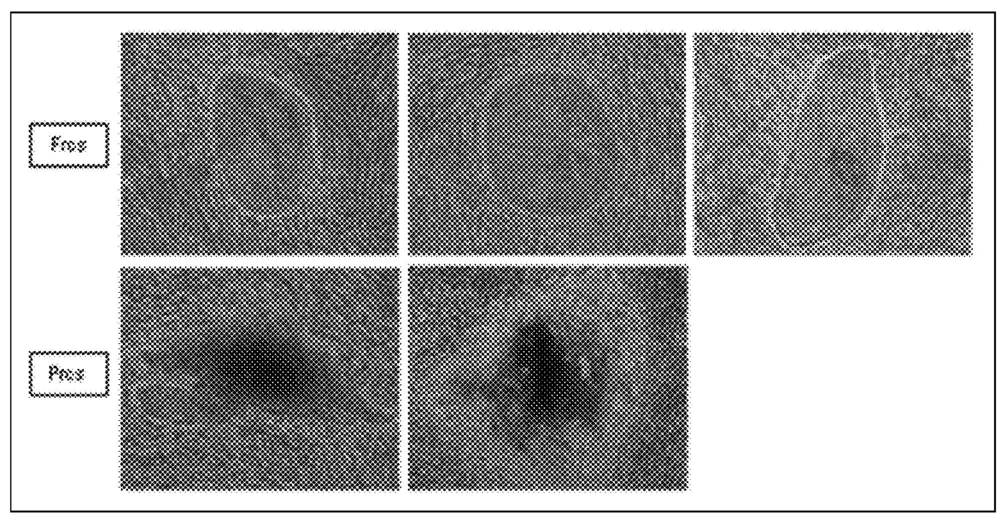
FIG. 33 Phase contrast micrographs of colonies composed of iPS cells of high quality (Frcs) and colonies composed of iPS cells of low quality (Prcs).

The resulting iPS cell colonies were observed and their numbers were counted. The result is shown in Table 2. In Table 2, "6 factors" shows the result of iPS cell induction by introducing the above-described 6 factors and "6 factors +Flag-TET1" shows the result of iPS cell induction by introducing the above-described 6 factors plus the mutant TET1 protein of this invention. "Frcs" denotes the number of colonies composed of iPS cells with high quality and "Prcs" denotes the number of colonies composed of iPS cells with low quality. In FIG. 33, we have displayed examples of "Frcs" and "Prcs".

TABLE 2

| vector | Frcs | Prcs |
|---|---|---|
| 6 factors | 10 | 12 |
| 6 factors + Flag-TET1 | 40 | 7 |

As shown in Table 2, compared to the conventional iPS cell induction without TET1, the number of iPS cell colonies significantly increased (from 22 colonies to 47 colonies) by the method of inducing iPS cells in which the TET1 protein of this invention is introduced. Moreover, although the conventional induction method gave equal numbers for Frcs and Prcs, using the iPS induction method of this invention, the inventors could also raise the proportion of Frcs (the proportion of Frcs increased from 10/22 to 40/47).

Collectively, by the method for producing PSCs by introducing the TET1 protein of this invention, it has been shown that it is now possible not only to enhance the differentiation efficacy of the obtained PSCs but also to enhance the production efficacy of such PSCs.

Working Example 11

<Evaluation of the Human iPSCs Overexpressing Mutant-TET1 at their Undifferentiated State 2>

The inventors further analyzed their mutant-TET1 overexpressing human iPSC (TET1-hiPSC) at its undifferentiated state in terms of its proliferability and by surveying its gene expression profile.

Figure 34:
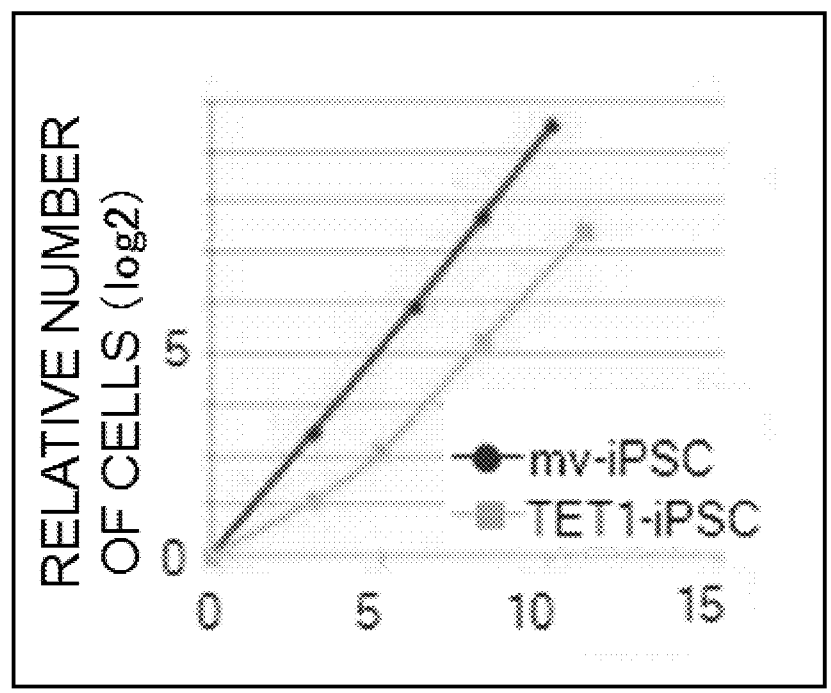
FIG. 34 The graph shows the cell proliferation curves for mock-vector introduced human iPS cells ("mv-iPSC"; same in FIG. 35 and FIG. 36) and human iPS cells with overexpression of N-terminal FLAG-tagged TET1 protein ("TET1-iPSC"; same in FIG. 35 and FIG. 36). The horizontal axis denotes days in culture.
Figure 35:
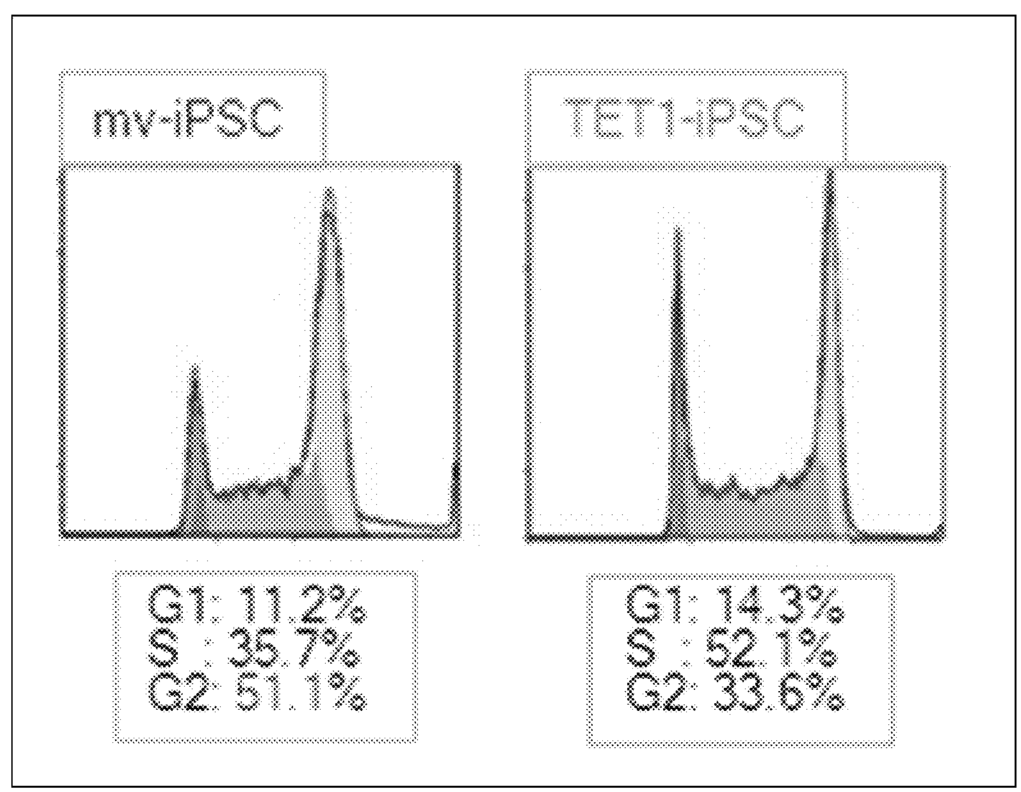
FIG. 35 Histograms showing cell cycle profiles of mv-iPSC and TET1-iPSC analyzed using FACS. In the figure, cell number ratios for G1, S and G2 phase are shown in percentiles.

Although not displayed as a figure, TET1-hiPSCs grew for at least 20 passages after its establishment in a stable fashion. Also, when compared with mock-vector-expressing hiPSCs (mv-iPSC), the cells proliferated more slowly (FIG. 34). Moreover, when their cell cycle were analyzed, TET1-iPSCs spent less time in G2 phase but tend to be more in S phase when compared to my-iPSCs (FIG. 35). As shown, TET1-iPSCs were more likely in S phase and less likely in G1/G2/M, a hallmark of a stem cell's cell cycle profile.

Figure 36:
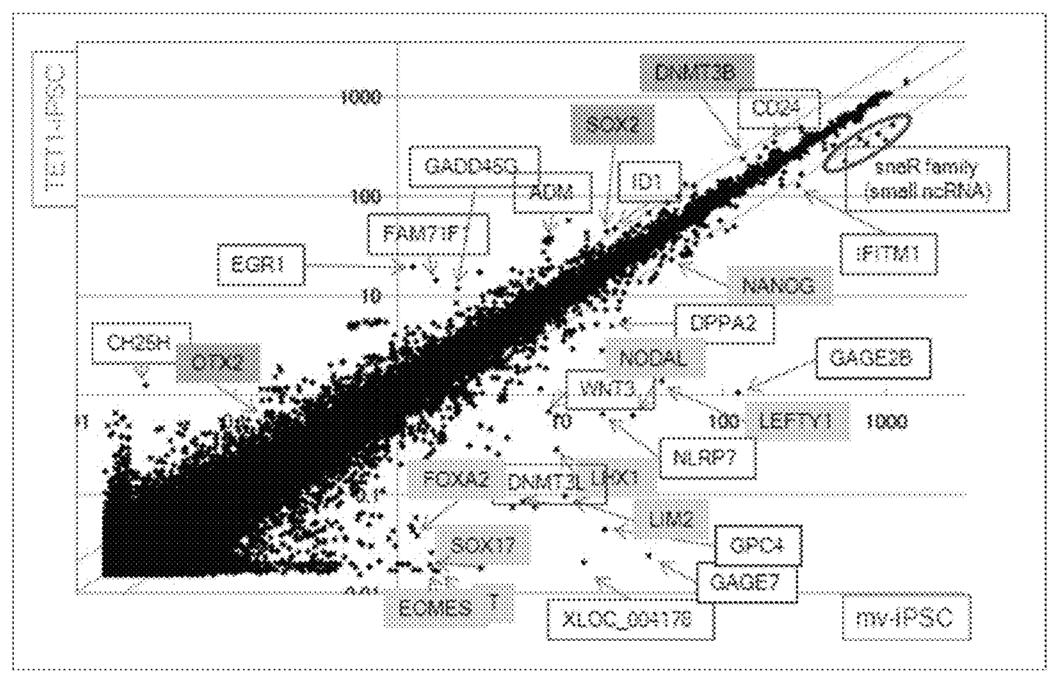
FIG. 36 Gene expression scattered plots of DNA microarray analysis showing genes whose expression differs between mv-iPSC and TET1-iPSC. DNA microarray analysis was performed on SurePrint G3 Human GE 8×60K v2 one-color platform (Agilent) and data analysis was done using 75-percentile shift method.

Moreover, when the transcriptome of TET1-iPSCs were analyzed globally using DNA microarray, the cells exhibited an expression profile which better fits a primed rather than a naïve stem cell (FIG. 36). For example, albeit the fact that no naïve-ness-related factors were over-represented, DNMT3B and OTX2, both a determinant of primed-ness were over-expressed in TET1-iPSCs. Also, except for increase in the expression of SOX2 and slight decrease in the expression of NANOG, factors which are related to pluripotency did not significantly change between the two cell populations. Although not shown as a figure, culturing the TET1-hiPSCs in LIF did not turn them into a naïve status.

And also, globally viewed, TET1-hiPSC gene expression profile indicated that the cell is more undifferentiated compared to its control mv-iPSC. That is, the overexpression of TET1 was able to significantly decrease the expression of NODAL and its direct target genes (LEFTY1 and LEFTY2) as well as some mesendodermal markers (T, SOX17, MIXL1, EOMES, LHX1, LIM2 and FOXA2). Moreover, the NODAL down-regulation by TET1-introduction was by a factor of 45, contrary to the mesendoderm-differentiation propensity of the conventional hiPSCs without TET1 as show above. Also not shown are quantitative RT-PCR data which confirmed the up-regulation of DNMT3B and the significant down-regulation of mesendodermal factors in TET1-hiPSCs. And, the fact that cancer-related markers (GPC4, GAGE2B and GAGE7) are over-represented in the conventional hiPSCs when compared to TET1-hiPSCs is indicative that the conventional hiPSCs without TET1bear endogenous carcinogenic property (FIG. 36). Although the definitive neuroectodermal marker SOX1 was not expressed in both the TET1-hiPSCs and mv-iPSC, TET1-hiPSCs showed enhanced expression of DNMT3B, SOX2 and OTX2 which may explain their higher differentiation capability toward a neural fate.

Working Example 12

<Evaluation of the Transition of the Tet1-Knockdown Mouse ES Cell to the Primed Stage>

Figure 37:
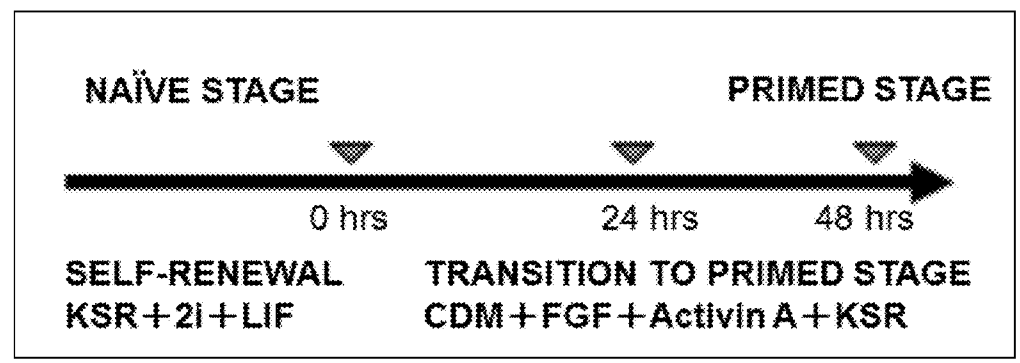
FIG. 37 A schematic drawing showing the transition from mouse ES cell's naïve stage to primed stage. From a naïve culture of mouse ES cells, leukemia inhibitory factor (LIF) and other agents preventing the transition to the naïve stage were removed and then said cells were transferred to FGF2 and Activin A (TGFβ/Nodal agonist) containing media which allow them to transition to the primed stage's status.
Figure 38:
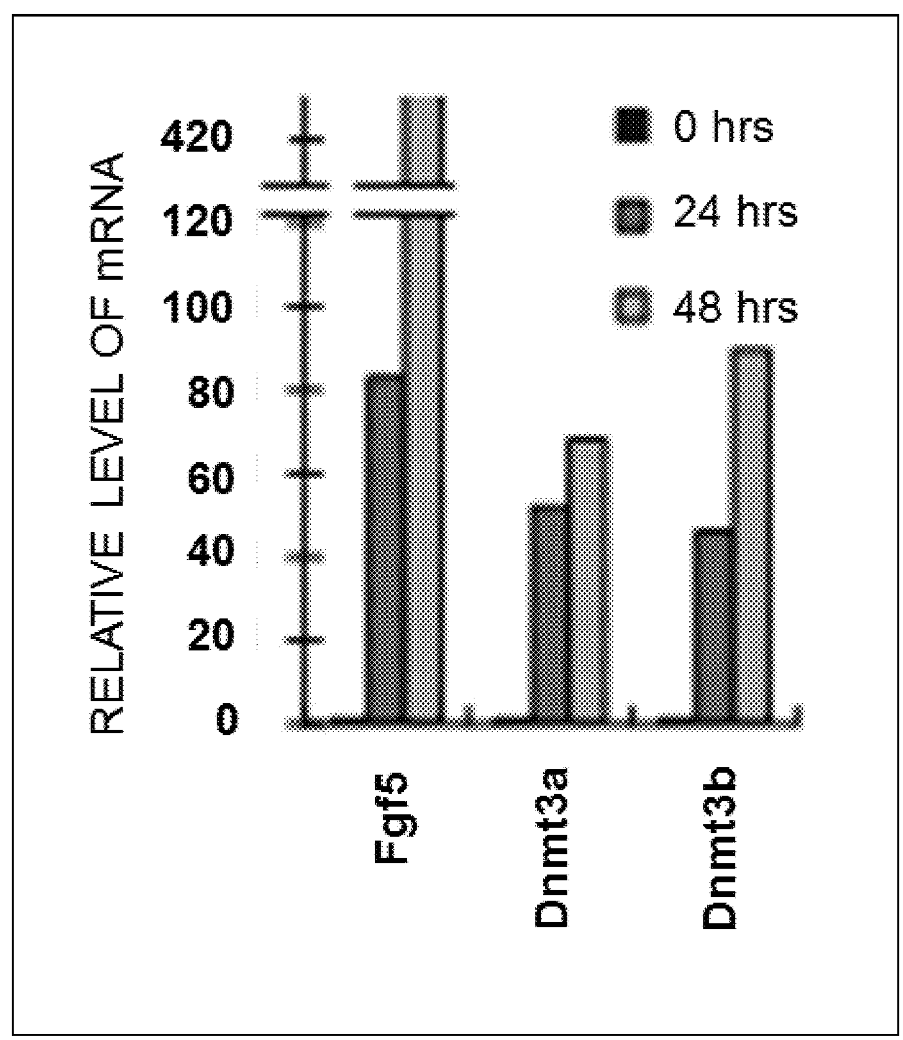
FIG. 38 The graph shows qPCR results which show up-regulation of epiblast markers during the naïve to primed transition. Each bar from left to right represents data of 0 hour, 24 hours and 48 hours after transition induction, respectively (The same applies to FIGS. 40 to 54).
Figure 40:
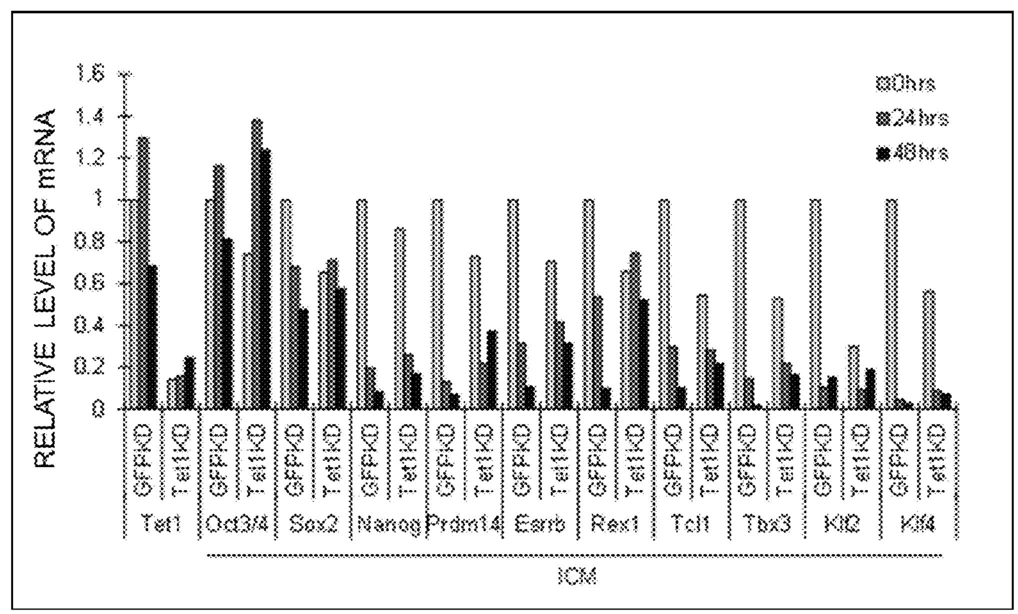
FIG. 40 The graph shows the qPCR results for the naïve to primed transition of mouse ES cells showing the effect of Tet1 knockdown. Tet1KD denotes for mouse ES cells in which Tet1 was knockdown and GFPKD is for mouse ES cells introduced with GFP-targeting shRNA which are used as control ES cells. ICM stands for the results of analysis for transcription levels of ICM/naïve stage markers.

As described above, by introducing TET1 proteins, it was possible to improve the differentiation potential of human iPS cells. So, the inventors further analyzed in details this aspect of Tet1 function using an in vitro mouse model of naïve-to-primed transition. In other words, according the description of "K. Hayashi, H. Ohta, K. Kurimoto, S. Aramaki, M. Saitou, Cell 146, 519 (Aug. 19, 2011)" and "G. Guo et al., Development 136, 1063 (April, 2009)", the inventors switched the culture conditions of the naïve mouse ES cells and let the cells proceed to an epiblast-like stage in 48 hours (called EpiLCs) (FIG. 37). In fact, the EpiLCs obtained this way showed increased expression of the primitive ectoderm cell markers Dnmt3b and FgfS, Dnmt3a (FIG. 38) and diminished expression of a battery of naive factors (FIG. 40).

Figure 39:
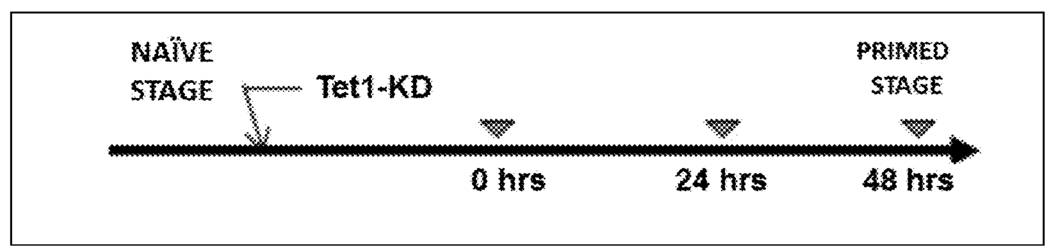
FIG. 39 Schematic drawing of the stages of the transition to epiblast-like stem cells (EpiLC) from Tet1-knockdown (Tet1-KD) mouse ES cells. Tet1-KD mouse ES cells were established by introducing shRNA against Tet1 and by selecting for puromycin resistance (Ref.: K. Williams et al., Nature 473, 343 (May 19, 2011)).

Then, in order to explore the role of Tet1 in establishing pluripotency, short hairpin RNA (shRNA) that targets all the Tet1 transcripts were used to decrease Tet1 expression in the in vitro model system (FIG. 39, please refer to K. Williams et al., Nature 473, 343 (May 19, 2011)).

Upon the knockdown (KD) of Tet1 in mouse ES cells, the expression levels of pluripotency-related marker such as Oct3/4 (Pou5fl), Sox2 and Nanog did not change (data not shown). And for the cell cycle, Tet1-KD ES cells exhibited typical stem-like cell cycle profile, indicating that as previously shown, Tet1 is not important in the self-renewability of the mouse ES cells (K. Williams et al., Nature 473, 343 (May 19, 2011), K. P. Koh et al., Cell Stem Cell 8,200 (Feb. 4, 2011), G. Ficz et al., Nature 473, 398 (May 19, 2011), M. M. Dawlaty et al., Cell Stem Cell 9, 166 M. M. Dawlaty et al., Dev Cell 24, 310 and (Aug. 5, 2011) (Feb. 11, 2013)).

Figure 41:
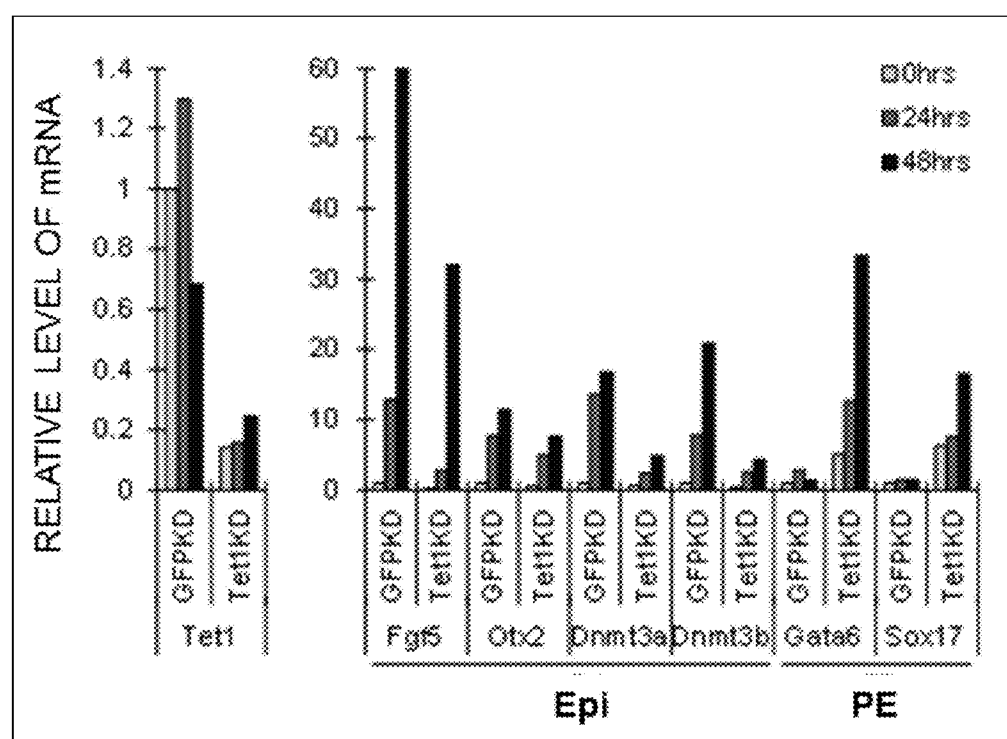
FIG. 41 The graph shows the results of qPCR data during the transition from the naïve to primed stage for the transcription levels of Tet1, Epiblast-related (Epi) and primitive endodermal (PE) markers by comparing Tet1-KD mouse ES cells (Tet1KD) and their control (GFP-KD) cells.

However, Tet1-KD mouse ES cells were unable to transit to the primed EpiLC pluripotent status like untreated cell. Instead, genes which are known to be highly expressed at the primed stage, especially the de novo DNA methyltransferases (Dnmt3a and Dnmt3b) were expressed in significantly lower levels in Tet1-KD EpiLCs (FIGS. 41 to 43).

Figure 42:
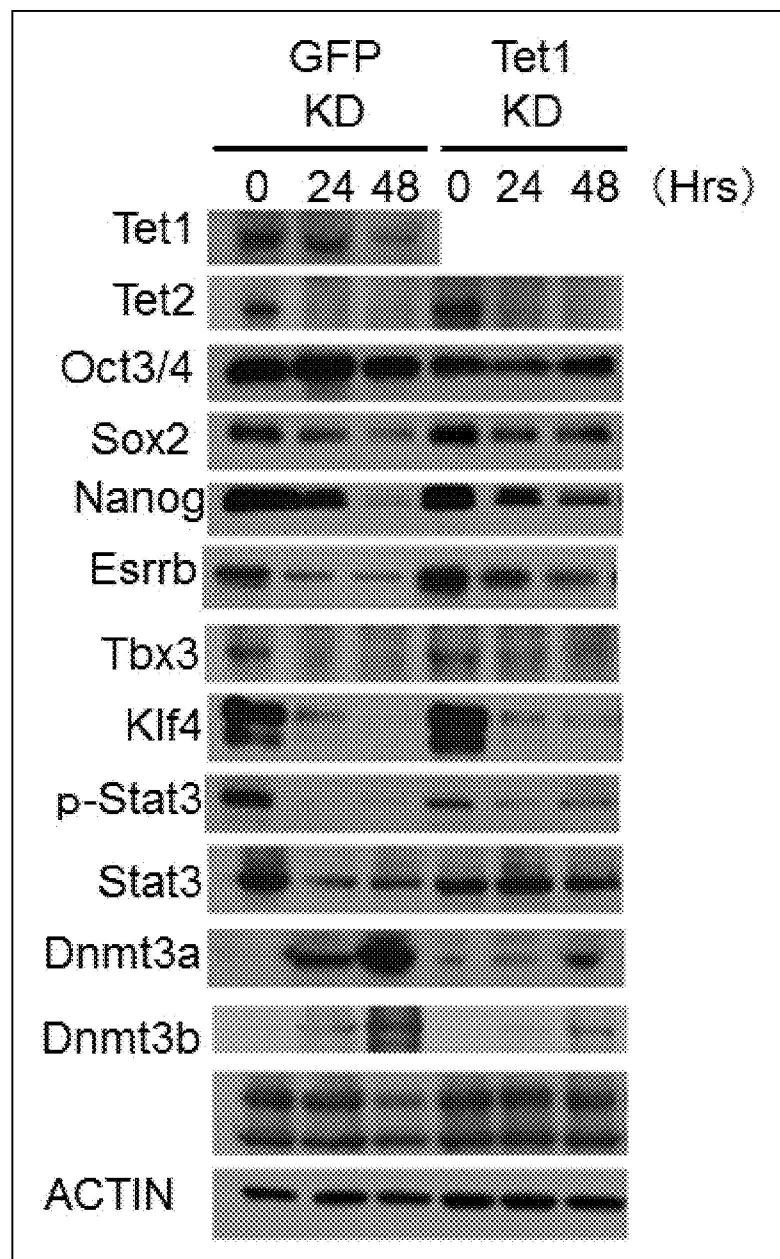
FIG. 42 The photograph shows the results of western blots for the protein levels of Tet1, Tet2, ICM markers and epiblast markers in Tet1-KD mouse ES cells (Tet1-KD) and GFP-KD mouse ES cells (GFP-KD). Of note, protein expression levels of naïve factors (such as Nanog, Esrrb, Tbx3 and Stat3) were largely maintained through the transition in Tet1-KD EpiLCs.
Figure 43:
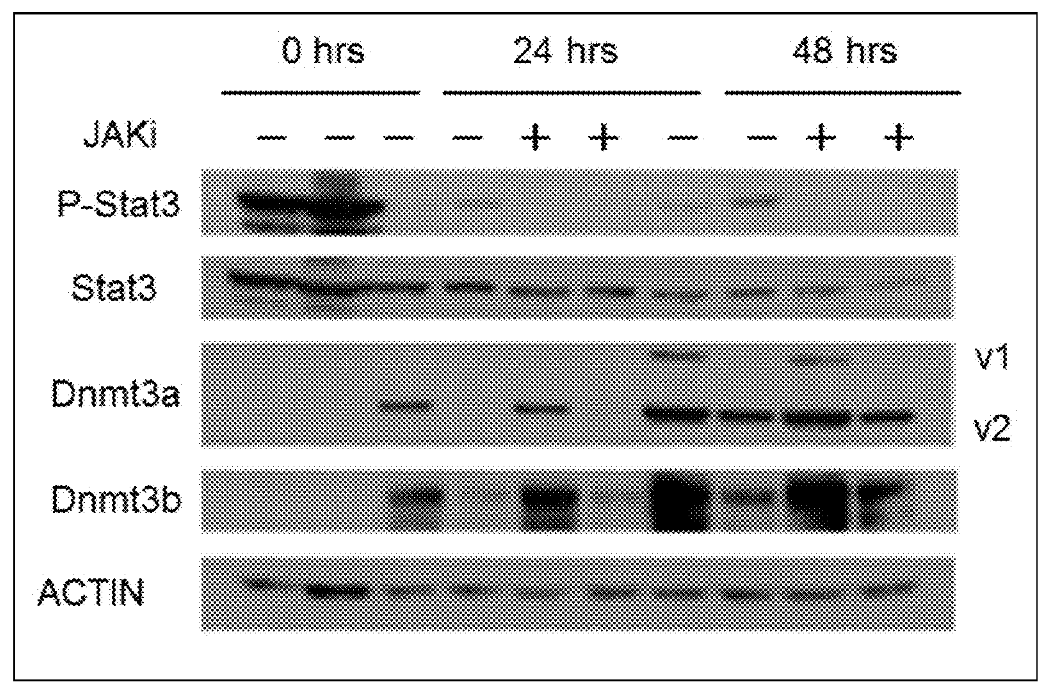
FIG. 43 The photograph shows the results of western blots for the protein expression levels of Stat3, Dnmt3a and Dnmt3b in the presence (JAKi+) or absence (JAKi−) of JAK inhibitor during the naïve to primed transition. As a JAKi, JAK Inhibitor I (Calbiochem, added at 1 μM) was used. For Dnmt3a, two bands appeared on the blots which correspond to v1 and v2 variants.

Moreover, the expression levels of the naïve factors (Nanog, Prdm14, Esrrb, Rex1/Zfp42, Tcl1, Tbx3, Klf2, Klf4 and Stat3) were maintained in Tet1-KD EpiLCs (FIG. 42 and FIG. 40).

Overall, the proteome and transcriptome of the Tet1-KD EpiLCs indicates that the cells expressed markers typical of an earlier developmental stage but also that, without Tet1 expression, mouse ES cells cannot transit to a primed pluripotency anymore within 48 hours.

Figure 44:
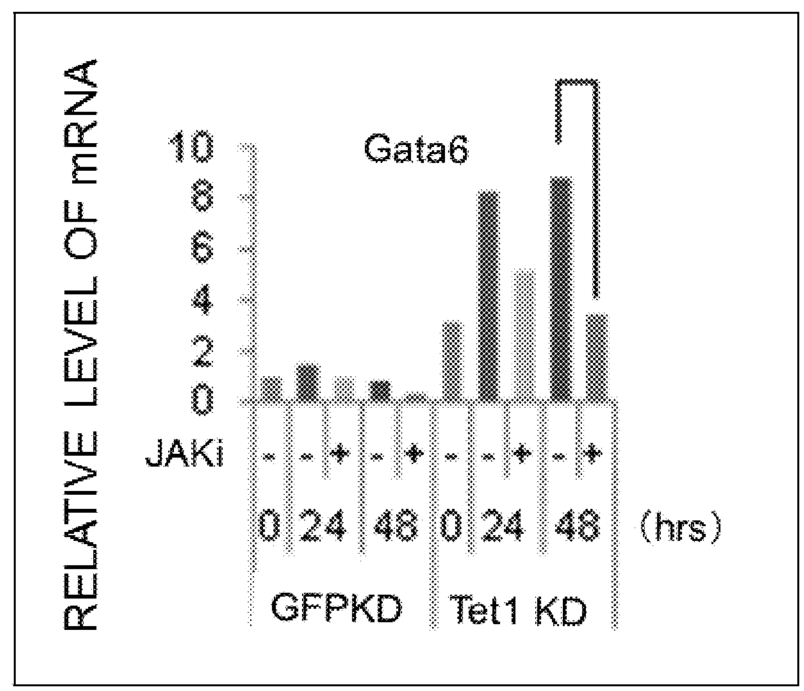
FIG. 44 The graph shows the qPCR results for Gata6 transcription levels upon naïve to primed transition in the presence (JAKi+) or absence (JAKi−) of JAK inhibitor.

Moreover, some transcription factors typically expressed in the primitive endoderm (such as Gata6 and Sox17) have been found to be expressed in the Tet1-KD EpiLCs. These signals are normally found in the preimplantation naïve cells of the blastocyst ICM. Furthermore, even when forced to transit to the epiblast (primed stage) by inhibiting the JAK signaling pathway which normally acts in the maintenance of the naïve status, Tet1-KD EpiLCs did not transit to the (epiblast) primitive ectodermal stage 48 hours after induction (FIG. 44).

Working Example 13

<TET1 Degradation at the Primed Pluripotency>

Figure 45:
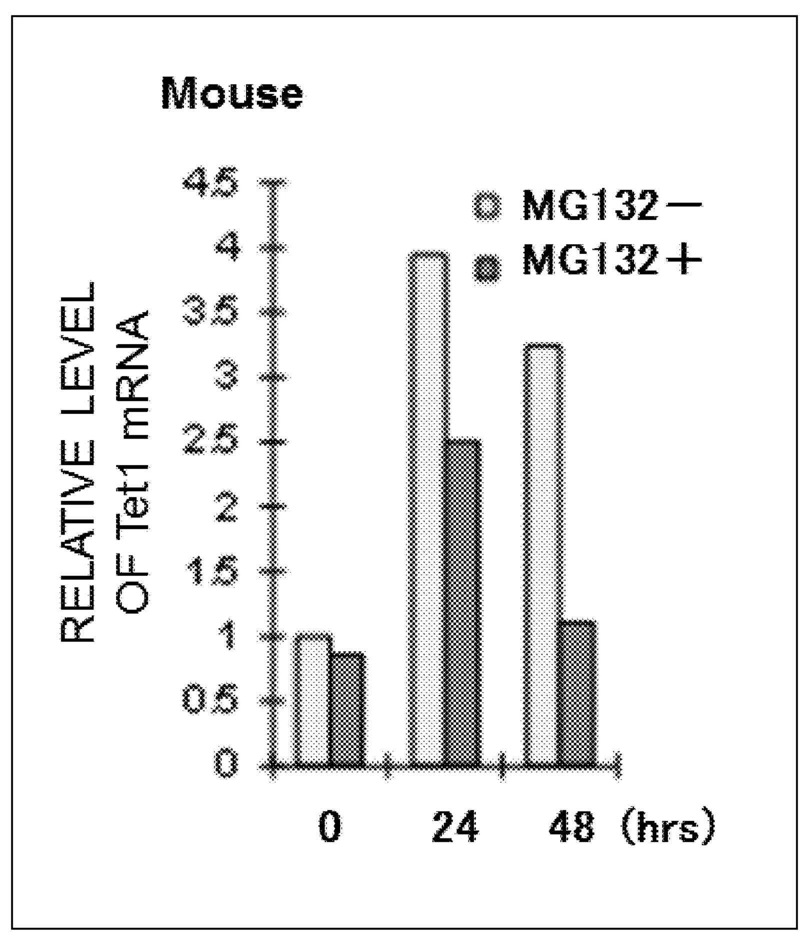
FIG. 45 The graph shows the qPCR results showing Tet1 mRNA levels upon naïve to primed transition of mouse ES cells in the presence (MG132+) or absence (MG132−) of MG132.
Figure 46:
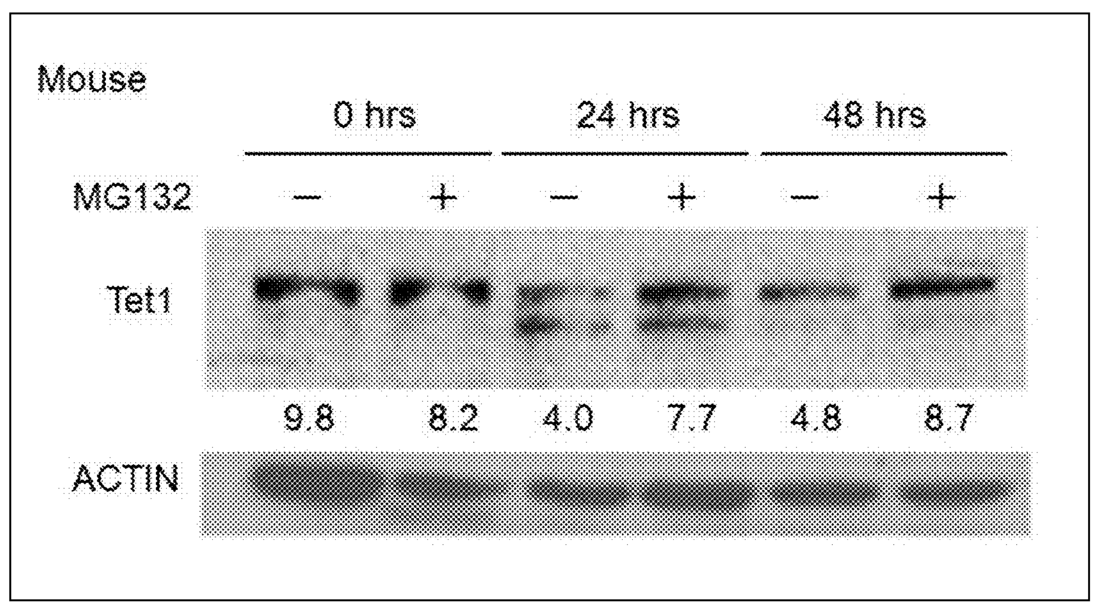
FIG. 46 The photograph shows the results of western blots for the protein expression levels of Tet1 upon naïve to primed transition of mouse ES cells in the presence (MG132+) or absence (MG132−) of MG132. Numbers shown in the figure are TET1 expression amount normalized against the actin expression amount.

When analyzed through the transition period of naïve-to-primed, as reported in "S. Ito et al., Nature 466, 1129 (Aug. 26, 2010)", Tet1 was highly expressed in the undifferentiated mouse ES cells (FIG. 45, FIG. 46 and FIG. 41). Upon transition to a primed stage, albeit that Tet1 mRNA level is maintained, their protein levels went significantly down (FIG. 45, FIG. 46, FIG. 41 and FIG. 42). However, upon applying the proteasome inhibitor MG132 and inhibiting protein degradation, the inventors were now able to detect Tet1 proteins (FIG. 46). In contrast, such regulation of Tet1 protein levels were not observed when the naïve undifferentiated ES cells were used.

As aforementioned, TET1 protein is hardly detectable in human iPSCs and therefore phenotypically, the cells can be supposed to be equivalent to the mouse primed EpiLCs in terms of its protein regulatory dynamics. Moreover, TET1 protein levels in hiPSCs were significantly up-regulated upon MG132 treatment (FIG. 1).

Thus, it became clear that TET1 protein is unable to be stabilized in a primed pluripotent stem cell as much as in a naïve pluripotent stem cell. In addition, the observed down-regulation of Tet1 protein in an in vitro model of development mimicking the naïve-to-primed transition suggests that Tet1 protein is programmed during development to down-regulate its expression during the transition from blastocyst to epiblast.

Working Example 14

<Validation of the Effect of Tet1 on Dnmt3 Expressivity>

As Tet1 is known to execute demethylation, Tet1-KD mouse ES cells or EpiLCs are anticipated to bear hypermethylated genomes.

Figure 47:
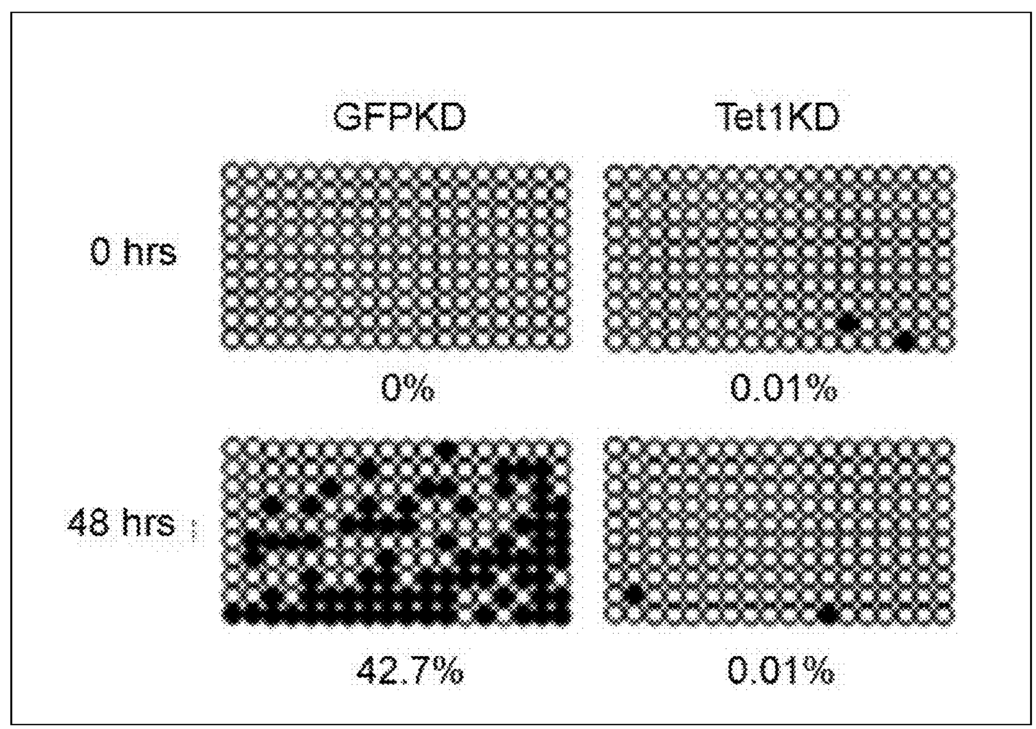
FIG. 47 Bisulfite sequencing results showing the DNA methylation statuses of the Tcl1 differentially methylated region (DMR) upon naïve to primed transition. Black circles denote for methylated (or hydroxymethylated) CpG sites and open (white) circles are for unmethylated (or unhydroxymethylated) CpG sites. Bisulfite sequencing of the selected CpG sites was performed according to H. Wu et al., Nature 473, 389 (May 19, 2011).

However, when the differentially-methylated region (DMR) of a gene of a naïve factor Tcl1 was analyzed, Tet1 loss did not affect the methylation status of the Tcl1-DMR in mouse ES cells. It should be noted that, however, the Tcl1-DMR has been reported as a region which acquires de novo methylation post-implantationally during blastocysts to epiblasts, as a part of a genome-wide methylation process (J. Borgel et al., Nat Genet 42, 1093 (December, 2010)). Furthermore, although the Tcl1 DMR acquired methylation in the process of transition to EpiLCs in control EpiLCs, Tet1-KD EpiLCs remained hypomethylated (FIG. 47).

Therefore, although Tet1 does not seem to directly affect the Tell-DMR methylation status through its demethylating activity, Tet1 expression at a naïve stage seems to affect the expressivity of the de novo DNA methyltransferases (Dnmt3a and Dnmt3b) important for the genome-wide re-methylation in an indirect fashion. In fact, as shown in FIG. 41, the expression levels of the DNA methyltransferases are fairly low in Tet1-KD EpiLCs.

So, the inventors went to look if the observed global hypomethylation and the dysregulation of Dnmt3a/b in the Tet1-KD EpiLCs could be explained by an aberration of the methylation status of Dnmt3b promoter region. The bisulfate sequencing of the supposed DMR of the Dnmt3b showed a hypermethylation at the region-866 to -576 of the transcription start site in Tet1-KD mouse ES cells and therefore this dysregulation seemed to be in accordance with the loss of the Tet1-demethylating activity.

However, this difference in the methylation status was rather subtle and therefore, the inventors went to look at a dioxygenase-independent molecular mechanism.

Prdm14, a naive factor, is known to inhibit the expression of Dnmt3b and to be partly responsible in harnessing the mouse ES cells their pluripotency (Z. Ma, T. Swigut, A.

Valouev, A. Rada-Iglesias, J. Wysocka, Nat Struct Mol Biol 18, 120 M. Yamaji et al., Cell Stem Cell 12, 368 and (February, 2011) (Mar. 7, 2013) reference). Therefore, the inventors analyzed Prdm14 expression in the process of naïve-to-primed transition.

As a result, Prdm14 mRNA was observed to be highly expressed at the naïve stage in mouse ES cells but went down upon EpiLC differentiation. However, upon Tet1-KD, Prdm14-down-regulation was attenuated upon EpiLC differentiation (FIG. 40). Tet1 is involved in the down-regulation of Prdm14 expression and as an effect, can be supposed to be involved in the up-regulation of Dnmt3a/b, and moreover, this result concords well with the observed down-regulation of Dnmt3a/b in the Tet1-KD EpiLCs.

Figure 48:
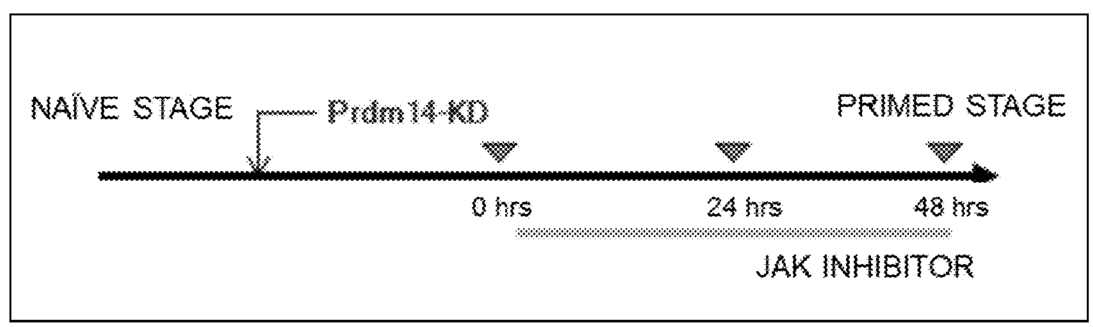
FIG. 48 Schematic drawing depicting the experimental scheme of the naïve to primed transition using Tet1/Prdm14 double knockdown mouse ES cells.
Figure 49:
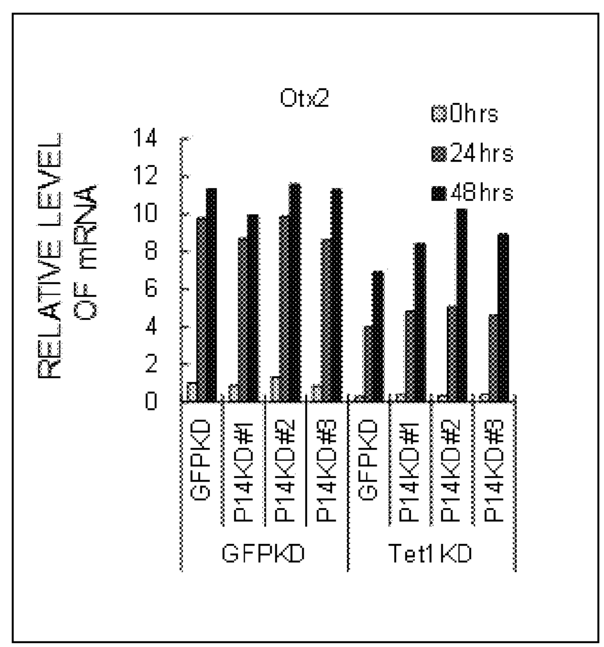
FIG. 49 The graph shows the qPCR results for Otx2 mRNA expression levels during the naïve to primed transition of Tet1/Prdm14 double knockdown mouse ES cells. "GFPKD GFPKD" is the control cell line used here in which only GFP-targeting shRNA was introduced, "GFPKD P14KD#1 to 3" are cell lines in which both GFP and Prdm14 are targeted by shRNA, "Tet1KD GFPKD" are cell lines in which both GFP and Tet1 are targeted by shRNA and "Tet1KD P14KD#1 to 3" are cell lines in which both Tet1 and Prdm14 are targeted by shRNA. (These notations are also valid for FIGS. 50 to 52.)
Figure 50:
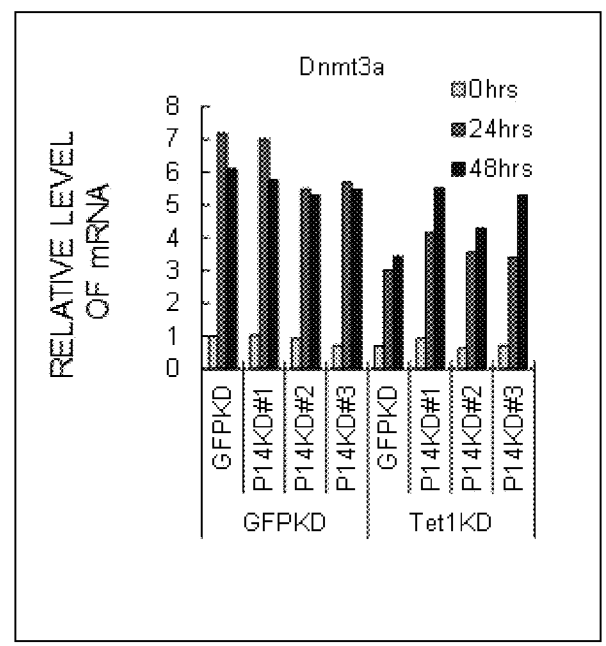
FIG. 50 The graph shows the qPCR results for Dnmt3a mRNA expression levels upon naïve to primed transition of Tet1/Prdm14 double knockdown mouse ES cells.
Figure 51:
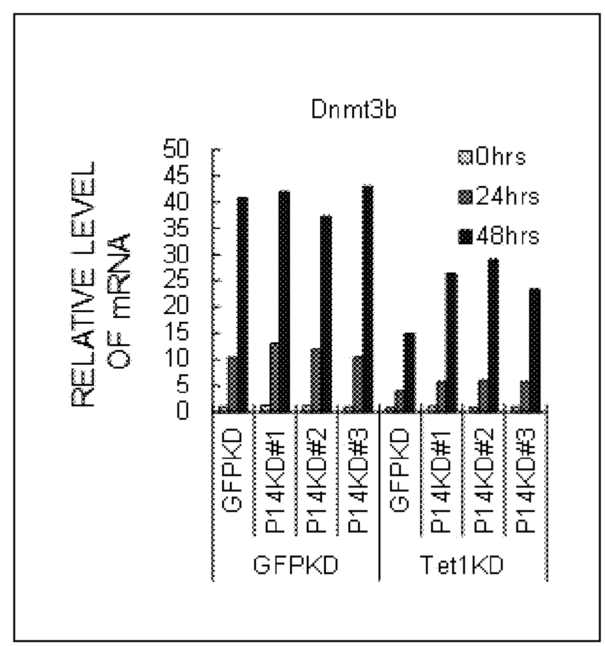
FIG. 51 The graph shows the qPCR results for Dnmt3b mRNA expression levels upon naïve to primed transition of Tet1/Prdm14 double knockdown mouse ES cells.
Figure 52:
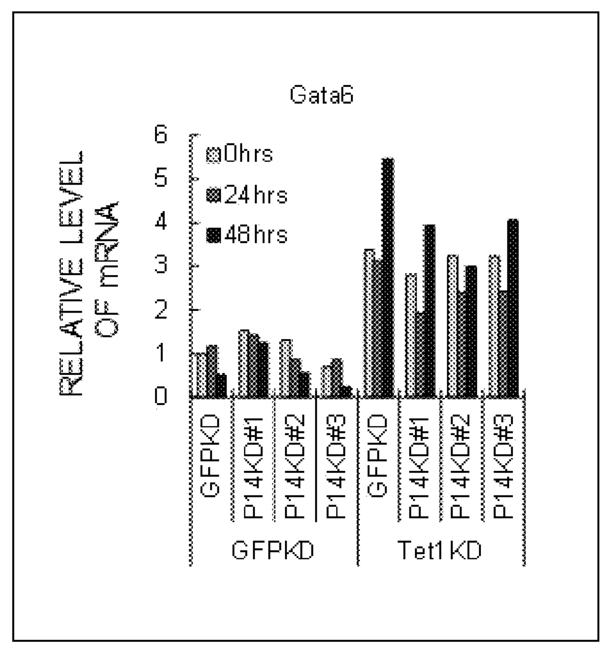
FIG. 52 The graph shows the qPCR results for Gata6 mRNA expression levels upon naïve to primed transition of Tet1/Prdm14 double knockdown mouse ES cells.

Next, the effect of knocking down both Prdm14 and Tet1 (Tet1/Prdm14-double KD) was analyzed in EpiLC for reversal of decreased Dnmt3b expression due to Tet1 loss (FIG. 48).

When compared to Tet1-KD, Tet1/Prdm14-double KD EpiLC expressed higher levels of Otx2, Dnmt3a and Dnmt3b transcripts (all indicators of the primed stage of development) but expressed lower level of the (extraembryonic) primitive endoderm marker Gata6 (FIGS. 49 to 52).

Collectively, the induction of decreased expression of Dnmt3a and Dnmt3b during naïve-to-primed transition of Tet1-KD and the concomitant hypomethylated genome of Tet1-KDEpiLC is suggestive that Tet1 is involved in this process in a dioxygenase-dependent as well as independent manner.

Next, to evaluate the differential contribution of the Dnmt3 isoforms during the naïve-to-primed transition, various Dnmt3 isoforms were introduced into the Tet1-KD cells.

Figure 53:
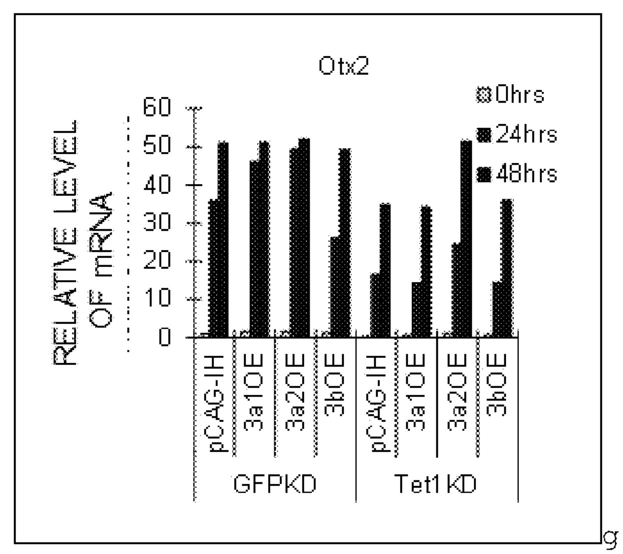
FIG. 53 The graph shows the qPCR results for Otx2 mRNA upon naïve to primed transition of mouse ES cells over-expressing Dnmt3a1 (3a1OE), Dnmt3a2 (3a2OE) and Dnmt3b (3bOE). "GFPKD pCAG-IH" is the control cell line in which a mock vector (pCAG-IH) and an shRNA targeting GFP are introduced, "GFPKD 3a1OE" is the cell line in which an shRNA targeting GFP and a Dnmt3a1-expressing pCAG-IH vector are introduced, "GFPKD 3a2OE" is the cell line in which an shRNA targeting GFP and a Dnmt3a2-expressing pCAG-IH vector are introduced, "GFPKD 3bOE" is the cell line in which an shRNA targeting GFP and a Dnmt3b-expressing pCAG-IH vector are introduced. "Tet1KD pCAG-IH" is a cell line in which an shRNA targeting Tet1 and a mock vector are introduced, "Tet1KD 3a1OE" is a cell line in which an shRNA targeting Tet1 and a pCAG-IH vector encoding Dnmt3a1 are introduced, "Tet1KD 3a2OE" is a cell line in which an shRNA targeting Tet1 and a pCAG-IH vector encoding Dnmt3a2 are introduced and "Tet1KD 3bOE" is a cell line in which an shRNA targeting Tet1 and a pCAG-IH vector encoding Dnmt3b are introduced. (These notations are also valid for FIG. 54.)
Figure 54:
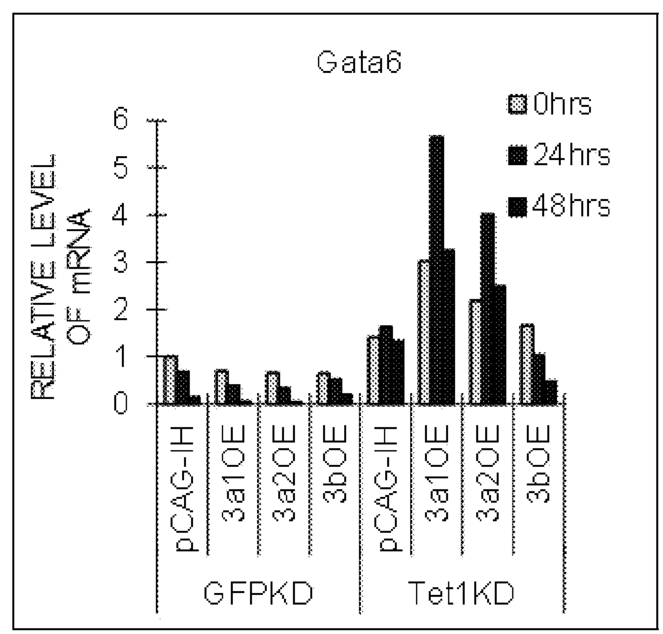
FIG. 54 The graph shows the qPCR results for Gata6 mRNA upon naïve to primed transition of mouse ES cells over-expressing Dnmt3a1 (3a1OE), Dnmt3a2 (3a2OE) and Dnmt3b (3bOE).

The ectopic expression of Dnmt3a2 into the Tet1-KDs recovered the Otx2 expression level to a similar level of the wild-type cells (FIG. 53). In contrast, Gata6 over-expression observed in the Tet1-KD cells was cancelled upon Dnmt3b ectopic expression (FIG. 54).

Therefore, the inventors concluded that Tet1 was actively responsible for the naïve-to-primed transition of pluripotencies in mouse ES cells through its regulation of Dnmt3a/b.

As aforementioned in the Working examples 1 to 9 and 11, by introducing a mutant TET1 protein where its second amino acid from the N-terminus was replaced from its wild-type amino acid into human PSCs, it was made clear that it is possible now to drastically enhance their differentiation efficacies. Furthermore, it was made clear that to drastically enhance their differentiation efficacies of human PSCs by expressing the mutant TET1 protein in human PSCs where normal TET1 protein is actively degraded. Moreover, by this enhancement of the differentiation efficacy of the PSCs, it has been shown that it is possible to resolve the differentiation biases inherent to the conventional human iPS cells (for example, the differentiation propensity toward the mesendoderm shown in the Working example 5). Moreover, such enhancement of the differentiation efficacy has been proven to be achievable by using a mutant TET1 protein where its second amino acid from its N-terminus has been replaced and also where its dioxygenase region has been deleted. Therefore, one can deduce from this result that the DNA demethylating activity exerted by the dioxygenase region of TET1 is redundant and that the DNA-binding domain of TET1 protein is sufficient for such effects.

Moreover, as shown in the Working example 10, by this invention, it is now possible not only to enhance the differentiation efficacy of a given PSC but also to enhance the production efficacy of such PSC.

As mentioned previously, TET1 protein is expressed throughout from the fertilized egg to the blastocyst in the naive embryonic cells. This fact, in combination with the discovery of this invention that TET1 protein is not expressed in primed human PSCs, together with the differentiation efficacy enhancing effect of introducing the mutant TET1 into such PSCs, strongly suggests that TET1 protein's function is to facilitate the transition of the naive blastocyst to the primed epiblast in early development and further toward differentiation into each germ lineages. Actually, as described in Examples 12 to 14, the present invention revealed that a TET1 protein actively led mouse ES cells from the naive stage to the primed pluripotent stage by controlling the expressions of Dnmt3a/b.

Therefore, TET1 protein functions as a lubricant for cell differentiation in general, or in other words, TET1 harnesses the robustness for the development to proceed. It is therefore strongly suggested that the observed effect of the TET1 protein on the enhancement of differentiation efficacy of PSCs is a consequence of an increase of robustness for differentiation.

INDUSTRIAL APPLICABILITY

As explained so far, the introduction of the mutant TET1 protein not only swiftly down-regulates the differentiation resistant factor NANOG but also, can enhance cell differentiation efficacy by up-regulating factors which actively promote cell differentiation.

The TET1 proteins and the methods for producing pluripotent stem cells which utilize these TET1 proteins of this invention are superior in that they can release the PSCs from the differentiation resistance by NANOG or differentiation propensities exhibited by endoderm/mesoderm marker T and SOX17 expression and allow one to obtain only the desired cell type at high efficacy. Therefore, this invention is useful in regenerative medicine, drug discovery and reproductive medicine where the supplies of various cell types, tissues or organs are strongly desired.

SEQUENCE LISTING FREE TEXT

SEQ ID NOs: 7 to 44

<223> artificially synthesized primer sequences

SEQ ID NOs: 45 and 46

<223> sequences of FLAG tag

What is claimed is:

1. A method for enhancing efficiency of differentiation of human induced pluripotent stem cells (iPSCs) towards neuronal lineages, in vitro, said method comprising:

introducing into induced human pluripotent stem cells (iPSCs), at least one molecule selected from the group consisting of (a) a nucleic acid that encodes a mutant human TET1 protein having the amino acid sequence selected from the group consisting of SEQ ID NO: 2, 4 and 6, and partial sequences thereof having at least amino acids 1 through 613 of SEQ ID NO: 2, 4 and 6, said amino acid sequence incorporating the binding domain at amino acids 585 to 613 and said mutant human TET1 protein having the second amino acid from the N-terminus substituted with another amino acid and (b) a vector into which a nucleic acid that encodes said mutant human TET1 protein has been inserted, to provide transformed iPSCs that express said mutant human TET1 protein;

wherein said expressed mutant human TET1 protein has enhanced stability as compared to the corresponding non-mutant human TET1 protein selected from the group consisting of SEQ ID NO: 2, 4 and 6, wherein said enhanced stability is determined by Western blotting and wherein expressed mutant human TET1 protein enhances the efficiency of differentiation of said induced pluripotent stem cells.

2. The method of claim 1, wherein said mutant human TET1 protein lacks its dioxygenase domain.

3. The method of claim 1, wherein said mutant human TET1 protein is the mutant human TET1 protein in which the second amino acid from the N-terminus is substituted with glycine in the amino acid sequence of SEQ ID NO: 2, 4 and 6 or the partial sequence thereof comprising at least amino acids 1 through 613 of SEQ ID Nos. 2, 4 or 6, and incorporating the binding domain at amino acids 585 to 613.

4. The method of claim 2, wherein said dioxygenase domain consists of amino acids 1611 to 2074 in SEQ ID NO: 2, amino acids 1640 to 2103 in SEQ ID NO: 4 or amino acids 809 to 1272 in SEQ ID NO: 6.

5. A method for enhancing efficiency of differentiation of induced pluripotent stem cells (iPSCs) towards neuronal lineages, in vitro, said method comprising:

introducing into induced human pluripotent stem cells, at least one molecule selected from the group consisting of (a) a nucleic acid that encodes a mutant human TET1 protein having the amino acid sequence selected from the group consisting of SEQ ID NO: 2, 4 and 6, and partial sequences thereof having at least amino acids 1 through 613 of SEQ ID NO: 2, 4 and 6, said amino acid sequence incorporating the binding domain at amino acids 585 to 613 and said mutant human TET1 protein having the amino acid sequence of SEQ ID NO: 46 inserted between the first and second amino acid from the N-terminus, wherein said insertion results in the substitution of the serine at the second position with another amino acid and (b) a vector into which a nucleic acid that encodes the mutant human TET1 protein has been inserted, to provide transformed (iPSCs) that express said mutant human TET1 protein, wherein said expressed mutant human TET1 protein has enhanced stability as compared to the corresponding non-mutant human TET1 protein selected from the group consisting of SEQ ID NO: 2, 4 and 6, wherein said enhanced stability is determined by Western blotting and wherein expressed mutant human TET1 protein enhances the efficiency of differentiation of said induced pluripotent stem cells.

6. The method of claim 1, wherein said nucleic acid is operably linked to a regulatory sequence for expression of the mutant human TET1 protein encoded by the nucleic acid.

7. The method of claim 3, wherein said nucleic acid is operably linked to a regulatory sequence for expression of the mutant human TET1 protein encoded by the nucleic acid.

8. The method of claim 5, wherein said nucleic acid is operably linked to a regulatory sequence for expression of the mutant human TET1 protein encoded by the nucleic acid.

9. A method for enhancing efficiency of differentiation of human induced pluripotent stem cells (iPSCs) towards neuronal lineages, in vitro, said method comprising:

introducing together into human somatic cells reprogramming factors for induction to induced pluripotent stem cells, and at least one molecule selected from the group consisting of (a) a nucleic acid that encodes a mutant human TET1 protein having the amino acid sequence selected from the group consisting of SEQ ID NO: 2, 4 and 6, and partial sequences thereof having at least amino acids 1 through 613 of SEQ ID NO: 2, 4 and 6, said amino acid sequence incorporating the binding domain at amino acids 585 to 613 and said mutant human TET1 protein having the second amino acid from the N-terminus substituted with another amino acid and (b) a vector into which a nucleic acid that encodes said mutant human TET1 protein has been inserted, to provide iPSCs from somatic cells that express said mutant human TET1 protein;

wherein said expressed mutant human TET1 protein has enhanced stability as compared to the corresponding non-mutant human TET1 protein selected from the group consisting of SEQ ID NO: 2, 4 and 6, wherein said enhanced stability is determined by Western blotting and wherein expressed mutant human TET1 protein enhances the efficiency of differentiation of said induced pluripotent stem cells.

10. The method of claim 9, wherein said reprogramming factors are selected from the group consisting of Oct3/4, Sox2, Klf4, L-MYC, LIN28, and shp53 and combinations thereof.

11. The method of claim 9, wherein said reprogramming factors include each of Oct3/4, Sox2, Klf4, L-MYC, LIN28, and shp53.

12. A method for enhancing efficiency of differentiation of induced pluripotent stem cells (iPSCs) towards neuronal lineages, in vitro, said method comprising:

introducing together into human somatic cells reprogramming factors for induction to induced pluripotent stem cells, and at least one molecule selected from the group consisting of (a) a nucleic acid that encodes a mutant human TET1 protein having the amino acid sequence selected from the group consisting of SEQ ID NO: 2, 4 and 6, and partial sequences thereof having at least amino acids 1 through 613 of SEQ ID NO: 2, 4 and 6, said amino acid sequence incorporating the binding domain at amino acids 585 to 613 and said mutant human TET1 protein having the amino acid sequence of SEQ ID NO: 46 inserted between the first and second amino acid from the N-terminus, wherein said insertion results in the substitution of the serine at the second position with another amino acid and (b) a vector into which a nucleic acid that encodes the mutant human TET1 protein has been inserted, to provide iPSCs from somatic cells that express said mutant human TET1 protein, wherein said expressed mutant human TET1 protein has enhanced stability as compared to the corresponding non-mutant human TET1 protein selected from the group consisting of SEQ ID NO: 2, 4 and 6, wherein said enhanced stability is determined by Western blotting and wherein expressed mutant human TET1 protein enhances the efficiency of differentiation of said induced pluripotent stem cells.

13. The method of claim 12, wherein said reprogramming factors are selected from the group consisting of Oct3/4, Sox2, Klf4, L-MYC, LIN28, and shp53, and combinations thereof.

14. The method of claim 12, wherein said reprogramming factors include each of Oct3/4, Sox2, Klf4, L-MYC, LIN28, and shp53.

* * * * *